(12) United States Patent
Fedorkin et al.

(10) Patent No.: US 7,491,509 B2
(45) Date of Patent: Feb. 17, 2009

(54) SYSTEM FOR EXPRESSION OF GENES IN PLANTS

(75) Inventors: Oleg Fedorkin, Newark, DE (US); Shailaja Rabindran, Newark, DE (US); Vidadi Yusibov, Havertown, PA (US)

(73) Assignee: Fraunhofer USA, Inc., Plymouth, MI (US)

( * ) Notice: Subject to any disclaimer, the term of this patent is extended or adjusted under 35 U.S.C. 154(b) by 358 days.

(21) Appl. No.: 10/770,600

(22) Filed: Feb. 3, 2004

(65) Prior Publication Data

US 2005/0026291 A1    Feb. 3, 2005

Related U.S. Application Data

(60) Provisional application No. 60/444,615, filed on Feb. 3, 2003.

(51) Int. Cl.
    *C12P 21/02* (2006.01)
(52) U.S. Cl. .................. 435/69.1; 435/320.1; 435/235.1
(58) Field of Classification Search ........................ None
    See application file for complete search history.

(56) References Cited

U.S. PATENT DOCUMENTS

| | | | |
|---|---|---|---|
| 5,939,541 A | 8/1999 | Vance et al. | |
| 6,015,692 A | 1/2000 | Gyuris et al. | |
| 6,500,644 B1 | 12/2002 | Borchert et al. | |
| 6,858,426 B1 * | 2/2005 | Zhu et al. ............... | 435/320.1 |
| 2003/0135822 A1 | 7/2003 | Metzlaff et al. | |
| 2005/0091706 A1 | 4/2005 | Klimyuk et al. | |

FOREIGN PATENT DOCUMENTS

| | | |
|---|---|---|
| EP | 0067553 A2 | 5/1982 |
| WO | WO 00/25574 | 5/2000 |
| WO | WO 00/46350 | 8/2000 |
| WO | WO 02/068664 A1 | 9/2002 |
| WO | WO 2004/044161 A2 | 5/2004 |
| WO | WO 2005/049839 A2 | 6/2005 |

OTHER PUBLICATIONS

Spitsin et al., PNAS, vol. 96, 1999, pp. 2549-2553.*
Bendahmane et al., PNAS, vol. 99, 2002, pp. 3645-3650.*
Sit et al., J. Virology, vol. 75, 2001, pp. 9538-9542.*
Crameri, et al., *Nat Biotechnol.*, 14(3): 315-9, 1996.
Dagan, T. et al., Mol. Biol. Evol., 19(7): 1022-1025, 2002.
Dawson, et al., *Virology*, 172: 285-292, 1989.
French, et al., *Science*, 231: 1294-1297, 1986.
Gils, et al., *Plant Biotechnology Journal*, 3: 613-620, 2005.
Gleba, et al., *Current Opinion in Plant Biology*, 7: 182-188, 2004.
Gleba, et al., *Vaccine*, 23: 2042-2048, 2005.
Grantham, *Science*, 85: 862-864, 1974.
Kapila, et al., *Plant Science*, 122: 101-108, 1997.
Koev and Miller, *J. Virology*, 74(13): 5988-5996, 2000.
Marillonnet, et al., *Nature Biotechnology*, 23: 718 - 723, 2005.
Marillonnet, et al., *Proc. Natl. Acad. Sci. USA*, 101: 6852-6857, 2004.
Mathew; *Plant Viruses Online* (http://imagels.uidaho.eduivide/), 2006.
Mori, et al., *Plant Journal*, 27(1): 79-86, 2001.
Musiychuk, et al., *Influenza*, 1: 19-25, 2007.
Santi, et al., *PNAS*, 103(4): 861-866, 2006.
Schob, et al., *Mol. Gen. Genet.*, 256: 581-585, 1997.
Spitsin, et al., *Proc. Natl. Acad. Sci. USA* 96(5): 2549-2553, 1999.
Takamatsu, et al., *EMBO J.* 6: 307-311, 1987.
Takamatsu, et al., *FEBS Lett.* 269: 73-76, 1990.
Turpen, *Phil. Trans. R. Soc. Lond. B* , 354: 665-673, 1999.
Yusibov and Loesch-Fries, *Virology*, 208(1): 405-407, 1995.
Yusibov, et al., *Vaccine*, 20: 3155-3164, 2002.
Zang, J., *J. Mol. Evol.*, 50: 56-68, 2000.
International Search Report, PCT/US2004/03169, date of publication of the international Search Report May 26, 2005.
Supplementary Eurppean Search Report, 04707807.6, date of publication Feb. 7, 2007.

\* cited by examiner

*Primary Examiner*—James Ketter

(57) ABSTRACT

The present invention provides trans-complementation systems for expressing gene products in plants. In general, the invention provides systems including a carrier vector and a producer vector, both based on plant viruses. The producer vector is defective for at least one function needed for successful systemic infection of a plant, e.g., replication, cell-to-cell movement, or long distance movement. The carrier vector supplies the missing function in trans. Certain producer vectors lack a functional coat protein coding sequence, in which case the corresponding producer vector supplies coat protein in trans. The invention also provides novel plant viral vectors and methods of use, e.g., to produce polypeptides or active RNAs in plants.

12 Claims, 11 Drawing Sheets

Figure 2
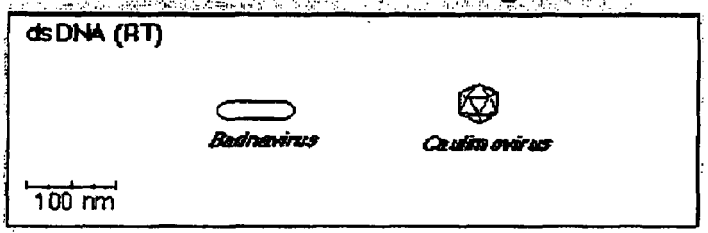
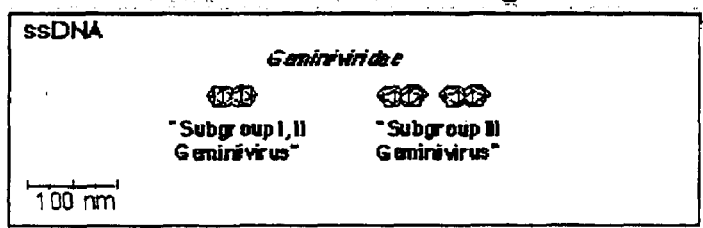
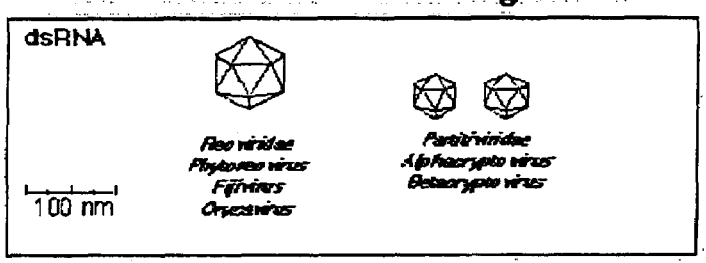

Figure 4
Pepper plants
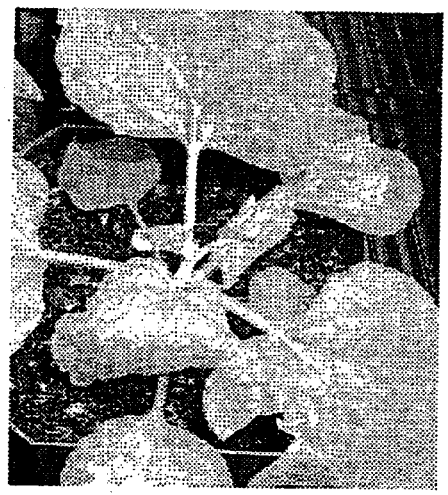
N. benthamiana hGH specific antibodies

```
SEQUENCE LISTING

<160> NUMBER OF SEQ ID NOS: 53

<210> SEQ ID NO 1
<211> LENGTH: 28
<212> TYPE: DNA
<213> ORGANISM: Artificial
<220> FEATURE:
<223> OTHER INFORMATION: Primer SR22 was used to clone hGH without its
      leader, and introducing a PacI site at the 5' end.

<400> SEQUENCE: 1
ccgttaatta atgttcccaa ctattcca                                      28

<210> SEQ ID NO 2
<211> LENGTH: 25
<212> TYPE: DNA
<213> ORGANISM: Artificial
<220> FEATURE:
<223> OTHER INFORMATION: Primer SR23 was used to clone hGH with its
      leader.

<400> SEQUENCE: 2
ttaattaatg gcaactggat caagg                                         25

<210> SEQ ID NO 3
<211> LENGTH: 24
<212> TYPE: DNA
<213> ORGANISM: Artificial
<220> FEATURE:
<223> OTHER INFORMATION: Primer SR24 was used to clone the hGH gene
      without KDEL and introducing a XhoI site at the 3' end.

<400> SEQUENCE: 3
cggctcgagt taaaaccac atga                                           24
```

<210> SEQ ID NO 4
<211> LENGTH: 30
<212> TYPE: DNA
<213> ORGANISM: Artificial
<220> FEATURE:
<223> OTHER INFORMATION: Primer SR25 was used to clone the gene with
      KDEL.

<400> SEQUENCE: 4
cggctcgagt tcatctttaa aacctgatcc                                      30

<210> SEQ ID NO 5
<211> LENGTH: 42
<212> TYPE: DNA
<213> ORGANISM: Artificial
<220> FEATURE:
<223> OTHER INFORMATION: Xho1 site at 3' end of A peptide with KDEL.

<400> SEQUENCE: 5
cggctcgagt cagagttcat ctttgttaca gtagttctca ag                        42

<210> SEQ ID NO 6
<211> LENGTH: 36
<212> TYPE: DNA
<213> ORGANISM: Artificial
<220> FEATURE:
<223> OTHER INFORMATION: Primer used to modify GFP from Aequorea
      Victoria.

<400> SEQUENCE: 6
gggagatctt aattaatggc tagcaaagga gaagaa                               36

<210> SEQ ID NO 7
<211> LENGTH: 45
<212> TYPE: DNA
<213> ORGANISM: Artificial
<220> FEATURE:
<223> OTHER INFORMATION: Primer used to modify GFP from Aequorea
      Victoria.

<400> SEQUENCE: 7
cccctcgagc ggccgctgca gttatttgta gagctcatcc atgcc                     45

<210> SEQ ID NO 8
<211> LENGTH: 23
<212> TYPE: DNA
<213> ORGANISM: Artificial
<220> FEATURE:
<223> OTHER INFORMATION: Primer used to modify GFP from Aequorea
      Victoria.

<400> SEQUENCE: 8
gttccctggc caacacttgt cac                                             23

<210> SEQ ID NO 9
<211> LENGTH: 22
<212> TYPE: DNA
<213> ORGANISM: Artificial
<220> FEATURE:
<223> OTHER INFORMATION: Primer used to modify GFP from Aequorea
      Victoria.

<400> SEQUENCE: 9
tagtgacaag tgttggccag gg                                              22

<210> SEQ ID NO 10

<210> SEQ ID NO 10
<211> LENGTH: 25
<212> TYPE: DNA
<213> ORGANISM: Artificial
<220> FEATURE:
<223> OTHER INFORMATION: Primer used to modify GFP from Aequorea
      Victoria.

<400> SEQUENCE: 10
ggacacaaac tggagtacaa ctata                                    25

<210> SEQ ID NO 11
<211> LENGTH: 25
<212> TYPE: DNA
<213> ORGANISM: Artificial
<220> FEATURE:
<223> OTHER INFORMATION: Primer used to modify GFP from Aequorea
      Victoria.

<400> SEQUENCE: 11
agttatagtt gtactccagt ttgtg                                    25

<210> SEQ ID NO 12
<211> LENGTH: 33
<212> TYPE: DNA
<213> ORGANISM: Artificial
<220> FEATURE:
<223> OTHER INFORMATION: Primer related to Alfalfa Mosaic virus

<400> SEQUENCE: 12
ccgctcgagc tgcagtgtac cccattaatt tgg                           33

<210> SEQ ID NO 13
<211> LENGTH: 35
<212> TYPE: DNA
<213> ORGANISM: Artificial
<220> FEATURE:
<223> OTHER INFORMATION: Primer related to Alfalfa mosaic virus.

<400> SEQUENCE: 13
cgggtcgacg cggccgcgaa taggacttca tacct                         35

<210> SEQ ID NO 14
<211> LENGTH: 35
<212> TYPE: DNA
<213> ORGANISM: Artificial
<220> FEATURE:
<223> OTHER INFORMATION: Primer related to Alfalfa mosaic virus.

<400> SEQUENCE: 14
cgggtcgacg cggccgcaat atgaagtcga tccta                         35

<210> SEQ ID NO 15
<211> LENGTH: 35
<212> TYPE: DNA
<213> ORGANISM: Artificial
<220> FEATURE:
<223> OTHER INFORMATION: Primer related to Alfalfa mosaic virus.

<400> SEQUENCE: 15
cgggtcgacg cggccgcgca tcccttaggg gcatt                         35

<210> SEQ ID NO 16
<211> LENGTH: 424
<212> TYPE: PRT
<213> ORGANISM: Tobamovirus/TMV-KR

<400> SEQUENCE: 16

-continued

```
Lys Gln Met Ser Ser Ile Val Tyr Thr Gly Pro Ile Lys Val Gln Gln
 1               5                  10                  15

Met Lys Asn Phe Ile Asp Ser Leu Val Ala Ser Leu Ser Ala Ala Val
             20                  25                  30

Ser Asn Leu Val Lys Ile Leu Lys Asp Thr Ala Ala Ile Asp Leu Glu
         35                  40                  45

Thr Arg Gln Lys Phe Gly Val Leu Asp Val Ala Ser Arg Lys Trp Leu
     50                  55                  60

Ile Lys Pro Thr Ala Lys Ser His Ala Trp Gly Val Glu Thr His
65                  70                  75                  80

Ala Arg Lys Tyr His Val Ala Leu Leu Glu Tyr Asp Glu Gln Gly Val
                 85                  90                  95

Val Thr Cys Asp Asn Trp Arg Arg Val Ala Val Ser Ser Glu Ser Val
                100                 105                 110

Val Tyr Ser Asp Met Ala Lys Leu Arg Thr Leu Arg Arg Leu Leu Arg
             115                 120                 125

Asn Gly Glu Pro His Val Ser Ser Ala Lys Val Val Leu Val Asp Gly
        130                 135                 140

Val Pro Gly Cys Gly Lys Thr Lys Glu Ile Leu Ser Arg Val Asn Phe
145                 150                 155                 160

Asp Glu Asp Leu Ile Leu Val Pro Gly Lys Gln Ala Ala Glu Met Ile
                165                 170                 175

Arg Arg Arg Ala Asn Ser Ser Gly Ile Ile Val Ala Thr Lys Asp Asn
            180                 185                 190

Val Lys Thr Val Asp Ser Phe Met Met Asn Phe Gly Lys Ser Thr Arg
        195                 200                 205

Cys Gln Phe Lys Arg Leu Phe Ile Asp Glu Gly Leu Met Leu His Thr
    210                 215                 220

Gly Cys Val Asn Phe Leu Val Thr Met Ser Leu Cys Glu Ile Ala Tyr
225                 230                 235                 240

Val Tyr Gly Asp Thr Gln Gln Ile Pro Tyr Ile Asn Arg Val Ser Gly
                245                 250                 255

Phe Pro Tyr Pro Ala His Phe Ala Lys Leu Glu Val Asp Glu Val Glu
            260                 265                 270

Thr Arg Arg Thr Thr Leu Arg Cys Pro Ala Asp Val Thr His Tyr Leu
        275                 280                 285

Asn Arg Arg Tyr Glu Gly Phe Val Met Ser Thr Ser Ser Val Lys Lys
    290                 295                 300

Ser Val Ser Gln Glu Met Val Gly Gly Ala Ala Val Ile Asn Pro Ile
305                 310                 315                 320

Ser Lys Pro Leu His Gly Lys Ile Leu Thr Phe Thr Gln Ser Asp Lys
                325                 330                 335

Glu Ala Leu Leu Ser Arg Gly Tyr Ser Asp Val His Thr Val His Glu
            340                 345                 350

Val Gln Gly Glu Thr Tyr Ser Asp Val Ser Leu Val Arg Leu Thr Pro
        355                 360                 365

Thr Pro Val Ser Ile Ile Ala Gly Asp Ser Pro His Val Leu Val Ala
    370                 375                 380

Leu Ser Arg His Thr Cys Ser Leu Lys Tyr Tyr Thr Val Val Met Asp
385                 390                 395                 400

Pro Leu Val Ser Ile Ile Arg Asp Leu Glu Lys Leu Ser Ser Tyr Leu
                405                 410                 415
```

Leu Asp Met Tyr Lys Val Asp Ala
            420

<210> SEQ ID NO 17
<211> LENGTH: 424
<212> TYPE: PRT
<213> OR

```
Thr Pro Ile Ser Ile Ile Ala Gly Asp Ser Pro His Val Leu Val Ala
    370                 375                 380

Leu Ser Arg His Thr Cys Ser Leu Lys Tyr Tyr Thr Val Val Met Asp
385                 390                 395                 400

Pro Leu Val Ser Ile Ile Arg Asp Leu Glu Lys Leu Ser Ser Tyr Leu
                405                 410                 415

Leu Asp Met Tyr Lys Val Asp Ala
            420

<210> SEQ ID NO 18
<211> LENGTH: 424
<212> TYPE: PRT
<213> ORGANISM: Tobamovirus/TMV-vul

<400> SEQUENCE: 18

Lys Gln Met Ser Ser Ile Val Tyr Thr Gly Pro Ile Lys Val Gln Gln
1               5                   10                  15

Met Lys Asn Phe Ile Asp Ser Leu Val Ala Ser Leu Ser Ala Ala Val
            20                  25                  30

Ser Asn Leu Val Lys Ile Leu Lys Asp Thr Ala Ala Ile Asp Leu Glu
        35                  40                  45

Thr Arg Gln Lys Phe Gly Val Leu Asp Val Ala Ser Arg Lys Trp Leu
    50                  55                  60

Ile Lys Pro Thr Ala Lys Ser His Ala Trp Gly Val Val Glu Thr His
65                  70                  75                  80

Ala Arg Lys Tyr His Val Ala Leu Leu Glu Tyr Asp Glu Gln Gly Val
                85                  90                  95

Val Thr Cys Asp Asp Trp Arg Arg Val Ala Val Ser Ser Glu Ser Val
            100                 105                 110

Val Tyr Ser Asp Met Ala Lys Leu Arg Thr Leu Arg Arg Leu Leu Arg
        115                 120                 125

Asn Gly Glu Pro His Val Ser Ser Ala Lys Val Val Leu Val Asp Gly
    130                 135                 140

Val Pro Gly Cys Gly Lys Thr Lys Glu Ile Leu Ser Arg Val Asn Phe
145                 150                 155                 160

Asp Glu Asp Leu Ile Leu Val Pro Gly Lys Gln Ala Ala Glu Met Ile
                165                 170                 175

Arg Arg Arg Ala Asn Ser Ser Gly Ile Ile Val Ala Thr Lys Asp Asn
            180                 185                 190

Val Lys Thr Val Asp Ser Phe Met Met Asn Phe Gly Lys Ser Thr Arg
        195                 200                 205

Cys Gln Phe Lys Arg Leu Phe Ile Asp Glu Gly Leu Met Leu His Thr
    210                 215                 220

Gly Cys Val Asn Phe Leu Val Ala Met Ser Leu Cys Glu Ile Ala Tyr
225                 230                 235                 240

Val Tyr Gly Asp Thr Gln Gln Ile Pro Tyr Ile Asn Arg Val Ser Gly
                245                 250                 255

Phe Pro Tyr Pro Ala His Phe Ala Lys Leu Glu Val Asp Glu Val Glu
            260                 265                 270

Thr Arg Arg Thr Thr Leu Arg Cys Pro Ala Asp Val Thr His Tyr Leu
        275                 280                 285

Asn Arg Arg Tyr Glu Gly Phe Val Met Ser Thr Ser Ser Val Lys Lys
    290                 295                 300

Ser Val Ser Gln Glu Met Val Gly Gly Ala Ala Val Ile Asn Pro Ile
```

-continued

```
            305                 310                 315                 320
Ser Lys Pro Leu His Gly Lys Ile Leu Thr Phe Thr Gln Ser Asp Lys
                325                 330                 335

Glu Ala Leu Leu Ser Arg Gly Tyr Ser Asp Val His Thr Val His Glu
            340                 345                 350

Val Gln Gly Glu Thr Tyr Ser Asp Val Ser Leu Val Arg Leu Thr Pro
        355                 360                 365

Thr Pro Val Ser Ile Ile Ala Gly Asp Ser Pro His Val Leu Val Ala
    370                 375                 380

Leu Ser Arg His Thr Cys Ser Leu Lys Tyr Tyr Thr Val Val Met Asp
385                 390                 395                 400

Pro Leu Val Ser Ile Ile Arg Asp Leu Glu Lys Leu Ser Ser Tyr Leu
                405                 410                 415

Leu Asp Met Tyr Lys Val Asp Ala
            420

<210> SEQ ID NO 19
<211> LENGTH: 424
<212> TYPE: PRT
<213> ORGANISM: Tobamovirus/TOMV

<400> SEQUENCE: 19

Lys Gln Met Cys Ser Ile Val Tyr Thr Gly Pro Leu Lys Val Gln Gln
1               5                   10                  15

Met Lys Asn Phe Ile Asp Ser Leu Val Ala Ser Leu Ser Ala Ala Val
            20                  25                  30

Ser Asn Leu Val Lys Ile Leu Lys Asp Thr Ala Ala Ile Asp Leu Glu
        35                  40                  45

Thr Arg Gln Lys Phe Gly Val Leu Asp Val Ala Ser Lys Arg Trp Leu
    50                  55                  60

Val Lys Pro Ser Ala Lys Asn His Ala Trp Gly Val Val Glu Thr His
65                  70                  75                  80

Ala Arg Lys Tyr His Val Ala Leu Leu Glu His Asp Glu Phe Gly Ile
                85                  90                  95

Ile Thr Cys Asp Asn Trp Arg Arg Val Ala Val Ser Ser Glu Ser Val
            100                 105                 110

Val Tyr Ser Asp Met Ala Lys Leu Arg Thr Leu Arg Arg Leu Leu Lys
        115                 120                 125

Asp Gly Glu Pro His Val Ser Ser Ala Lys Val Val Leu Val Asp Gly
    130                 135                 140

Val Pro Gly Cys Gly Lys Thr Lys Glu Ile Leu Ser Arg Val Asn Phe
145                 150                 155                 160

Glu Glu Asp Leu Ile Leu Val Pro Gly Arg Gln Ala Ala Glu Met Ile
                165                 170                 175

Arg Arg Arg Ala Asn Ala Ser Gly Ile Ile Val Ala Thr Lys Asp Asn
            180                 185                 190

Val Arg Thr Val Asp Ser Phe Leu Met Asn Tyr Gly Lys Gly Ala Arg
        195                 200                 205

Cys Gln Phe Lys Arg Leu Phe Ile Asp Glu Gly Leu Met Leu His Thr
    210                 215                 220

Gly Cys Val Asn Phe Leu Val Glu Met Ser Leu Cys Asp Ile Ala Tyr
225                 230                 235                 240

Val Tyr Gly Asp Thr Gln Gln Ile Pro Tyr Ile Asn Arg Val Thr Gly
                245                 250                 255
```

```
Phe Pro Tyr Pro Ala His Phe Ala Lys Leu Glu Val Asp Glu Val Glu
            260                 265                 270

Thr Arg Arg Thr Thr Leu Arg Cys Pro Ala Asp Val Thr His Phe Leu
        275                 280                 285

Asn Gln Arg Tyr Glu Gly His Val Met Cys Thr Ser Ser Glu Lys Lys
    290                 295                 300

Ser Val Ser Gln Glu Met Val Ser Gly Ala Ala Ser Ile Asn Pro Val
305                 310                 315                 320

Ser Lys Pro Leu Lys Gly Lys Ile Leu Thr Phe Thr Gln Ser Asp Lys
                325                 330                 335

Glu Ala Leu Leu Ser Arg Gly Tyr Ala Asp Val His Thr Val His Glu
            340                 345                 350

Val Gln Gly Glu Thr Tyr Ala Asp Val Ser Leu Val Arg Leu Thr Pro
        355                 360                 365

Thr Pro Val Ser Ile Ile Ala Arg Asp Ser Pro His Val Leu Val Ser
    370                 375                 380

Leu Ser Arg His Thr Lys Ser Leu Lys Tyr Tyr Thr Val Val Met Asp
385                 390                 395                 400

Pro Leu Val Ser Ile Ile Arg Asp Leu Glu Arg Val Ser Ser Tyr Leu
                405                 410                 415

Leu Asp Met Tyr Lys Val Asp Ala
            420

<210> SEQ ID NO 20
<211> LENGTH: 423
<212> TYPE: PRT
<213> ORGANISM: Tobamovirus/PMMV

<400> SEQUENCE: 20

Lys Gln Met His Ala Met Val Tyr Thr Gly Pro Leu Lys Val Gln Gln
1               5                   10                  15

Cys Lys Asn Tyr Leu Asp Ser Leu Val Ala Ser Leu Ser Ala Ala Val
            20                  25                  30

Ser Asn Leu Lys Lys Ile Ile Lys Asp Thr Ala Ala Ile Asp Leu Glu
        35                  40                  45

Thr Lys Glu Lys Phe Gly Val Tyr Asp Val Cys Leu Lys Lys Trp Leu
    50                  55                  60

Val Lys Pro Leu Ser Lys Gly His Ala Trp Gly Val Val Met Asp Ser
65                  70                  75                  80

Asp Tyr Lys Cys Phe Val Ala Leu Leu Thr Tyr Asp Gly Glu Asn Ile
                85                  90                  95

Val Cys Gly Glu Thr Trp Arg Arg Val Ala Val Ser Ser Glu Ser Leu
            100                 105                 110

Val Tyr Ser Asp Met Gly Lys Ile Arg Ala Ile Arg Ser Val Leu Lys
        115                 120                 125

Asp Gly Glu Pro His Ile Ser Ser Ala Lys Val Thr Leu Val Asp Gly
    130                 135                 140

Val Pro Gly Cys Gly Lys Thr Lys Glu Ile Leu Ser Arg Val Asn Phe
145                 150                 155                 160

Asp Glu Asp Leu Val Leu Val Pro Gly Lys Gln Ala Ala Glu Met Ile
                165                 170                 175

Arg Arg Arg Ala Asn Ser Ser Gly Leu Ile Val Ala Thr Lys Glu Asn
            180                 185                 190

Val Arg Thr Val Asp Ser Phe Leu Met Asn Tyr Gly Arg Gly Pro Cys
        195                 200                 205
```

-continued

Gln Tyr Lys Arg Leu Phe Leu Asp Glu Gly Leu Met Leu His Pro Gly
    210                 215                 220
Cys Val Asn Phe Leu Val Gly Met Ser Leu Cys Ser Glu Ala Phe Val
225                 230                 235                 240
Tyr Gly Asp Thr Gln Gln Ile Pro Tyr Ile Asn Arg Val Ala Thr Phe
                245                 250                 255
Pro Tyr Pro Lys His Leu Ser Gln Leu Glu Val Asp Ala Val Glu Thr
            260                 265                 270
Arg Arg Thr Thr Leu Arg Cys Pro Ala Asp Ile Thr Phe Phe Leu Asn
        275                 280                 285
Gln Lys Tyr Glu Gly Gln Val Met Cys Thr Ser Ser Val Thr Arg Ser
    290                 295                 300
Val Ser His Glu Val Ile Gln Gly Ala Ala Val Met Asn Pro Val Ser
305                 310                 315                 320
Lys Pro Leu Lys Gly Lys Val Ile Thr Phe Thr Gln Ser Asp Lys Ser
                325                 330                 335
Leu Leu Leu Ser Arg Gly Tyr Glu Asp Val His Thr Val His Glu Val
            340                 345                 350
Gln Gly Glu Thr Phe Glu Asp Val Ser Leu Val Arg Leu Thr Pro Thr
        355                 360                 365
Pro Val Gly Ile Ile Ser Lys Gln Ser Pro His Leu Leu Val Ser Leu
    370                 375                 380
Ser Arg His Thr Arg Ser Ile Lys Tyr Tyr Thr Val Val Leu Asp Ala
385                 390                 395                 400
Val Val Ser Val Leu Arg Asp Leu Glu Cys Val Ser Ser Tyr Leu Leu
                405                 410                 415
Asp Met Tyr Lys Val Asp Val
            420

<210> SEQ ID NO 21
<211> LENGTH: 421
<212> TYPE: PRT
<213> ORGANISM: Tobamovirus/TMGMV

<400> SEQUENCE: 21

Lys Gln Met Ala Ser Val Val Tyr Thr Gly Ser Leu Lys Val Gln Gln
1               5                   10                  15

Met Lys Asn Tyr Val Asp Ser Leu Ala Ala Ser Leu Ser Ala Thr Val
            20                  25                  30

Ser Asn Leu Cys Lys Ser Leu Lys Asp Glu Val Gly Tyr Asp Ser Asp
        35                  40                  45

Ser Arg Glu Lys Val Gly Val Trp Asp Val Thr Leu Lys Lys Trp Leu
    50                  55                  60

Leu Lys Pro Ala Ala Lys Gly His Ser Trp Gly Val Val Leu Asp Tyr
65                  70                  75                  80

Lys Gly Lys Met Phe Thr Ala Leu Leu Ser Tyr Glu Gly Asp Arg Met
                85                  90                  95

Val Thr Glu Ser Asp Trp Arg Arg Val Ala Val Ser Ser Asp Thr Met
            100                 105                 110

Val Tyr Ser Asp Ile Ala Lys Leu Gln Asn Leu Arg Lys Thr Met Arg
        115                 120                 125

Asp Gly Glu Pro His Glu Pro Thr Ala Lys Met Val Leu Val Asp Gly
    130                 135                 140

Val Pro Gly Cys Gly Lys Tyr Lys Gly Asp Phe Glu Arg Phe Asp Leu

-continued

```
145                 150                 155                 160

Asp Glu Asp Leu Ile Leu Val Pro Gly Lys Gln Ala Ala Ala Met Ile
                165                 170                 175

Arg Arg Arg Ala Asn Ser Ser Gly Leu Ile Arg Ala Thr Met Asp Asn
            180                 185                 190

Val Arg Thr Val Asp Ser Leu Leu Met His Pro Lys Pro Arg Ser His
        195                 200                 205

Lys Arg Leu Phe Ile Asp Glu Gly Leu Met Leu His Thr Gly Cys Val
    210                 215                 220

Asn Phe Leu Val Leu Ile Ser Gly Cys Asp Ile Ala Tyr Ile Tyr Gly
225                 230                 235                 240

Asp Thr Gln Gln Ile Pro Phe Ile Asn Arg Val Gln Asn Phe Pro Tyr
                245                 250                 255

Pro Lys His Phe Glu Lys Leu Gln Val Asp Glu Val Glu Met Arg Arg
            260                 265                 270

Thr Thr Leu Arg Cys Pro Gly Asp Val Asn Phe Phe Leu Gln Ser Lys
        275                 280                 285

Tyr Glu Gly Ala Val Thr Thr Thr Ser Thr Val Gln Arg Ser Val Ser
    290                 295                 300

Ser Glu Met Ile Gly Gly Lys Gly Val Leu Asn Ser Val Ser Lys Pro
305                 310                 315                 320

Leu Lys Gly Lys Ile Val Thr Phe Thr Gln Ala Asp Lys Phe Glu Leu
                325                 330                 335

Glu Glu Lys Gly Tyr Lys Asn Val Asn Thr Val His Glu Ile Gln Gly
            340                 345                 350

Glu Thr Phe Glu Asp Val Ser Leu Val Arg Leu Thr Ala Thr Pro Leu
        355                 360                 365

Thr Leu Ile Ser Lys Ser Ser Pro His Val Leu Val Ala Leu Thr Arg
    370                 375                 380

His Thr Lys Ser Phe Lys Tyr Tyr Thr Val Val Leu Asp Pro Leu Val
385                 390                 395                 400

Gln Ile Ile Ser Asp Leu Ser Ser Leu Ser Ser Phe Leu Leu Glu Met
                405                 410                 415

Tyr Met Val Glu Ala
            420

<210> SEQ ID NO 22
<211> LENGTH: 424
<212> TYPE: PRT
<213> ORGANISM: Tobamovirus/TMV-OB

<400> SEQUENCE: 22

Asn Lys Met Ala Ser Ile Val Tyr Ser Gly Pro Leu Gln Val Gln Gln
1               5                   10                  15

Met Gln Asn Tyr Val Asp Ser Leu Ala Ala Ser Leu Ser Ala Thr Val
            20                  25                  30

Ser Asn Leu Lys Lys Leu Val Lys Asp Ser Ser Val Gly Phe Gln Asp
        35                  40                  45

Ser Leu Ser Lys Val Gly Val Phe Asp Val Arg Lys Lys Met Trp Leu
    50                  55                  60

Ile Lys Pro Thr Leu Lys Asn His Ser Trp Gly Val Val Gln Lys Phe
65                  70                  75                  80

Asp Gly Lys Cys Phe Leu Ala Leu Leu Ser Tyr His Asn Glu Leu Pro
                85                  90                  95
```

-continued

```
Ile Cys Asp Ala Asp Trp Ser Lys Val Ala Val Ser Asn Glu Ser Met
            100                 105                 110

Val Tyr Ser Asp Met Ala Lys Leu Arg Val Leu Arg Lys Ser Ile Gly
        115                 120                 125

Glu Met Pro Ile Ser Val Ser Ser Ala Lys Val Thr Leu Val Asp Gly
    130                 135                 140

Val Pro Gly Cys Gly Lys Thr Lys Glu Ile Leu Arg Arg Val Asn Phe
145                 150                 155                 160

Ser Glu Asp Leu Val Leu Val Pro Gly Lys Glu Ala Ala Ala Met Ile
                165                 170                 175

Arg Lys Arg Ala Asn Gln Ser Gly Asn Ile Val Ala Asn Asn Asp Asn
            180                 185                 190

Val Lys Thr Val Asp Ser Phe Leu Met Asn Leu Gly Lys Gly Pro Val
        195                 200                 205

Cys Gln Phe Lys Arg Leu Phe Val Asp Glu Gly Leu Met Leu His Pro
    210                 215                 220

Gly Cys Val Tyr Phe Leu Val Lys Leu Ser Leu Cys Asn Glu Ala Phe
225                 230                 235                 240

Val Phe Gly Asp Thr Gln Gln Ile Pro Tyr Ile Asn Arg Val Gln Asn
                245                 250                 255

Phe Pro Phe Pro Gln His Phe Ser Lys Leu Ile Val Asp Glu Thr Glu
            260                 265                 270

Lys Arg Arg Thr Thr Leu Arg Cys Pro Val Asp Val Thr His Phe Leu
        275                 280                 285

Asn Gln Cys Tyr Asp Gly Ala Val Thr Thr Thr Ser Lys Thr Gln Arg
    290                 295                 300

Ser Val Gly Leu Glu Val Val Gly Gly Ala Ala Val Met Asn Pro Val
305                 310                 315                 320

Thr Lys Pro Leu Lys Gly Lys Ile Val Thr Phe Thr Gln Ser Asp Lys
                325                 330                 335

Leu Thr Met Leu Ser Arg Gly Tyr Gln Asp Val Asn Thr Val His Glu
            340                 345                 350

Ile Gln Gly Glu Thr Tyr Glu Glu Val Ser Leu Val Arg Leu Thr Pro
        355                 360                 365

Thr Pro Ile His Ile Ile Ser Arg Glu Ser Pro His Val Leu Val Gly
    370                 375                 380

Leu Thr Arg His Thr Arg Cys Phe Lys Tyr Tyr Thr Val Val Leu Asp
385                 390                 395                 400

Pro Leu Val Lys Leu Val Arg Asp Leu Glu Cys Val Ser Asn Phe Leu
                405                 410                 415

Leu Asp Val Tyr Met Val Asp Ser
            420

<210> SEQ ID NO 23
<211> LENGTH: 426
<212> TYPE: PRT
<213> ORGANISM: Tobamovirus/ORSV

<400> SEQUENCE: 23

Lys Ser Met Ser Ser Ala Val Tyr Thr Gly Pro Leu Lys Val Gln Gln
1               5                   10                  15

Met Lys Asn Tyr Met Asp Tyr Leu Ser Ala Ser Ile Ser Ala Thr Val
            20                  25                  30

Ser Asn Leu Cys Lys Val Leu Lys Asp Val Tyr Gly Val Asp Pro Glu
        35                  40                  45
```

```
Ser Ala Glu Lys Ser Gly Val Tyr Asp Val Val Lys Gly Lys Trp Ile
 50                  55                  60

Ile Lys Pro Lys Asp Lys Cys His Ala Trp Gly Val Ala Asp Leu Asn
 65                  70                  75                  80

Asn Gly Glu Lys Val Ile Val Leu Leu Glu Trp Ala Asp Gly Phe Pro
                 85                  90                  95

Ile Cys Gly Asp Trp Arg Arg Val Ala Val Ser Ser Asp Ser Leu Ile
             100                 105                 110

Tyr Ser Asp Met Gly Lys Leu Gln Thr Leu Leu Arg Cys Leu Lys Asp
         115                 120                 125

Gly Glu Pro Val Leu Arg Met Pro Lys Val Thr Leu Val Asp Gly Val
     130                 135                 140

Leu Gly Cys Gly Lys Thr Lys Glu Ile Leu Glu Thr Val Asn Phe Asp
145                 150                 155                 160

Glu Glu Leu Ile Leu Val Pro Gly Lys Glu Ala Cys Lys Met Ile Ile
                 165                 170                 175

Lys Arg Ala Asn Lys Ser Gly His Val Arg Ala Thr Lys Asp Asn Val
             180                 185                 190

Arg Thr Val Asp Ser Phe Leu Met His Leu Lys Pro Lys Thr Tyr Asn
         195                 200                 205

Lys Leu Phe Ile Asp Glu Gly Leu Met Leu His Thr Gly Cys Val Asn
     210                 215                 220

Phe Leu Ile Ala Leu Ser His Cys Arg Glu Ala Met Val Phe Gly Asp
225                 230                 235                 240

Thr Glu Gln Ile Pro Phe Ile Asn Arg Val Ala Asn Phe Pro Tyr Pro
                 245                 250                 255

Lys His Phe Gly His Thr Cys Leu His Arg Arg Glu Val Arg Arg Leu
             260                 265                 270

Ser Leu Arg Cys Pro Ala Asp Val Thr His Phe Met Asn Ser Lys Tyr
         275                 280                 285

Asp Gly Lys Phe Leu Cys Thr Asn Asp Val Ile Arg Ser Val Asp Ala
     290                 295                 300

Glu Val Val Arg Gly Lys Gly Val Phe Asn Pro Lys Ser Lys Pro Leu
305                 310                 315                 320

Lys Gly Lys Ile Ile Thr Phe Thr Gln Ser Asp Lys Ala Glu Leu Asn
                 325                 330                 335

Glu Arg Gly Tyr Glu Glu Val Ser Thr Phe Gly Glu Ile Asn Thr Val
             340                 345                 350

His Glu Ile Gln Gly Glu Thr Phe Glu Asp Val Ser Val Val Arg Leu
         355                 360                 365

Thr Pro Thr Ala Leu Glu Leu Ile Ser Lys Ser Ser Pro His Val Leu
     370                 375                 380

Val Ala Leu Thr Arg His Thr Lys Ser Phe Lys Tyr Tyr Cys Val Val
385                 390                 395                 400

Leu Asp Pro Leu Val Lys Val Cys Ser Asp Leu Ser Lys Val Ser Asp
                 405                 410                 415

Phe Ile Leu Asp Met Tyr Lys Val Asp Ala
             420                 425

<210> SEQ ID NO 24
<211> LENGTH: 421
<212> TYPE: PRT
<213> ORGANISM: Tobamovirus/TVCV
```

<400> SEQUENCE: 24

```
Gly Thr Met Met Ser Ala Val Tyr Thr Gly Ser Ile Lys Val Gln Gln
 1               5                  10                  15

Met Lys Asn Tyr Ile Asp Tyr Leu Ser Ala Ser Leu Ala Ala Thr Val
            20                  25                  30

Ser Asn Leu Cys Lys Val Leu Arg Asp Val His Gly Val Asp Pro Glu
        35                  40                  45

Ser Gln Glu Lys Ser Gly Val Trp Asp Val Arg Arg Gly Arg Trp Leu
    50                  55                  60

Leu Lys Pro Asn Ala Lys Ser His Ala Trp Gly Val Ala Glu Asp Ala
65                  70                  75                  80

Asn His Lys Leu Val Ile Val Leu Leu Asn Trp Asp Asp Gly Lys Pro
                85                  90                  95

Val Cys Asp Glu Thr Trp Phe Arg Val Ala Val Ser Ser Asp Ser Leu
            100                 105                 110

Ile Tyr Ser Asp Met Gly Lys Leu Lys Thr Leu Thr Ser Cys Ser Pro
        115                 120                 125

Asn Gly Glu Pro Pro Glu Pro Asn Ala Lys Val Ile Leu Val Asp Gly
    130                 135                 140

Val Pro Gly Cys Gly Lys Thr Lys Glu Ile Ile Glu Lys Val Asn Phe
145                 150                 155                 160

Ser Glu Asp Leu Ile Leu Val Pro Gly Lys Glu Ala Ser Lys Met Ile
                165                 170                 175

Ile Arg Arg Ala Asn Gln Ala Gly Val Ile Arg Ala Asp Lys Asp Asn
            180                 185                 190

Val Arg Thr Val Asp Ser Phe Leu Met His Pro Ser Arg Arg Val Phe
        195                 200                 205

Lys Arg Leu Phe Ile Asp Glu Gly Leu Met Leu His Thr Gly Cys Val
    210                 215                 220

Asn Phe Leu Leu Leu Leu Ser Gln Cys Asp Val Ala Tyr Val Tyr Gly
225                 230                 235                 240

Asp Thr Lys Gln Ile Pro Phe Ile Cys Arg Val Ala Asn Phe Pro Tyr
                245                 250                 255

Pro Ala His Phe Ala Lys Leu Val Ala Asp Glu Lys Glu Val Arg Arg
            260                 265                 270

Val Thr Leu Arg Cys Pro Ala Asp Val Thr Tyr Phe Leu Asn Lys Lys
        275                 280                 285

Tyr Asp Gly Ala Val Met Cys Thr Ser Ala Val Glu Arg Ser Val Lys
    290                 295                 300

Ala Glu Val Val Arg Gly Lys Gly Ala Leu Asn Pro Ile Thr Leu Pro
305                 310                 315                 320

Leu Glu Gly Lys Ile Leu Thr Phe Thr Gln Ala Asp Lys Phe Glu Leu
                325                 330                 335

Leu Glu Lys Gly Tyr Lys Asp Val Asn Thr Val His Glu Val Gln Gly
            340                 345                 350

Glu Thr Tyr Glu Lys Thr Ala Ile Val Arg Leu Thr Ser Thr Pro Leu
        355                 360                 365

Glu Ile Ile Ser Ser Ala Ser Pro His Val Leu Val Ala Leu Thr Arg
    370                 375                 380

His Thr Thr Cys Cys Lys Tyr Tyr Thr Val Val Leu Asp Pro Met Val
385                 390                 395                 400

Asn Val Ile Ser Glu Met Glu Lys Leu Ser Asn Phe Leu Leu Asp Met
                405                 410                 415
```

Tyr Arg Val Glu Ala
            420

<210> SEQ ID NO 25
<211> LENGTH: 421
<212> TYPE: PRT
<213> ORGANISM: Tobamovirus/CR-TMV

<400> SEQUENCE: 25

Gly Thr Met Met Ser Ala Val Tyr Thr Gly Ser Ile Glu Val Arg Gln
1               5                   10                  15

Met L

```
                    355                 360                 365
Glu Ile Ile Ser Arg Ala Ser Pro His Val Leu Val Ala Leu Thr Arg
                370                 375                 380

His Thr Thr Arg Cys Lys Tyr Tyr Thr Val Val Leu Asp Pro Met Val
385                 390                 395                 400

Asn Val Ile Ser Glu Met Glu Lys Leu Ser Asn Phe Leu Leu Asp Met
                405                 410                 415

Tyr Arg Val Glu Ala
            420

<210> SEQ ID NO 26
<211> LENGTH: 421
<212> TYPE: PRT
<213> ORGANISM: Tobamovirus/RMV-SH

<400> SEQUENCE: 26

Gly Ala Met Met Ser Ala Val Tyr Thr Gly Lys Ile Lys Val Gln Gln
1               5                   10                  15

Met Lys Asn Tyr Val Asp Tyr Leu Ser Ala Ser Leu Ser Ala Thr Val
                20                  25                  30

Ser Asn Leu Cys Lys Val Leu Arg Asp Val His Gly Val Asp Pro Glu
            35                  40                  45

Ser Gln Glu Lys Ser Gly Val Trp Asp Val Arg Arg Gly Arg Trp Leu
        50                  55                  60

Leu Lys Pro Asn Ala Lys Cys His Ala Trp Gly Val Ala Glu Asp Ala
65                  70                  75                  80

Asn His Lys Leu Val Ile Val Leu Asn Trp Asp Glu Gly Asn Pro
                85                  90                  95

Val Cys Asp Glu Thr Trp Phe Arg Leu Ala Val Ser Ser Asp Ser Leu
            100                 105                 110

Val Tyr Ser Asp Met Gly Lys Leu Lys Thr Leu Thr Ala Cys Cys Arg
        115                 120                 125

Asp Gly Glu Pro Pro Glu Pro Thr Ala Lys Val Val Leu Val Asp Gly
    130                 135                 140

Val Pro Gly Cys Gly Lys Thr Lys Glu Ile Leu Glu Lys Val Asn Phe
145                 150                 155                 160

Ser Glu Asp Leu Val Leu Val Pro Gly Lys Glu Ala Ser Lys Met Ile
                165                 170                 175

Ile Arg Arg Ala Asn Gln Ala Gly Val Thr Arg Ala Asp Lys Asp Asn
            180                 185                 190

Val Arg Thr Val Asp Ser Phe Leu Met His Pro Pro Lys Arg Val Phe
        195                 200                 205

Lys Arg Leu Phe Ile Asp Glu Gly Leu Met Leu His Thr Gly Cys Val
    210                 215                 220

Asn Phe Leu Thr Leu Leu Ser His Cys Asp Val Ala Tyr Val Tyr Gly
225                 230                 235                 240

Asp Thr Gln Gln Ile Pro Phe Ile Cys Arg Val Ala Asn Phe Pro Tyr
                245                 250                 255

Pro Ser His Phe Ala Lys Leu Val Val Asp Glu Lys Glu Asp Arg Arg
            260                 265                 270

Val Thr Leu Arg Cys Pro Ala Asp Val Thr Tyr Phe Leu Asn Thr Arg
        275                 280                 285

Tyr Asp Gly Ser Val Met Cys Thr Ser Ser Val Glu Arg Ser Val Ser
    290                 295                 300
```

-continued

```
Ala Glu Val Val Arg Gly Lys Gly Ala Leu Asn Pro Ile Thr Leu Pro
305                 310                 315                 320

Leu Glu Gly Lys Ile Leu Thr Phe Thr Gln Ala Asp Lys Phe Glu Leu
            325                 330                 335

Leu Asp Lys Gly Tyr Lys Asp Val Asn Thr Val His Glu Val Gln Gly
        340                 345                 350

Glu Thr Tyr Glu Lys Thr Ala Ile Val Arg Leu Thr Ala Thr Pro Leu
    355                 360                 365

Glu Ile Ile Ser Arg Ala Ser Pro His Val Leu Val Ala Leu Thr Arg
370                 375                 380

His Thr Thr Arg Cys Lys Tyr Tyr Thr Val Val Leu Asp Pro Met Val
385                 390                 395                 400

Asn Val Ile Ser Glu Leu Gly Lys Leu Ser Asn Phe Leu Leu Glu Met
            405                 410                 415

Tyr Lys Val Glu Ser
            420

<210> SEQ ID NO 27
<211> LENGTH: 421
<212> TYPE: PRT
<213> ORGANISM: Tobamovirus/CRMV

<400> SEQUENCE: 27

Gly Ala Met Met Ser Ala Val Tyr Thr Gly Lys Ile Lys Val Gln Gln
1               5                   10                  15

Met Lys Asn Tyr Val Asp Tyr Leu Ser Ala Ser Leu Ser Ala Thr Val
            20                  25                  30

Ser Asn Leu Cys Lys Val Leu Arg Asp Val His Gly Val Asp Pro Glu
        35                  40                  45

Ser Gln Glu Lys Ser Gly Val Trp Asp Val Arg Arg Gly Arg Trp Leu
    50                  55                  60

Leu Lys Pro Asn Ala Lys Cys His Ala Trp Gly Val Ala Glu Asp Ala
65                  70                  75                  80

Asn His Lys Leu Val Ile Val Leu Leu Asn Trp Asp Glu Gly Lys Pro
                85                  90                  95

Val Cys Asp Glu Thr Trp Phe Arg Leu Ala Val Ser Ser Asp Ser Leu
            100                 105                 110

Val Tyr Ser Asp Met Gly Lys Leu Lys Thr Leu Thr Ser Cys Cys Arg
        115                 120                 125

Asp Gly Glu Pro Pro Glu Pro Thr Ala Lys Leu Val Leu Val Asp Gly
    130                 135                 140

Val Pro Gly Cys Gly Lys Thr Lys Glu Ile Leu Glu Lys Val Asn Phe
145                 150                 155                 160

Ser Glu Asp Leu Val Leu Val Pro Gly Lys Glu Ala Ser Lys Met Ile
                165                 170                 175

Ile Arg Arg Ala Asn Gln Ala Gly Ile Thr Arg Ala Asp Lys Asp Asn
            180                 185                 190

Val Arg Thr Val Asp Ser Phe Leu Met His Pro Pro Lys Arg Val Phe
        195                 200                 205

Lys Arg Leu Phe Ile Asp Glu Gly Leu Met Leu His Thr Gly Cys Val
    210                 215                 220

Asn Phe Leu Met Leu Leu Ser His Cys Asp Val Ala Tyr Val Tyr Val
225                 230                 235                 240

Asp Thr Gln Gln Ile Pro Phe Ile Cys Arg Val Ala Asn Phe Pro Tyr
                245                 250                 255
```

```
Pro Ala His Phe Ala Lys Leu Val Val Asp Glu Lys Glu Asp Arg Arg
            260                 265                 270

Val Thr Leu Arg Cys Pro Ala Asp Val Thr Tyr Phe Leu Asn Gln Lys
            275                 280                 285

Tyr Asp Gly Ser Val Leu Cys Thr Ser Ser Val Glu Arg Ser Val Ser
            290                 295                 300

Ala Glu Val Val Arg Gly Lys Gly Ala Leu Asn Pro Ile Thr Leu Pro
305                 310                 315                 320

Leu Glu Gly Lys Ile Leu Thr Phe Thr Gln Ala Asp Lys Phe Glu Leu
            325                 330                 335

Leu Asp Lys Gly Tyr Lys Asp Val Asn Thr Val His Glu Val Gln Gly
            340                 345                 350

Glu Thr Tyr Glu Lys Thr Ala Ile Val Arg Leu Thr Ala Thr Pro Leu
            355                 360                 365

Glu Ile Ile Ser Arg Ala Ser Pro His Val Leu Val Ala Leu Thr Arg
            370                 375                 380

His Thr Thr Arg Cys Lys Tyr Tyr Thr Val Val Leu Asp Pro Met Val
385                 390                 395                 400

Asn Val Ile Ser Glu Leu Gly Lys Leu Ser Asn Phe Leu Leu Glu Met
            405                 410                 415

Tyr Lys Val Glu Ser
            420

<210> SEQ ID NO 28
<211> LENGTH: 421
<212> TYPE: PRT
<213> ORGANISM: Tobamovirus/T

```
                195                 200                 205
Lys Arg Leu Phe Ile Asp Glu Gly Leu Met Leu His Thr Gly Cys Val
    210                 215                 220
Asn Phe Leu Thr Leu Leu Ser His Cys Glu Val Ala Tyr Val Tyr Gly
225                 230                 235                 240
Asp Thr Gln Gln Ile Pro Phe Ile Cys Arg Val Ala Asn Phe Pro Tyr
                245                 250                 255
Pro Lys His Phe Ala Lys Leu Val Val Asp Glu Lys Glu Asp Arg Arg
                260                 265                 270
Val Thr Leu Arg Cys Pro Ala Asp Val Thr Phe Phe Leu Asn Lys Lys
            275                 280                 285
Tyr Asp Gly Ala Val Leu Cys Thr Ser Ser Val Glu Arg Ser Val Ser
        290                 295                 300
Ala Glu Val Val Arg Gly Lys Gly Ala Leu Asn Pro Ile Thr Leu Pro
305                 310                 315                 320
Leu Glu Gly Lys Ile Leu Thr Phe Thr Gln Ala Asp Lys Phe Glu Leu
                325                 330                 335
Leu Asp Lys Gly Tyr Lys Asp Val Asn Thr Val His Glu Val Gln Gly
            340                 345                 350
Glu Thr Tyr Glu Lys Thr Ala Ile Val Arg Leu Thr Ala Thr Pro Leu
        355                 360                 365
Glu Ile Ile Ser Arg Ala Ser Pro His Val Leu Val Ala Leu Thr Arg
    370                 375                 380
His Thr Arg Cys Lys Tyr Tyr Thr Val Val Leu Asp Pro Met Val
385                 390                 395                 400
Asn Val Ile Ser Glu Met Glu Lys Leu Ser Asn Phe Ile Leu Asp Met
                405                 410                 415
Tyr Lys Val Glu Ser
            420

<210> SEQ ID NO 29
<211> LENGTH: 420
<212> TYPE: PRT
<213> ORGANISM: Tobamovirus/CGMMV

<400> SEQUENCE: 29

Lys Thr Ile Thr Pro Val Val Tyr Thr Gly Thr Ile Arg Glu Arg Gln
1               5                   10                  15
Met Lys Asn Tyr Ile Asp Tyr Leu Ser Ala Ser Leu Gly Ser Thr Leu
            20                  25                  30
Gly Asn Leu Glu Arg Ile Val Arg Ser Asp Trp Asn Gly Thr Glu Glu
        35                  40                  45
Ser Met Gln Thr Phe Gly Leu Tyr Asp Cys Glu Lys Cys Lys Trp Leu
    50                  55                  60
Leu Leu Pro Ala Glu Lys Lys His Ala Trp Ala Val Val Leu Ala Ser
65                  70                  75                  80
Asp Asp Thr Thr Arg Ile Ile Phe Leu Ser Tyr Asp Glu Ser Gly Ser
                85                  90                  95
Pro Ile Ile Asp Lys Lys Asn Trp Lys Arg Phe Ala Val Cys Ser Glu
            100                 105                 110
Thr Lys Val Tyr Ser Val Ile Arg Ser Leu Glu Val Leu Asn Lys Glu
        115                 120                 125
Ala Ile Val Asp Pro Gly Val His Ile Thr Leu Val Asp Gly Val Pro
    130                 135                 140
```

```
Gly Cys Gly Lys Thr Ala Glu Ile Ile Ala Arg Val Asn Trp Lys Thr
145                 150                 155                 160

Asp Leu Val Leu Thr Pro Gly Arg Glu Ala Ala Met Ile Arg Arg
            165                 170                 175

Arg Ala Cys Ala Leu His Lys Ser Pro Val Ala Thr Asn Asp Asn Val
            180                 185                 190

Arg Thr Phe Asp Ser Phe Val Met Asn Arg Lys Ile Phe Lys Phe Asp
            195                 200                 205

Ala Val Tyr Val Asp Glu Gly Leu Met Val His Thr Gly Leu Leu Asn
            210                 215                 220

Phe Ala Leu Lys Ile Ser Gly Cys Lys Lys Ala Phe Val Phe Gly Asp
225                 230                 235                 240

Ala Lys Gln Ile Pro Phe Ile Asn Arg Val Met Asn Phe Asp Tyr Pro
            245                 250                 255

Lys Glu Leu Arg Thr Leu Ile Val Asp Asn Val Glu Arg Arg Tyr Val
            260                 265                 270

Thr His Arg Cys Pro Arg Asp Val Thr Ser Phe Leu Asn Thr Ile Tyr
            275                 280                 285

Lys Ala Ala Val Ala Thr Thr Ser Pro Val Val His Ser Val Lys Ala
            290                 295                 300

Ile Lys Val Ser Gly Ala Gly Ile Leu Arg Pro Glu Leu Thr Lys Ile
305                 310                 315                 320

Lys Gly Lys Ile Ile Thr Phe Thr Gln Ser Asp Lys Gln Ser Leu Ile
            325                 330                 335

Lys Ser Gly Tyr Asn Asp Val Asn Thr Val His Glu Ile Gln Gly Glu
            340                 345                 350

Thr Phe Glu Glu Thr Ala Val Arg Ala Thr Pro Thr Pro Ile Gly
            355                 360                 365

Leu Ile Ala Arg Asp Ser Pro His Val Leu Val Ala Leu Thr Arg His
            370                 375                 380

Thr Lys Ala Met Val Tyr Tyr Thr Val Phe Asp Ala Val Thr Ser
385                 390                 395                 400

Ile Ile Ala Asp Val Glu Lys Val Asp Gln Ser Ile Leu Thr Met Phe
            405                 410                 415

Ala Thr Thr Val
            420

<210> SEQ ID NO 30
<211> LENGTH: 420
<212> TYPE: PRT
<213> ORGANISM: Tobamovirus/CGMMV-W

<400> SEQUENCE: 30

Lys Thr Ile Thr Pro Val Val Tyr Thr Gly Thr Ile Arg Glu Arg Gln
1               5                   10                  15

Met Lys Asn Tyr Ile Asp Tyr Leu Ser Ala Ser Leu Gly Ser Thr Leu
            20                  25                  30

Gly Asn Leu Glu Arg Ile Val Arg Ser Asp Trp Asn Gly Thr Glu Glu
            35                  40                  45

Ser Met Gln Thr Phe Gly Leu Tyr Asp Cys Glu Lys Cys Lys Trp Leu
            50                  55                  60

Leu Leu Pro Ala Glu Lys Lys His Ala Trp Ala Val Val Leu Ala Ser
65                  70                  75                  80

Asp Asp Thr Thr Arg Ile Ile Phe Leu Ser Tyr Asp Glu Ser Gly Ser
            85                  90                  95
```

```
Pro Ile Ile Asp Lys Lys Asn Trp Lys Arg Phe Ala Val Cys Ser Glu
                100                 105                 110

Thr Lys Val Tyr Ser Val Ile Arg Ser Leu Glu Val Leu Asn Lys Glu
            115                 120                 125

Ala Ile Val Asp Pro Gly Val His Ile Thr Leu Val Asp Gly Val Pro
        130                 135                 140

Gly Cys Gly Lys Thr Ala Glu Ile Ile Ala Arg Val Asn Trp Lys Thr
145                 150                 155                 160

Asp Leu Val Leu Thr Pro Gly Arg Glu Ala Ala Met Ile Arg Arg
                165                 170                 175

Arg Ala Cys Ala Leu His Lys Ser Pro Val Ala Thr Asn Asp Asn Val
            180                 185                 190

Arg Thr Phe Asp Ser Phe Val Met Asn Arg Lys Ile Phe Lys Phe Asp
                195                 200                 205

Ala Val Tyr Val Asp Glu Gly Leu Met Val His Thr Gly Leu Leu Asn
        210                 215                 220

Phe Ala Leu Lys Ile Ser Gly Cys Lys Lys Ala Phe Val Phe Gly Asp
225                 230                 235                 240

Ala Lys Gln Ile Pro Phe Ile Asn Arg Val Met Asn Phe Asp Tyr Pro
                245                 250                 255

Lys Glu Leu Arg Thr Leu Ile Val Asp Asn Val Glu Arg Arg Tyr Val
            260                 265                 270

Thr His Arg Cys Pro Arg Asp Val Thr Ser Phe Leu Asn Thr Ile Tyr
                275                 280                 285

Lys Ala Ala Val Ala Thr Thr Ser Pro Val Val His Ser Val Lys Ala
        290                 295                 300

Ile Lys Val Ser Gly Ala Gly Ile Leu Arg Pro Glu Leu Thr Lys Ile
305                 310                 315                 320

Lys Gly Lys Ile Ile Thr Phe Thr Gln Ser Asp Lys Gln Ser Leu Ile
                325                 330                 335

Lys Ser Gly Tyr Asn Asp Val Asn Thr Val His Glu Ile Gln Gly Glu
            340                 345                 350

Thr Phe Glu Glu Thr Ala Val Val Arg Ala Thr Pro Thr Pro Ile Gly
                355                 360                 365

Leu Ile Ala Arg Asp Ser Pro His Val Leu Val Ala Leu Thr Arg His
        370                 375                 380

Thr Lys Ala Met Val Tyr Tyr Thr Val Val Phe Asp Ala Val Thr Ser
385                 390                 395                 400

Ile Ile Ala Asp Val Glu Lys Val Asp Gln Ser Ile Leu Thr Met Phe
                405                 410                 415

Ala Thr Thr Val
            420

<210> SEQ ID NO 31
<211> LENGTH: 419
<212> TYPE: PRT
<213> ORGANISM: Tobamovirus/CFMMV

<400> SEQUENCE: 31

Lys Thr Ile Thr Pro Val Ile Tyr Thr Gly Pro Ile Arg Val Arg Gln
1               5                   10                  15

Met Ala Asn Tyr Leu Asp Tyr Leu Ser Ala Asn Leu Ala Ala Thr Ile
            20                  25                  30

Gly Ile Leu Glu Arg Ile Val Arg Ser Asn Trp Ser Gly Asn Glu Val
```

```
                 35                  40                  45
Val Gln Thr Tyr Gly Leu Phe Asp Cys Gln Ala Asn Lys Trp Ile Leu
 50                  55                  60

Leu Pro Ser Glu Lys Thr His Ser Trp Gly Val Cys Leu Thr Met Asp
 65                  70                  75                  80

Asp Lys Leu Arg Val Leu Leu Gln Tyr Asp Ser Ala Gly Trp Pro
                 85                  90                  95

Ile Val Asp Lys Ser Phe Trp Lys Ala Phe Cys Val Cys Ala Asp Thr
                100                 105                 110

Lys Val Phe Ser Val Ile Arg Ser Leu Glu Val Leu Ser Ala Leu Pro
                115                 120                 125

Leu Val Glu Pro Asp Ala Lys Tyr Val Leu Ile Asp Gly Val Pro Gly
                130                 135                 140

Cys Gly Lys Thr Gln Glu Ile Ile Ser Ser Ala Asp Phe Lys Thr Asp
145                 150                 155                 160

Leu Ile Leu Thr Pro Gly Lys Glu Ala Ala Ala Met Ile Arg Arg Arg
                165                 170                 175

Ala Asn Met Lys Tyr Arg Ser Pro Val Ala Thr Asn Asp Asn Val Arg
                180                 185                 190

Thr Phe Asp Ser Phe Val Met Asn Lys Lys Pro Phe Thr Phe Lys Thr
                195                 200                 205

Leu Trp Val Asp Glu Gly Leu Met Val His Thr Gly Leu Leu Asn Phe
                210                 215                 220

Cys Val Asn Ile Ala Lys Val Lys Glu Val Arg Ile Phe Gly Asp Thr
225                 230                 235                 240

Lys Gln Ile Pro Phe Ile Asn Arg Val Met Asn Phe Asp Tyr Pro Leu
                245                 250                 255

Glu Leu Arg Lys Ile Ile Val Asp Thr Val Glu Lys Arg Tyr Thr Ser
                260                 265                 270

Lys Arg Cys Pro Arg Asp Val Thr His Tyr Leu Asn Glu Val Tyr Ser
                275                 280                 285

Ser Pro Val Cys Thr Thr Ser Pro Val Val His Ser Val Thr Thr Lys
                290                 295                 300

Lys Ile Ala Gly Val Gly Leu Leu Arg Pro Glu Leu Thr Ala Leu Pro
305                 310                 315                 320

Gly Lys Ile Ile Thr Phe Thr Gln Asn Asp Lys Gln Thr Leu Leu Lys
                325                 330                 335

Ala Gly Tyr Ala Asp Val Asn Thr Val His Glu Val Gln Gly Glu Thr
                340                 345                 350

Tyr Glu Glu Thr Ser Val Val Arg Ala Thr Ala Thr Pro Ile Gly Leu
                355                 360                 365

Ile Ser Arg Lys Ser Pro His Val Leu Val Ala Leu Ser Arg His Thr
                370                 375                 380

Lys Ala Met Thr Tyr Tyr Thr Val Thr Val Asp Pro Val Ser Cys Ile
385                 390                 395                 400

Ile Ala Asp Leu Glu Lys Val Asp Gln Ser Ile Leu Ser Met Tyr Ala
                405                 410                 415

Ser Val Ala

<210> SEQ ID NO 32
<211> LENGTH: 420
<212> TYPE: PRT
<213> ORGANISM: Tobamovirus/YCGMMV
```

<400> SEQUENCE: 32

```
Lys Ser Ile Thr Pro Val Ile Tyr Thr Gly Pro Ile Arg Val Arg Gln
1               5                   10                  15

Met Ala Asn Tyr Leu Asp Tyr Leu Ser Ala Ser Leu Thr Ala Thr Ile
            20                  25                  30

Gly Asn Leu Glu Arg Ile Val Ser Ser Trp Thr Gly Glu Asn Glu
        35                  40                  45

Leu Val Gln Thr Tyr Gly Leu Phe Asp Cys Gln Ala Asp Lys Trp Ile
    50                  55                  60

Leu Gln Pro Thr Glu Arg Thr His Ser Trp Gly Val Cys Leu Thr Met
65                  70                  75                  80

Asp Asp Lys Leu Arg Ile Val Leu Leu Gln Tyr Asp Glu Phe Asp Trp
                85                  90                  95

Pro Ile Val Asp Lys Ser Ser Trp Lys Ala Phe Cys Val Ser Ala Asp
            100                 105                 110

Thr Lys Val Phe Ser Ile Ile Arg Ser Leu Glu Val Leu Ser Ser Leu
        115                 120                 125

Pro Leu Ser Asp Pro Thr Ala Lys Phe Thr Leu Ile Asp Gly Val Pro
    130                 135                 140

Gly Cys Gly Lys Thr Gln Glu Ile Ile Asn Ser Ala Asp Phe Lys Thr
145                 150                 155                 160

Asp Leu Ile Leu Thr Pro Gly Lys Glu Ser Ala Ala Met Ile Arg Arg
                165                 170                 175

Arg Ala Asn Ala Lys Phe Arg Gly Cys Val Ala Thr Asn Asp Asn Val
            180                 185                 190

Arg Thr Phe Asp Ser Phe Val Met Asn Lys Lys Pro Phe Thr Phe Lys
        195                 200                 205

Thr Leu Trp Val Asp Glu Gly Leu Met Val His Thr Gly Leu Leu Asn
    210                 215                 220

Phe Cys Val Asn Ile Ala Lys Val Lys Glu Val Lys Ile Phe Gly Asp
225                 230                 235                 240

Thr Lys Gln Ile Pro Phe Ile Asn Arg Val Met Asn Phe Asp Tyr Pro
                245                 250                 255

Leu Glu Leu Lys Lys Ile Ile Val Asp Asp Val Glu Lys Arg Tyr Thr
            260                 265                 270

Ser Lys Arg Cys Pro Arg Asp Val Thr His Tyr Leu Asn Glu Val Tyr
        275                 280                 285

Ala Ala Pro Val Thr Thr Ser Ser Ala Val Val His Ser Val Ser Gln
    290                 295                 300

Lys Lys Ile Ala Gly Val Gly Leu Leu Arg Pro Glu Leu Thr Ser Leu
305                 310                 315                 320

Glu Gly Lys Ile Ile Thr Phe Thr Gln Ser Asp Lys Gln Thr Leu Leu
                325                 330                 335

Lys Ala Gly Tyr Glu Asp Val Asn Thr Val His Glu Val Gln Gly Glu
            340                 345                 350

Thr Tyr Glu Cys Thr Ser Val Val Arg Ala Thr Ala Thr Pro Ile Gly
        355                 360                 365

Leu Ile Ser Arg Lys Ser Pro His Val Leu Val Ala Leu Ser Arg His
    370                 375                 380

Thr Lys Thr Met Thr Tyr Tyr Thr Val Thr Val Asp Pro Val Ser Cys
385                 390                 395                 400

Ile Ile Ala Asp Leu Glu Lys Val Asp Gln Ser Ile Leu Ser Met Tyr
                405                 410                 415
```

Ala Thr Val Ala
        420

<210> SEQ ID NO 33
<211> LENGTH: 419
<212> TYPE: PRT
<213> ORGANISM: Tobamovirus/SHMV

<400> SEQUENCE: 33

Gln Lys Pro Val Asn Ile Val Tyr Thr Gly Glu Val Gln Ile Cys Gln
1               5                   10                  15

Met Gln Asn Tyr Leu Asp Tyr Leu Ser Ala Ser Leu Val Ala Cys Ile
            20                  25                  30

Ser Asn Leu Lys Lys Tyr Leu Gln Asp Gln Trp Leu Asn Pro Gly Glu
        35                  40                  45

Lys Phe Gln Lys Ile Gly Val Trp Asp Asn Leu Asn Asn Lys Trp Ile
    50                  55                  60

Val Val Pro Gln Lys Lys Tyr Ala Trp Gly Leu Ala Ala Asp Val
65                  70                  75                  80

Asp Gly Asn Gln Lys Thr Val Ile Leu Asn Tyr Asp Glu His Gly Met
                85                  90                  95

Pro Ile Leu Glu Lys Ser Tyr Val Arg Leu Val Val Ser Thr Asp Thr
            100                 105                 110

Tyr Leu Phe Thr Val Val Ser Met Leu Gly Tyr Leu Arg His Leu Asp
        115                 120                 125

Gln Lys Lys Pro Thr Ala Thr Ile Thr Leu Val Asp Gly Val Pro Gly
    130                 135                 140

Cys Gly Lys Thr Gln Glu Ile Leu Ser Arg Phe Asp Ala Asn Ser Asp
145                 150                 155                 160

Leu Ile Leu Val Gln Gly Arg Glu Ala Cys Glu Met Ile Arg Arg Arg
                165                 170                 175

Ala Asn Asp Asn Val Pro Gly Ser Ala Thr Lys Glu Asn Val Arg Thr
            180                 185                 190

Phe Asp Ser Phe Val Met Asn Arg Lys Pro Gly Lys Phe Lys Thr Leu
        195                 200                 205

Trp Val Asp Glu Gly Leu Met Val His Pro Gly Leu Ile Asn Phe Cys
    210                 215                 220

Ile Asn Ile Ser Cys Val Ser Ser Val Tyr Ile Phe Gly Asp Arg Lys
225                 230                 235                 240

Gln Ile Pro Phe Ile Asn Arg Val Met Asn Phe Ser Ile Pro Asp Asn
                245                 250                 255

Leu Ala Lys Leu Tyr Tyr Asp Glu Ile Val Ser Arg Asp Thr Thr Lys
            260                 265                 270

Arg Cys Pro Leu Asp Val Thr His Phe Leu Asn Ser Val Tyr Glu Lys
        275                 280                 285

Arg Val Met Ser Tyr Ser Asn Val Gln Arg Ser Leu Glu Cys Lys Met
    290                 295                 300

Ile Ser Gly Lys Ala Lys Ile Asn Asp Tyr Arg Ser Ile Leu Ala Glu
305                 310                 315                 320

Gly Lys Leu Leu Thr Phe Thr Gln Glu Asp Lys Glu Tyr Leu Leu Lys
                325                 330                 335

Ala Gly Phe Lys Asp Val Asn Thr Val His Glu Ala Gln Gly Glu Thr
            340                 345                 350

Tyr Arg Asp Val Asn Leu Ile Arg Val Thr Ala Thr Pro Leu Thr Ile

-continued

```
                355                 360                 365
Val Ser Ala Gly Ser Pro His Val Thr Val Ala Leu Ser Arg His Thr
        370                 375                 380

Asn Arg Phe Val Tyr Tyr Thr Val Val Pro Asp Val Val Met Thr Thr
385                 390                 395                 400

Val Gln Lys Thr Gln Cys Val Ser Asn Phe Leu Leu Asp Met Tyr Ala
                405                 410                 415

Val Ala Tyr

<210> SEQ ID NO 34
<211> LENGTH: 468
<212> TYPE: PRT
<213> ORGANISM: Tobamovirus/TMV-vul

<400> SEQUENCE: 34

Met Gln Phe Tyr Tyr Asp Lys Cys Leu Pro Gly Asn Ser Thr Met Met
1               5                   10                  15

Asn Asn Phe Asp Ala Val Thr Met Arg Leu Thr Asp Ile Ser Leu Asn
                20                  25                  30

Val Lys Asp Cys Ile Leu Asp Met Ser Lys Ser Val Ala Ala Pro Lys
            35                  40                  45

Asp Gln Ile Lys Pro Leu Ile Pro Met Val Arg Thr Ala Ala Gl

```
                305                 310                 315                 320

Ala Ser Met Leu Pro Met Glu Lys Ile Ile Lys Gly Ala Phe Cys Gly
                325                 330                 335

Asp Asp Ser Leu Leu Tyr Phe Pro Lys Gly Cys Glu Phe Pro Asp Val
                340                 345                 350

Gln His Ser Ala Asn Leu Met Trp Asn Phe Glu Ala Lys Leu Phe Lys
                355                 360                 365

Lys Gln Tyr Gly Tyr Phe Cys Gly Arg Tyr Val Ile His His Asp Arg
                370                 375                 380

Gly Cys Ile Val Tyr Tyr Asp Pro Leu Lys Leu Ile Ser Lys Leu Gly
385                 390                 395                 400

Ala Lys His Ile Lys Asp Trp Glu His Leu Glu Glu Phe Arg Arg Ser
                405                 410                 415

Leu Cys Asp Val Ala Val Ser Leu Asn Asn Cys Ala Tyr Tyr Thr Gln
                420                 425                 430

Leu Asp Asp Ala Val Trp Glu Val His Lys Thr Ala Pro Pro Gly Ser
                435                 440                 445

Phe Val Tyr Lys Ser Leu Val Lys Tyr Leu Ser Asp Lys Val Leu Phe
                450                 455                 460

Arg Ser Leu Phe
465

<210> SEQ ID NO 35
<211> LENGTH: 468
<212> TYPE: PRT
<213> ORGANISM: Tobamovirus/TMV-Rak

<400> SEQUENCE: 35

Met Gln Phe Tyr Tyr Asp Lys Cys Leu Pro Gly Asn Ser Thr Met Met
1               5                   10                  15

Asn Asn Phe Asp Ala Val Thr Met Arg Leu Thr Asp Ile Ser Leu Asn
                20                  25                  30

Val

```
Val Asp Ser Ser Arg Phe Leu Phe Thr Arg Lys Thr Pro Ala Gln
    210                 215                 220

Ile Glu Asp Phe Phe Gly Asp Leu Asp Ser His Val Pro Met Asp Val
225                 230                 235                 240

Leu Glu Leu Asp Ile Ser Lys Tyr Asp Lys Ser Gln Asn Glu Phe His
                245                 250                 255

Cys Ala Val Glu Tyr Glu Ile Trp Arg Arg Leu Gly Phe Glu Asp Phe
            260                 265                 270

Leu Gly Glu Val Trp Lys Gln Gly His Arg Lys Thr Thr Leu Lys Asp
        275                 280                 285

Tyr Thr Ala Gly Ile Lys Thr Cys Ile Trp Tyr Gln Arg Lys Ser Gly
    290                 295                 300

Asp Val Thr Thr Phe Ile Gly Asn Thr Val Ile Ile Ala Ala Cys Leu
305                 310                 315                 320

Ala Ser Met Leu Arg Met Glu Lys Ile Ile Lys Gly Ala Phe Cys Gly
                325                 330                 335

Asp Asp Ser Leu Leu Tyr Phe Pro Lys Gly Cys Glu Phe Pro Asp Ile
            340                 345                 350

Gln His Ser Val Asn Leu Met Trp Asn Phe Glu Ala Lys Leu Phe Lys
        355                 360                 365

Lys Gln Tyr Gly Tyr Phe Cys Gly Arg Tyr Ile Ile His His Asp Arg
    370                 375                 380

Gly Cys Ile Val Tyr Tyr Asp Pro Leu Lys Leu Ile Ser Lys Leu Gly
385                 390                 395                 400

Ala Lys His Ile Lys Asp Trp Glu His Leu Glu Glu Phe Arg Arg Ser
                405                 410                 415

Leu Cys Asp Val Ala Val Ser Leu Asn Asn Cys Ala Tyr Tyr Thr Gln
            420                 425                 430

Leu Asp Asp Ala Val Trp Glu Val His Lys Thr Ala Pro Pro Gly Ser
        435                 440                 445

Phe Val Tyr Lys Ser Leu Val Lys Tyr Leu Ser Asp Lys Val Leu Phe
    450                 455                 460

Arg Ser Leu Phe
465

<210> SEQ ID NO 36
<211> LENGTH: 468
<212> TYPE: PRT
<213> ORGANISM: Tobamovirus/TMV-WAN Lys Arg Lys Pro Asn Lys Asn Val Ser Leu Phe Ser Arg Glu Ser Leu
            115                 120                 125

Asn Arg Trp Le

-continued

```
1               5                   10                  15
Asn Asn Tyr Asp Ala Val Thr Met Lys Leu Thr Asp Ile Ser Leu Asn
                20                  25                  30
Val Lys Asp Cys Ile Leu Asp Met Ser Lys Ser Val Ala Ala Pro Lys
                35                  40                  45
Asp Val Lys Pro Thr Leu Ile Pro Met Val Arg Thr Ala Ala Glu Met
                50                  55                  60
Pro Arg Gln Thr Gly Leu Leu Glu Asn Leu Val Ala Met Ile Lys Arg
 65                 70                  75                  80
Asn Phe Asn Ser Pro Glu Leu Ser Gly Val Val Asp Ile Glu Asn Thr
                85                  90                  95
Ala Ser Leu Val Val Asp Lys Phe Phe Asp Ser Tyr Leu Leu Lys Glu
                100                 105                 110
Lys Arg Lys Pro Asn Lys Asn Phe Ser Leu Phe Ser Arg Glu Ser Leu
                115                 120                 125
Asn Arg Trp Ile Ala Lys Gln Glu Gln Val Thr Ile Gly Gln Leu Ala
                130                 135                 140
Asp Phe Asp Phe Val Asp Leu Pro Ala Val Asp Gln Tyr Arg His Met
145                 150                 155                 160
Ile Lys Ala Gln Pro Lys Gln Lys Leu Asp Leu Ser Ile Gln Thr Glu
                165                 170                 175
Tyr Pro Ala Leu Gln Thr Ile Val Tyr His Ser Lys Lys Ile Asn Ala
                180                 185                 190
Ile Phe Gly Pro Leu Phe Ser Glu Leu Thr Arg Gln Leu Leu Asp Ser
                195                 200                 205
Ile Asp Ser Ser Arg Phe Leu Phe Thr Arg Lys Thr Pro Ala Gln
                210                 215                 220
Ile Glu Asp Phe Phe Gly Asp Leu Asp Ser His Val Pro Met Asp Val
225                 230                 235                 240
Leu Glu Leu Asp Val Ser Lys Tyr Asp Lys Ser Gln Asn Glu Phe His
                245                 250                 255
Cys Ala Val Glu Tyr Glu Ile Trp Arg Arg Leu Gly Leu Glu Asp Phe
                260                 265                 270
Leu Ala Glu Val Trp Lys Gln Gly His Arg Lys Thr Thr Leu Lys Asp
                275                 280                 285
Tyr Thr Ala Gly Ile Lys Thr Cys Leu Trp Tyr Gln Arg Lys Ser Gly
                290                 295                 300
Asp Val Thr Thr Phe Ile Gly Asn Thr Val Ile Ala Ser Cys Leu
305                 310                 315                 320
Ala Ser Met Leu Pro Met Glu Lys Leu Ile Lys Gly Ala Phe Cys Gly
                325                 330                 335
Asp Asp Ser Leu Leu Tyr Phe Pro Lys Gly Cys Glu Tyr Pro Asp Ile
                340                 345                 350
Gln Gln Ala Ala Asn Leu Met Trp Asn Phe Glu Ala Lys Leu Phe Lys
                355                 360                 365
Lys Gln Tyr Gly Tyr Phe Cys Gly Arg Tyr Val Ile His His Asp Arg
                370                 375                 380
Gly Cys Ile Val Tyr Tyr Asp Pro Leu Lys Leu Ile Ser Lys Leu Gly
385                 390                 395                 400
Ala Lys His Ile Lys Asp Trp Asp His Leu Glu Glu Phe Arg Arg Ser
                405                 410                 415
Leu Cys Asp Val Ala Glu Ser Leu Asn Asn Cys Ala Tyr Tyr Thr Gln
                420                 425                 430
```

```
Leu Asp Asp Ala Val Gly Glu Val His Lys Thr Ala Pro Pro Gly Ser
            435                 440                 445

Phe Val Tyr Lys Ser Leu Val Lys Tyr Leu Ser Asp Lys Val Leu Phe
            450                 455                 460

Arg Ser Leu Phe
465

<210> SEQ ID NO 38
<211> LENGTH: 467
<212> TYPE: PRT
<213> ORGANISM: Tobamovirus/TMV-KR

<400> SEQUENCE: 38

Met Gln Tyr Tyr Asp Lys Cys Leu Pro Gly Asn Ser Thr Ile Leu
1               5                   10                  15

Asn Glu Tyr Asp Ala Val Thr Met Gln Ile Arg Glu Asn Ser Leu Asn
                20                  25                  30

Val Lys Asp Cys Val Leu Asp Met Ser Lys Ser Val Pro Leu Pro Arg
            35                  40                  45

Glu Ser Glu Thr Thr Leu Lys Pro Val Ile Arg Thr Ala Ala Glu Lys
        50                  55                  60

Pro Arg Lys Pro Gly Leu Leu Glu Asn Leu Val Ala Met Ile Lys Arg
65                  70                  75                  80

Asn Phe Asn Ser Pro Glu Leu Val Gly Val Val Asp Ile Glu Asp Thr
                85                  90                  95

Ala Ser Leu Val Val Asp Lys Phe Phe Asp Ala Tyr Leu Ile Lys Glu
            100                 105                 110

Lys Lys Lys Pro Lys Asn Ile Pro Leu Leu Ser Arg Ala Ser Leu Glu
        115                 120                 125

Arg Trp Ile Glu Lys Gln Glu Lys Ser Thr Ile Gly Gln Leu Ala Asp
130                 135                 140

Phe Asp Phe Ile Asp Leu Pro Ala Val Asp Gln Tyr Arg His Met Ile
145                 150                 155                 160

Lys Gln Gln Pro Lys Gln Arg Leu Asp Leu Ser Ile Gln Thr Glu Tyr
                165                 170                 175

Pro Ala Leu Gln Thr Ile Val Tyr His Ser Lys Lys Ile Asn Ala Leu
            180                 185                 190

Phe Gly Pro Val Phe Ser Glu Leu Thr Arg Gln Leu Leu Glu Thr Ile
        195                 200                 205

Asp Ser Ser Arg Phe Met Phe Tyr Thr Arg Lys Thr Pro Thr Gln Ile
210                 215                 220

Glu Glu Phe Phe Ser Asp Leu Asp Ser Asn Val Pro Met Asp Ile Leu
225                 230                 235                 240

Glu Leu Asp Ile Ser Lys Tyr Asp Lys Ser Gln Asn Glu Phe His Cys
                245                 250                 255

Ala Val Glu Tyr Glu Ile Trp Lys Arg Leu Gly Leu Asp Asp Phe Leu
            260                 265                 270

Ala Glu Val Trp Lys His Gly His Arg Lys Thr Thr Leu Lys Asp Tyr
        275                 280                 285

Thr Ala Gly Ile Lys Thr Cys Leu Trp Tyr Gln Arg Lys Ser Gly Asp
290                 295                 300

Val Thr Thr Phe Ile Gly Asn Thr Ile Ile Ala Ala Cys Leu Ser
305                 310                 315                 320

Ser Met Leu Pro Met Glu Arg Leu Ile Lys Gly Ala Phe Cys Gly Asp
```

-continued

```
                325                 330                 335

Asp Ser Ile Leu Tyr Phe Pro Lys Gly Thr Asp Phe Pro Asp Ile Gln
            340                 345                 350

Gln Gly Ala Asn Leu Leu Trp Asn Phe Glu Ala Lys Leu Phe Arg Lys
        355                 360                 365

Arg Tyr Gly Tyr Phe Cys Gly Arg Tyr Ile Ile His His Asp Arg Gly
    370                 375                 380

Cys Ile Val Tyr Tyr Asp Pro Leu Lys Leu Ile Ser Lys Leu Gly Ala
385                 390                 395                 400

Lys His Ile Lys Asn Arg Glu His Leu Glu Glu Phe Arg Thr Ser Leu
                405                 410                 415

Cys Asp Val Ala Gly Ser Leu Asn Asn Cys Ala Tyr Tyr Thr His Leu
            420                 425                 430

Asn Asp Ala Val Gly Glu Val Ile Lys Thr Ala Pro Leu Gly Ser Phe
        435                 440                 445

Val Tyr Arg Ala Leu Val Lys Tyr Leu Cys Asp Lys Arg Leu Phe Gln
    450                 455                 460

Thr Leu Phe
465

<210> SEQ ID NO 39
<211> LENGTH: 470
<212> TYPE: PRT
<213> ORGANISM: Tobamovirus/PMMV

<400> SEQUENCE: 39

Pro Asp Leu Gln Phe Tyr Tyr Asp Val Cys Leu Pro Gly Asn Ser Thr
1               5                   10                  15

Ile Leu Asn Lys Tyr Asp Ala Val Thr Met Arg Leu Arg Asp Asn Ser
            20                  25                  30

Leu Asn Val Lys Asp Cys Val Leu Asp Phe Ser Lys Ser Ile Pro Met
        35                  40                  45

Pro Lys Glu Val Lys Pro Cys Leu Glu Pro Val Leu Arg Thr Ala Ala
    50                  55                  60

Glu Pro Pro Arg Ala Ala Gly Leu Leu Glu Asn Leu Val Ala Met Ile
65                  70                  75                  80

Lys Arg Asn Phe Asn Ala Pro Asp Leu Thr Gly Thr Ile Asp Ile Glu
                85                  90                  95

Ser Thr Ala Ser Val Val Val Asp Lys Phe Phe Asp Ser Tyr Phe Ile
            100                 105                 110

Lys Lys Glu Lys Tyr Thr Lys Asn Ile Ala Gly Val Met Thr Lys Asp
        115                 120                 125

Ser Met Met Arg Trp Leu Glu Asn Arg Lys Glu Val Leu Leu Asp Asp
    130                 135                 140

Leu Ala Asn Tyr Asn Phe Thr Asp Leu Pro Ala Ile Asp Gln Tyr Lys
145                 150                 155                 160

His Met Ile Lys Ala Gln Pro Lys Gln Lys Leu Asp Leu Ser Ile Gln
                165                 170                 175

Asn Glu Tyr Pro Ala Leu Gln Thr Ile Val Tyr His Ser Lys Gln Ile
            180                 185                 190

Asn Gly Ile Leu Ala Gly Phe Ser Glu Leu Thr Arg Leu Leu Leu Glu
        195                 200                 205

Ala Phe Asp Ser Lys Lys Phe Leu Phe Phe Thr Arg Lys Thr Pro Glu
    210                 215                 220
```

-continued

```
Gln Ile Gln Glu Phe Phe Ser Asp Leu Asp Ser His Val Pro Met Asp
225                 230                 235                 240

Val Leu Glu Leu Asp Ile Ser Lys Tyr Asp Lys Ser Gln Asn Glu Phe
                245                 250                 255

His Cys Ala Val Glu Tyr Glu Ile Trp Lys Arg Leu Gly Leu Asn Glu
            260                 265                 270

Phe Leu Ala Glu Val Trp Lys Gln Gly His Arg Lys Thr Thr Leu Lys
        275                 280                 285

Asp Tyr Ile Ala Gly Ile Lys Thr Cys Leu Trp Tyr Gln Arg Lys Ser
    290                 295                 300

Gly Asp Val Thr Thr Phe Ile Gly Asn Thr Val Ile Ile Ala Ala Cys
305                 310                 315                 320

Leu Gly Ser Met Leu Pro Met Glu Lys Val Ile Lys Gly Ala Phe Cys
                325                 330                 335

Gly Asp Asp Ser Val Leu Tyr Phe Pro Lys Gly Leu Asp Phe Pro Asp
            340                 345                 350

Ile Gln Ser Cys Ala Asn Leu Met Trp Asn Phe Glu Ala Lys Leu Tyr
        355                 360                 365

Arg Lys Arg Tyr Gly Tyr Phe Cys Gly Arg Tyr Ile Ile His His Asp
    370                 375                 380

Lys Gly Ala Ile Val Tyr Tyr Asp Pro Leu Lys Leu Ile Ser Lys Leu
385                 390                 395                 400

Gly Ala Lys His Ile Lys Asp Tyr Asp His Leu Glu Glu Leu Arg Val
                405                 410                 415

Ser Leu Cys Asp Val Ala Cys Ser Leu Gly Asn Trp Cys Leu Gly Phe
            420                 425                 430

Pro Gln Leu Asn Ala Ala Ile Lys Glu Val His Lys Thr Ala Ile Asp
        435                 440                 445

Gly Ser Phe Ala Phe Asn Cys Val Asn Lys Phe Leu Cys Asp Lys Phe
    450                 455                 460

Leu Phe Arg Thr Leu Phe
465                 470

<210> SEQ ID NO 40
<211> LENGTH: 458
<212> TYPE: PRT
<213> ORGANISM: Tobamovirus/TMGMV

<400> SEQUENCE: 40

Met Gln Phe Tyr Tyr Asp Thr Leu Leu Pro Gly Asn Ser Thr Ile Leu
1               5                   10                  15

Asn Glu Tyr Asp Ala Val Thr Met Asn Leu Arg Glu Asn Asn Leu Asn
            20                  25                  30

Val Lys Asp Cys Thr Ile Asp Phe Ser Lys Ser Val Ser Val Pro Arg
        35                  40                  45

Gln Gln Glu Glu Phe Phe Thr Pro Val Ile Arg Thr Ala Ala Glu Arg
    50                  55                  60

Pro Arg Ser Ala Gly Leu Leu Glu Asn Leu Val Ala Met Ile Lys Arg
65                  70                  75                  80

Asn Phe Asn Ser Pro Asp Leu Thr Gly Ile Leu Asp Ile Glu Asp Thr
                85                  90                  95

Ala Glu Leu Val Val Asn Lys Phe Trp Asp Ala Tyr Ile Ile Asp Glu
            100                 105                 110

Leu Ser Gly Gly Asn Val Thr Pro Met Thr Ser Asp Ala Phe His Arg
        115                 120                 125
```

-continued

Trp Met Ala Lys Gln Glu Lys Ser Thr Ile Arg Gln Leu Ala Asp Phe
    130                 135                 140

Asp Phe Val Asp Leu Pro Ala Ile Asp Gln Tyr Lys His Met Ile Lys
145                 150                 155                 160

Ala Gln Pro Lys Gln Lys Leu Asp Leu Ser Pro Gln Asp Glu Tyr Ala
                165                 170                 175

Ala Leu Gln Thr Ile Val Tyr His Ser Lys Gln Ile Asn Ala Ile Phe
            180                 185                 190

Gly Pro Leu Phe Ala Glu Leu Thr Arg Gln Leu Leu Glu Arg Ile Asp
        195                 200                 205

Ser Ser Lys Phe Leu Phe Tyr Thr Arg Lys Thr Pro Glu Gln Ile Glu
    210                 215                 220

Glu Phe Leu Ser Asp Leu Asp Ser Thr Val Pro Met Glu Ala Leu Val
225                 230                 235                 240

Leu Asp Ile Ser Lys Tyr Asp Lys Ser Gln Asn Glu Phe His Cys Ala
                245                 250                 255

Val Glu Tyr Phe Ile Trp Glu Lys Leu Gly Leu Asn Gly Phe Leu Glu
            260                 265                 270

Glu Val Trp Lys Gln Gly His Arg Lys Thr Ser Leu Lys Asp Tyr Thr
        275                 280                 285

Ala Gly Ile Lys Thr Cys Leu Trp Tyr Gln Arg Lys Ser Gly Asp Val
    290                 295                 300

Thr Thr Phe Ile Gly Asn Thr Val Ile Ile Ala Ala Cys Leu Ala Ser
305                 310                 315                 320

Met Ile Pro Met Asp Lys Val Ile Lys Ala Ala Phe Cys Gly Asp Asp
                325                 330                 335

Ser Ile Leu Asp Ile Pro Lys Gly Leu Asp Leu Pro Asp Ile Gln Ser
            340                 345                 350

Glu Ala Asn Leu Met Trp Asn Phe Glu Ala Lys Leu Tyr Arg Lys Arg
        355                 360                 365

Tyr Gly Tyr Phe Cys Ala Arg Tyr Ile Ile His His Asp Arg Gly Ala
    370                 375                 380

Ile Val Tyr Tyr Asp Pro Leu Lys Leu Ile Ser Lys Leu Gly Cys Lys
385                 390                 395                 400

His Ile Lys Ser Leu Asp His Leu Glu Glu Phe Arg Met Ser Leu Cys
                405                 410                 415

Asp Val Ser Ser Ser Leu Asn Asn Cys Ala Leu Phe Gly Gln Leu Asn
            420                 425                 430

Asp Ala Ile Ala Glu Val His Lys Thr Ala Val Asn Gly Ser Phe Ala
        435                 440                 445

Phe Cys Ser Ile Val Lys Tyr Leu Ser Asp
    450                 455

<210> SEQ ID NO 41
<211> LENGTH: 466
<212> TYPE: PRT
<213> ORGANISM: Tobamovirus/ORSV

<400> SEQUENCE: 41

Met Gln Phe Tyr Tyr Asp Ala Leu Leu Pro Gly Asn Ser Thr Ile Leu
1               5                   10                  15

Asn Glu Phe Asp Ala Val Thr Met Asn Leu Arg Asp Ile Ser Leu Asn
            20                  25                  30

Val Lys Asp Cys Arg Ile Asp Phe Ser Lys Ser Val Gln Leu Pro Lys

```
                35                  40                  45
Glu Gln Pro Ile Phe Leu Lys Pro Lys Ile Arg Thr Ala Ala Glu Met
 50                  55                  60

Pro Arg Thr Ala Gly Leu Leu Glu Asn Leu Val Ala Met Ile Lys Arg
 65                  70                  75                  80

Asn Met Asn Ala Pro Asp Leu Thr Gly Thr Ile Asp Ile Glu Asp Thr
                 85                  90                  95

Ala Ser Leu Val Val Glu Lys Phe Trp Asp Ser Tyr Val Asp Lys Glu
                100                 105                 110

Phe Ser Gly Thr Asn Glu Met Thr Met Thr Arg Glu Ser Phe Ser Arg
                115                 120                 125

Trp Leu Ser Lys Gln Glu Ser Ser Thr Val Gly Gln Leu Ala Asp Phe
130                 135                 140

Asn Phe Val Asp Leu Pro Ala Val Asp Glu Tyr Lys His Met Ile Lys
145                 150                 155                 160

Ser Gln Pro Lys Gln Lys Leu Asp Leu Ser Ile Gln Asp Glu Tyr Pro
                165                 170                 175

Ala Leu Gln Thr Ile Val Tyr His Ser Lys Lys Ile Asn Ala Ile Phe
                180                 185                 190

Gly Pro Met Phe Ser Glu Leu Thr Arg Met Leu Leu Glu Arg Ile Asp
                195                 200                 205

Ser Ser Lys Phe Leu Phe Tyr Thr Arg Lys Thr Pro Ala Gln Ile Glu
210                 215                 220

Asp Phe Phe Ser Asp Leu Asp Ser Thr Gln Ala Met Glu Ile Leu Glu
225                 230                 235                 240

Leu Asp Ile Ser Lys Tyr Asp Lys Ser Gln Asn Glu Phe His Cys Ala
                245                 250                 255

Val Glu Tyr Lys Ile Trp Glu Lys Leu Gly Ile Asp Glu Trp Leu Ala
                260                 265                 270

Glu Val Trp Lys Gln Gly His Arg Lys Thr Thr Leu Lys Asp Tyr Thr
                275                 280                 285

Ala Gly Val Lys Thr Cys Leu Trp Tyr Gln Arg Lys Ser Gly Asp Val
290                 295                 300

Thr Thr Phe Ile Gly Asn Thr Ile Ile Ala Ala Cys Leu Ser Ser
305                 310                 315                 320

Met Ile Pro Met Asp Lys Val Ile Lys Ala Ala Phe Cys Gly Asp Asp
                325                 330                 335

Ser Leu Ile Tyr Ile Pro Lys Gly Leu Asp Leu Pro Asp Ile Gln Ala
                340                 345                 350

Gly Ala Asn Leu Met Trp Asn Phe Glu Ala Lys Leu Phe Arg Lys Lys
                355                 360                 365

Tyr Gly Tyr Phe Cys Gly Arg Tyr Val Ile His His Asp Arg Gly Ala
                370                 375                 380

Ile Val Tyr Tyr Asp Pro Leu Lys Leu Ile Ser Lys Leu Gly Cys Lys
385                 390                 395                 400

His Ile Arg Asp Val Val His Leu Glu Glu Leu Arg Glu Ser Leu Cys
                405                 410                 415

Asp Val Ala Ser Asn Leu Asn Asn Cys Ala Tyr Phe Ser Gln Leu Asp
                420                 425                 430

Glu Ala Val Ala Glu Val His Lys Thr Ala Val Gly Gly Ser Phe Ala
                435                 440                 445

Phe Cys Ser Ile Ile Lys Tyr Leu Ser Asp Lys Arg Leu Phe Arg Asp
450                 455                 460
```

Leu Phe
465

<210> SEQ ID NO 42
<211> LENGTH: 466
<212> TYPE: PRT
<213> ORGANISM: Tobamovirus/TVCV

<400> SEQUENCE: 42

```
Met Gln Phe Tyr Asn Asp Thr Leu Leu Pro Gly Asn Ser Thr Ile Leu
1               5

-continued

```
                355                 360                 365
Tyr Gly Tyr Phe Cys Gly Arg Tyr Val Ile His His Asp Arg Gly Ala
            370                 375                 380
Ile Val Tyr Tyr Asp Pro Leu Lys Leu Ile Ser Lys Leu Gly Cys Lys
385                 390                 395                 400

His Ile Arg Asp Val Val His Leu Glu Glu Leu Arg Glu Ser Leu Cys
                405                 410                 415

Asp Val Ala Ser Asn Leu Asn Asn Cys Ala Tyr Phe Ser Gln Leu Asp
                420                 425                 430

Glu Ala Val Ala Glu Val His Lys Thr Ala Val Gly Gly Ser Phe Ala
            435                 440                 445

Phe Cys Ser Ile Ile Lys Tyr Leu Ser Asp Lys Arg Leu Phe Arg Asp
        450                 455                 460

Leu Phe
465

<210> SEQ ID NO 43
<211> LENGTH: 466
<212> TYPE: PRT
<213> ORGANISM: Tobamovirus/CR-TMV

<400> SEQUENCE: 43

Met Gln Phe Tyr Asn Asp Thr Leu Leu Pro Gly Asn Ser Thr Ile Leu
1

```
Val Glu Tyr Lys Ile Trp Glu Lys Leu Gly Ile Asp Glu Trp Leu Ala
                260                 265                 270

Glu Val Trp Lys Gln Gly His Arg Lys Thr Thr Leu Lys Asp Tyr Thr
            275                 280                 285

Ala Gly Ile Lys Thr Cys Leu Trp Tyr Gln Arg Lys Ser Gly Asp Val
        290                 295                 300

Thr Thr Phe Ile Gly Asn Thr Ile Ile Ala Ala Cys Leu Ser Ser
305                 310                 315                 320

Met Ile Pro Met Asp Lys Val Ile Lys Ala Ala Phe Cys Gly Asp Asp
                325                 330                 335

Ser Leu Ile Tyr Ile Pro Lys Gly Leu Asp Leu Pro Asp Ile Gln Ala
            340                 345                 350

Gly Ala Asn Leu Met Trp Asn Phe Glu Ala Lys Leu Phe Arg Lys Lys
        355                 360                 365

Tyr Gly Tyr Phe Cys Gly Arg Tyr Val Ile His His Asp Arg Gly Ala
    370                 375                 380

Ile Val Tyr Tyr Asp Pro Leu Lys Leu Ile Ser Lys Leu Gly Cys Lys
385                 390                 395                 400

His Ile Arg Asp Val Val His Leu Glu Glu Leu Arg Glu Ser Leu Cys
                405                 410                 415

Asp Val Ala Ser Asn Leu Asn Asn Cys Ala Tyr Phe Ser Gln Leu Asp
            420                 425                 430

Glu Ala Val Ala Glu Val His Lys Thr Ala Val Gly Gly Ser Phe Ala
        435                 440                 445

Phe Cys Ser Ile Ile Lys Tyr Leu Ser Asp Lys Arg Leu Phe Arg Asp
    450                 455                 460

Leu Phe
465

<210> SEQ ID NO 44
<211> LENGTH: 466
<212> TYPE: PRT
<213> ORGANISM: Tobamovirus/RMV-SH

<400> SEQUENCE: 44

Met Gln Phe Tyr Tyr Asp Thr Leu Leu Pro Gly Asn Ser Thr Ile Leu
1               5                   10                  15

Asn Gl

```
Ser Gln Pro Lys Gln Lys Leu Asp Leu Ser Ile Gln Asp Glu Tyr Pro
                165                 170                 175

Ala Leu Gln Thr Ile Val Tyr His Ser Lys Lys Ile Asn Ala Ile Phe
            180                 185                 190

Gly Pro Met Phe Ser Glu Leu Thr Arg Met Leu Leu Glu Arg Ile Asp
        195                 200                 205

Thr Ser Lys Phe Leu Phe Tyr Thr Arg Lys Thr Pro Thr Gln Ile Glu
    210                 215                 220

Glu Phe Phe Ser Asp Leu Asp Ser Ser Gln Ala Met Glu Ile Leu Glu
225                 230                 235                 240

Leu Asp Ile Ser Lys Tyr Asp Lys Ser Gln Asn Glu Phe His Cys Ala
                245                 250                 255

Val Glu Tyr Lys Ile Trp Glu Lys Leu Gly Ile Asp Glu Trp Leu Ala
            260                 265                 270

Glu Val Trp Arg Gln Gly His Arg Lys Thr Thr Leu Lys Asp Tyr Thr
        275                 280                 285

Ala Gly Ile Lys Thr Cys Leu Trp Tyr Gln Arg Lys Ser Gly Asp Val
    290                 295                 300

Thr Thr Phe Ile Gly Asn Thr Ile Ile Ala Ala Cys Leu Ser Ser
305                 310                 315                 320

Met Ile Pro Met Asp Lys Val Ile Lys Ala Ala Phe Cys Gly Asp Asp
                325                 330                 335

Ser Leu Ile Tyr Ile Pro Lys Gly Leu Asp Leu Pro Asp Ile Gln Ala
            340                 345                 350

Gly Ala Asn Leu Thr Trp Asn Phe Glu Ala Lys Leu Phe Arg Lys Lys
        355                 360                 365

Tyr Gly Tyr Phe Cys Gly Arg Tyr Val Ile His His Asp Arg Gly Ala
    370                 375                 380

Ile Val Tyr Tyr Asp Pro Leu Lys Leu Ile Ser Lys Leu Gly Cys Lys
385                 390                 395                 400

His Ile Arg Asp Glu Val His Leu Glu Glu Leu Arg Arg Ser Leu Cys
                405                 410                 415

Asp Val Thr Ser Asn Leu Asn Asn Cys Ala Tyr Phe Ser Gln Leu Asp
            420                 425                 430

Glu Ala Val Ala Glu Val His Lys Thr Ala Val Gly Gly Ala Phe Val
        435                 440                 445

Tyr Cys Ser Ile Ile Lys Tyr Leu Ser Asp Lys Arg Leu Phe Lys Asp
    450                 455                 460

Leu Phe
465

<210> SEQ ID NO 45
<211> LENGTH: 466
<212> TYPE: PRT
<213> ORGANISM: Tobamovirus/CRMV

<400> SEQUENCE: 45

Met Gln Phe Tyr Tyr Asp Thr Leu Leu Pro Gly Asn Ser Thr Ile Leu
1               5                   10                  15

Asn Glu Phe Asp Ala Val Thr Met Asn Leu Arg Asp Ile Ser Leu Asn
            20                  25                  30

Val Lys Asp Cys Arg Ile Asp Phe Ser Lys Ser Val Gln Val Pro Lys
        35                  40                  45

Glu Arg Pro Val Phe Met Lys Pro Lys Leu Arg Thr Ala Ala Glu Met
```

-continued

```
            50                  55                  60
Pro Arg Thr Ala Gly Leu Leu Glu Asn Leu Val Ala Met Ile Lys Arg
 65                  70                  75                  80

Asn Met Asn Ala Pro Asp Leu Thr Gly Thr Ile Asp Ile Glu Asp Thr
                 85                  90                  95

Ala Ser Leu Val Val Glu Lys Phe Trp Asp Ala Tyr Val Val Lys Glu
            100                 105                 110

Phe Ser Gly Thr Asp Gly Met Ala Met Thr Arg Glu Ser Phe Ser Arg
        115                 120                 125

Trp Leu Ser Lys Gln Glu Ser Ser Thr Val Gly Gln Leu Ala Asp Phe
    130                 135                 140

Asn Phe Val Asp Leu Pro Ala Val Asp Glu Tyr Lys His Met Ile Lys
145                 150                 155                 160

Ser Gln Pro Lys Gln Lys Leu Asp Leu Ser Ile Gln Asp Glu Tyr Pro
                165                 170                 175

Ala Leu Gln Thr Ile Val Tyr His Ser Lys Lys Ile Asn Ala Ile Phe
            180                 185                 190

Gly Pro Met Phe Ser Glu Leu Thr Arg Met Leu Leu Glu Thr Ile Asp
        195                 200                 205

Thr Ser Lys Phe Leu Phe Tyr Thr Arg Lys Thr Pro Thr Gln Ile Glu
    210                 215                 220

Glu Phe Phe Ser Asp Leu Asp Ser Ser Gln Ala Met Glu Ile Leu Glu
225                 230                 235                 240

Leu Asp Ile Ser Lys Tyr Asp Lys Ser Gln Asn Glu Phe His Cys Ala
                245                 250                 255

Val Glu Tyr Lys Ile Trp Glu Lys Leu Gly Ile Asp Asp Trp Leu Ala
            260                 265                 270

Glu Val Trp Arg Gln Gly His Arg Lys Thr Thr Leu Lys Asp Tyr Thr
        275                 280                 285

Ala Gly Ile Lys Thr Cys Leu Trp Tyr Gln Arg Lys Ser Gly Asp Val
    290                 295                 300

Thr Thr Phe Ile Gly Asn Thr Ile Ile Ala Ala Cys Leu Ser Ser
305                 310                 315                 320

Met Ile Pro Met Asp Lys Val Ile Lys Ala Ala Phe Cys Gly Asp Asp
                325                 330                 335

Ser Leu Ile Tyr Ile Pro Lys Gly Leu Asp Leu Pro Asp Ile Gln Ala
            340                 345                 350

Gly Ala Asn Leu Thr Trp Asn Phe Glu Ala Lys Leu Phe Arg Lys Lys
        355                 360                 365

Tyr Gly Tyr Phe Cys Gly Arg Tyr Val Ile His His Asp Arg Gly Ala
    370                 375                 380

Ile Val Tyr Tyr Asp Pro Leu Lys Leu Ile Ser Lys Leu Gly Cys Lys
385                 390                 395                 400

His Ile Arg Asp Glu Val His Leu Glu Glu Leu Arg Arg Ser Leu Cys
                405                 410                 415

Asp Val Thr Ser Asn Leu Asn Asn Cys Ala Tyr Phe Ser Gln Leu Asp
            420                 425                 430

Glu Ala Val Ala Glu Val His Lys Thr Ala Val Gly Gly Ala Phe Val
        435                 440                 445

Tyr Cys Ser Ile Ile Lys Tyr Leu Ser Asp Lys Arg Leu Phe Lys Asp
    450                 455                 460

Leu Phe
465
```

<210> SEQ ID NO 46
<211> LENGTH: 417
<212> TYPE: PRT
<213> ORGANISM: Tobamovirus/TMV-CG

<400> SEQUENCE: 46

```
Met Gln Phe Tyr Tyr Asp Thr Leu Leu Pro Gly Asn Ser Thr Ile Leu
1               5                   10                  15

Asn Glu Phe Asp Ala Val Thr Met Asn Leu Arg Asp Ile Ser Leu Asn
            20                  25                  30

Val Lys Asp Cys Arg Ile Asp Phe Ser Lys Ser Val Gln Leu Pro Arg
        35                  40                  45

Glu Arg Pro Ile Phe Met Lys Pro Lys Leu Arg Thr Ala Ala Glu Met
    50                  55                  60

Pro Arg Thr Ala Gly Leu Leu Glu Asn Leu Val Ala Met Ile Lys Arg
65                  70                  75                  80

Asn Met Asn Ala Pro Asp Leu Thr Gly Thr Ile Asp Ile Glu Asp Thr
                85                  90                  95

Ala Ser Leu Val Val Glu Lys Phe Trp Asp Ala Tyr Val Val Lys Glu
            100                 105                 110

Phe Ser Gly Thr Asp Gly Met Ala Met Thr Arg Glu Ser Phe Ser Arg
        115                 120                 125

Trp Leu Ser Lys Gln Glu Ser Ser Thr Val Gly Gln Leu Ala Asp Phe
    130                 135                 140

Asn Phe Val Asp Leu Pro Ala Val Asp Glu Tyr Lys His Met Ile Lys
145                 150                 155                 160

Ser Gln Pro Lys Gln Lys Leu Asp Leu Ser Ile Gln Asp Glu Tyr Pro
                165                 170                 175

Ala Leu Gln Thr Ile Val Tyr His Ser Lys Lys Ile Asn Ala Ile Phe
            180                 185                 190

Gly Pro Met Phe Ser Glu Leu Thr Arg Met Leu Leu Glu Arg Ile Asp
        195                 200                 205

Thr Ser Lys Phe Leu Phe Tyr Thr Arg Lys Thr Pro Thr Gln Ile Glu
    210                 215                 220

Glu Phe Phe Ser Asp Leu Asp Ser Ser Gln Ala Met Glu Ile Leu Glu
225                 230                 235                 240

Leu Asp Ile Ser Lys Tyr Asp Lys Ser Gln Asn Glu Phe His Cys Ala
                245                 250                 255

Val Glu Tyr Lys Ile Trp Glu Lys Leu Gly Ile Asp Asp Trp Leu Ala
            260                 265                 270

Glu Val Trp Arg Gln Gly His Arg Lys Thr Thr Leu Lys Asp Tyr Thr
        275                 280                 285

Ala Gly Ile Lys Thr Cys Leu Trp Tyr Gln Arg Lys Ser Gly Asp Val
    290                 295                 300

Thr Thr Phe Ile Gly Asn Thr Ile Ile Ile Ala Ala Cys Leu Ser Ser
305                 310                 315                 320

Met Ile Pro Met Asp Lys Val Ile Lys Ala Ala Phe Cys Gly Asp Asp
                325                 330                 335

Ser Leu Ile Tyr Ile Pro Lys Gly Leu Asp Leu Pro Asp Ile Gln Ala
            340                 345                 350

Gly Ala Asn Leu Thr Trp Asn Phe Glu Ala Lys Leu Phe Arg Lys Lys
        355                 360                 365

Tyr Gly Tyr Phe Cys Gly Arg Tyr Val Ile His His Asp Arg Gly Ala
```

```
                    370                 375                 380
Ile Val Tyr Tyr Asp Pro Leu Lys Leu Ile Ser Lys Leu Gly Cys Lys
385                 390                 395                 400

His Ile Arg Asp Glu Val His Leu Glu Glu Leu Arg Arg Ser Leu Cys
                405                 410                 415

Asp

<210> SEQ ID NO 47
<211> LENGTH: 426
<212> TYPE: PRT
<213> ORGANISM: Tobamovirus/TMV-OB

<400> SEQUENCE: 47

Gln Asp Leu Gln Phe Tyr Tyr Asp Lys Cys Leu Pro Gly Asn Ser Thr
1               5                   10                  15

Val Leu Asn Glu Phe Asp Ala Val Thr Met Asn Cys Ser Asp Ile Ser
                20                  25                  30

Leu Asn Val Lys Asp Cys Val Leu Asp Phe Ser Lys Ser Val Pro Leu
            35                  40                  45

Pro Arg Asp Asn Thr Lys Val Pro Met Thr Pro Val Ile Arg Thr Ala
50                  55                  60

Ala Glu Arg Pro Arg Ser Gln Gly Leu Leu Glu Asn Leu Val Ala Met
65                  70                  75                  80

Ile Lys Arg Asn Phe Asn Ser Pro Glu Leu Ser Gly Thr Val Asp Met
                85                  90                  95

Glu Asn Thr Ala Ser Val Val Ala Asp Arg Phe Phe Asp Ser Tyr Phe
                100                 105                 110

Leu Lys Asp Lys Leu Ser Gly Cys Ser Leu Gly Asp Ser Gly Gly Lys
            115                 120                 125

Asn Ile Ile Asp Arg Gln Ala Leu Ile Arg Trp Met Glu Lys Gln Glu
130                 135                 140

Lys Ser Thr Ile Gly Gln Leu Ala Asp Tyr Asp Phe Val Asp Leu Pro
145                 150                 155                 160

Ala Ile Asp Gln Tyr Arg His Ile Ile Lys Ser Gln Pro Lys Gln Lys
                165                 170                 175

Leu Asp Leu Ser Ile Gln Ser Glu Tyr Pro Ser Leu Gln Thr Ile Val
            180                 185                 190

Tyr His Ser Lys Lys Ile Asn Ala Leu Phe Gly Pro Ile Phe Ser Glu
                195                 200                 205

Leu Thr Arg Gln Met Leu Ser Ala Ile Asp Thr Ser Arg Tyr Leu Phe
        210                 215                 220

Phe Thr Arg Lys Thr Pro Glu Gln Ile Glu Glu Phe Phe Ser Asp Leu
225                 230                 235                 240

Asp Ala Thr Leu Lys Asp Tyr Thr Ala Gly Ile Lys Thr Cys Leu Trp
                245                 250                 255

Tyr Gln Arg Lys Ser Gly Asp Val Thr Thr Phe Ile Gly Asn Thr Val
                260                 265                 270

Ile Ile Ala Ala Cys Met Ala Ser Met Leu Pro Met Glu Lys Val Ile
            275                 280                 285

Lys Ala Ala Phe Cys Gly Asp Asp Ser Leu Val Tyr Leu Pro Lys Gly
        290                 295                 300

Cys Glu Leu Pro Asn Ile Gln Ser Cys Ala Asn Leu Met Trp Asn Phe
305                 310                 315                 320

Glu Ala Lys Leu Phe Lys Lys Thr Tyr Gly Tyr Phe Cys Gly Arg Tyr
```

```
                   325                 330                 335
Val Ile His His Asp Arg Gly Ala Ile Val Tyr Val Asp Pro Leu Lys
            340                 345                 350

Ile Ile Ser Lys Leu Gly Ala Lys His Ile Thr Asp Lys Glu His Leu
            355                 360                 365

Glu Glu Phe Arg Ile Ser Leu Ala Asp Val Ser Lys Ser Leu Asn Asn
            370                 375                 380

Cys Ala Tyr Tyr Ala Gln Leu Asp Glu Ala Val Arg Glu Val His Lys
385                 390                 395                 400

Thr Ala Pro Pro Gly Ser Phe Val Tyr Lys Cys Ile Val Lys Phe Leu
            405                 410                 415

Ser Asn Arg Val Leu Phe Glu Ser Leu Phe
            420                 425

<210> SEQ ID NO 48
<211> LENGTH: 473
<212> TYPE: PRT
<213> ORGANISM: Tobamovirus/CGMMV

<400> SEQUENCE: 48

Met Gln Glu Phe Tyr Asp Arg Cys Leu Pro Gly Asn Ser Phe Val Leu
1               5                   10                  15

Asn Asp Phe Asp Ala Val Thr Met Arg Leu Arg Asp Asn Glu Phe Asn
            20                  25                  30

Leu Gln Pro Cys Arg Leu Thr Leu Ser Asn Leu Asp Pro Val Pro Ala
            35                  40                  45

Leu Ile Lys Asn Glu Ala Gln Asn Phe Leu Ile Pro Val Leu Arg Thr
50                  55                  60

Ala Cys Glu Arg Pro Arg Ile Pro Gly Leu Leu Glu Asn Leu Val Ala
65                  70                  75                  80

Met Ile Lys Arg Asn Met Asn Thr Pro Asp Leu Ala Gly Thr Val Asp
            85                  90                  95

Ile Thr Asn Met Ser Ile Ser Ile Val Asp Asn Phe Phe Ser Ser Phe
            100                 105                 110

Val Arg Asp Glu Val Leu Leu Asp His Leu Asp Cys Val Arg Ala Ser
            115                 120                 125

Ser Ile Gln Ser Phe Ser Asp Trp Phe Ser Cys Gln Pro Thr Ser Ala
            130                 135                 140

Val Gly Gln Leu Ala Asn Phe Asn Phe Ile Asp Leu Pro Ala Phe Asp
145                 150                 155                 160

Thr Tyr Met His Met Ile Lys Arg Gln Pro Lys Ser Arg Leu Asp Thr
            165                 170                 175

Ser Ile Gln Ser Glu Tyr Pro Ala Leu Gln Thr Ile Val Tyr His Pro
            180                 185                 190

Lys Val Val Asn Ala Val Phe Gly Pro Val Phe Lys Tyr Leu Thr Thr
            195                 200                 205

Lys Phe Leu Ser Met Val Asp Ser Ser Lys Phe Phe Phe Tyr Thr Arg
            210                 215                 220

Lys Lys Pro Glu Asp Leu Gln Glu Phe Phe Ser Asp Leu Ser Ser His
225                 230                 235                 240

Ser Asp Tyr Glu Ile Leu Glu Leu Asp Val Ser Lys Tyr Asp Lys Ser
            245                 250                 255

Gln Ser Asp Phe His Phe Ser Ile Glu Met Ala Ile Trp Glu Lys Leu
            260                 265                 270
```

-continued

Gly Leu Asp Asp Ile Leu Ala Trp Met Trp Ser Met Gly His Lys Arg
            275                 280                 285

Thr Ile Leu Gln Asp Phe Gln Ala Gly Ile Lys Thr Leu Ile Tyr Tyr
        290                 295                 300

Gln Arg Lys Ser Gly Asp Val Thr Thr Phe Ile Gly Asn Thr Phe Ile
305                 310                 315                 320

Ile Ala Ala Cys Val Ala Ser Met Leu Pro Leu Asp Lys Cys Phe Lys
                325                 330                 335

Ala Ser Phe Cys Gly Asp Asp Ser Leu Ile Tyr Leu Pro Lys Gly Leu
            340                 345                 350

Glu Tyr Pro Asp Ile Gln Ala Thr Ala Asn Leu Val Trp Asn Phe Glu
        355                 360                 365

Ala Lys Leu Phe Arg Lys Lys Tyr Gly Tyr Phe Cys Gly Lys Tyr Ile
    370                 375                 380

Ile His His Ala Asn Gly Cys Ile Val Tyr Pro Asp Pro Leu Lys Leu
385                 390                 395                 400

Ile Ser Lys Leu Gly Asn Lys Ser Leu Val Gly Tyr Glu His Val Glu
                405                 410                 415

Glu Phe Arg Ile Ser Leu Leu Asp Val Ala His Ser Leu Phe Asn Gly
            420                 425                 430

Ala Tyr Phe His Leu Leu Asp Asp Ala Ile His Glu Leu Phe Pro Asn
        435                 440                 445

Ala Gly Gly Cys Ser Phe Val Ile Asn Cys Leu Cys Lys Tyr Leu Ser
    450                 455                 460

Asp Lys Arg Leu Phe Arg Ser Leu Tyr
465                 470

<210> SEQ ID NO 49
<211> LENGTH: 475
<212> TYPE: PRT
<213> ORGANISM: Tobamovirus/CGMMV-W

<400> SEQUENCE: 49

Thr Asp Met Gln Glu Phe Tyr Asp Arg Cys Leu Pro Gly Asn Ser Phe
1               5                   10                  15

Val Leu Asn Asp Phe Asp Ala Val Thr Met Arg Leu Arg Asp Asn Glu
            20                  25                  30

Phe Asn Leu Gln Pro Cys Arg Leu Thr Leu Ser Asn Leu Asp Pro Val
        35                  40                  45

Pro Ala Leu Val Lys Ser Glu Ala Gln Asn Phe Leu Ile Pro Val Leu
    50                  55                  60

Arg Thr Ala Cys Glu Arg Pro Arg Ile Pro Gly Leu Leu Glu Asn Leu
65                  70                  75                  80

Val Ala Met Ile Lys Arg Asn Met Asn Thr Pro Asp Leu Ala Gly Thr
                85                  90                  95

Val Asp Ile Thr Asn Met Ser Ile Ser Ile Val Asp Asn Phe Phe Ser
            100                 105                 110

Ser Phe Val Arg Asp Glu Val Leu Leu Asp His Leu Asp Cys Val Arg
        115                 120                 125

Ala Ser Ser Ile Gln Ser Phe Ser Asp Trp Phe Ser Cys Gln Pro Thr
    130                 135                 140

Ser Ala Val Gly Gln Leu Ala Asn Phe Asn Phe Ile Asp Leu Pro Ala
145                 150                 155                 160

Phe Asp Thr Tyr Met His Met Ile Lys Arg Gln Pro Lys Ser Arg Leu
                165                 170                 175

```
Asp Thr Ser Ile Gln Ser Glu Tyr Pro Ala Leu Gln Thr Ile Val Tyr
            180                 185                 190

His Pro Lys Val Val Asn Ala Val Phe Gly Pro Val Phe Lys Tyr Leu
            195                 200                 205

Thr Thr Lys Phe Leu Ser Met Val Asp Ser Ser Lys Phe Phe Phe Tyr
            210                 215                 220

Thr Arg Lys Lys Pro Glu Asp Leu Gln Glu Phe Phe Ser Asp Leu Ser
225                 230                 235                 240

Ser His Ser Asp Tyr Glu Ile Leu Glu Leu Asp Val Ser Lys Tyr Asp
            245                 250                 255

Lys Ser Gln Ser Asp Phe His Phe Ser Ile Glu Met Ala Ile Trp Glu
            260                 265                 270

Lys Leu Gly Leu Asp Asp Ile Leu Ala Trp Met Trp Ser Met Gly His
            275                 280                 285

Lys Arg Thr Ile Leu Gln Asp Phe Gln Ala Gly Ile Lys Thr Leu Ile
            290                 295                 300

Tyr Tyr Gln Arg Lys Ser Gly Asp Val Thr Thr Phe Ile Gly Asn Thr
305                 310                 315                 320

Phe Ile Ile Ala Ala Cys Val Ala Ser Met Leu Pro Leu Asp Lys Cys
                325                 330                 335

Phe Lys Ala Ser Phe Cys Gly Asp Asp Ser Leu Ile Tyr Leu Pro Lys
            340                 345                 350

Gly Leu Glu Tyr Pro Asp Ile Gln Ala Thr Ala Asn Leu Val Trp Asn
            355                 360                 365

Phe Glu Ala Lys Leu Phe Arg Lys Lys Tyr Gly Tyr Phe Cys Gly Lys
370                 375                 380

Tyr Ile Ile His His Ala Asn Gly Cys Ile Val Tyr Pro Asp Pro Leu
385                 390                 395                 400

Lys Leu Ile Ser Lys Leu Gly Asn Lys Ser Leu Val Gly Tyr Glu His
                405                 410                 415

Val Glu Glu Phe Arg Ile Ser Leu Leu Asp Val Ala His Ser Leu Phe
            420                 425                 430

Asn Gly Ala Tyr Phe His Leu Leu Asp Asp Ala Ile His Glu Leu Phe
            435                 440                 445

Pro Asn Ala Gly Gly Cys Ser Phe Val Ile Asn Cys Leu Cys Lys Tyr
            450                 455                 460

Leu Ser Asp Lys Arg Leu Phe Arg Ser Leu Tyr
465                 470                 475

<210> SEQ ID NO 50
<211> LENGTH: 473
<212> TYPE: PRT
<213> ORGANISM: Tobamovirus/CFMMV

<400> SEQUENCE: 50

Met Gln Asn Phe Tyr Asp Ala Cys Leu Pro Gly Asn Ser Phe Val Leu
1               5                   10                  15

Asn Asp Tyr Asp Ser Val Thr Met Arg Leu Val Asp Asn Glu Ile Asn
            20                  25                  30

Leu Gln Pro Cys Arg Leu Thr Leu Ser Lys Ala Asp Pro Val Thr Glu
            35                  40                  45

Ser Leu Lys Met Glu Lys Lys Glu Phe Leu Ile Pro Leu Gly Lys Thr
        50                  55                  60

Ala Thr Glu Arg Pro Arg Ile Pro Gly Leu Leu Glu Asn Leu Ile Ala
```

```
                65                  70                  75                  80
Ile Val Lys Arg Asn Phe Asn Thr Pro Asp Leu Ala Gly Ser Leu Asp
                    85                  90                  95

Ile Ser Ser Ile Ser Lys Gly Val Val Asp Asn Phe Phe Ser Thr Phe
                    100                 105                 110

Leu Arg Asp Glu Gln Leu Ala Asp His Leu Cys Lys Val Arg Ser Leu
                    115                 120                 125

Ser Leu Glu Ser Phe Ser Ala Trp Phe Asp Asn Gln Ser Thr Cys Ala
                    130                 135                 140

Leu Gly Gln Leu Ser Asn Phe Asp Phe Val Asp Leu Pro Pro Val Asp
145                 150                 155                 160

Val Tyr Asn His Met Ile Lys Arg Gln Pro Lys Ser Lys Leu Asp Thr
                    165                 170                 175

Ser Ile Gln Ser Glu Tyr Pro Ala Leu Gln Thr Ile Val Tyr His Ser
                    180                 185                 190

Lys Leu Val Asn Ala Val Phe Gly Pro Val Phe Arg Tyr Leu Thr Ser
                    195                 200                 205

Glu Phe Leu Ser Met Val Asp Asn Ser Lys Phe Phe Phe Tyr Thr Arg
                    210                 215                 220

Lys Leu Arg Met Ile Cys Lys Phe Leu Phe Pro His Phe Pro Asn Lys
225                 230                 235                 240

Gln Glu Tyr Glu Ile Leu Glu Leu Asp Val Ser Lys Tyr Asp Lys Ser
                    245                 250                 255

Gln Asn Asp Phe His Gln Ala Val Glu Met Leu Ile Trp Glu Arg Leu
                    260                 265                 270

Gly Leu Asp Asp Ile Leu Ala Arg Ile Trp Glu Met Gly His Lys Lys
                    275                 280                 285

Thr His Ile Ser Asp Phe Gln Ala Gly Ile Lys Thr Leu Ile Tyr Tyr
                    290                 295                 300

Gln Arg Lys Ser Gly Asp Val Thr Thr Phe Ile Gly Asn Thr Phe Ile
305                 310                 315                 320

Ile Ala Ala Cys Val Ala Ser Met Val Pro Leu Ser Arg Ser Phe Lys
                    325                 330                 335

Ala Ala Phe Cys Gly Asp Asp Ser Leu Ile Tyr Met Pro Pro Asn Leu
                    340                 345                 350

Glu Tyr Asn Asp Ile Gln Ser Thr Ala Asn Leu Val Trp Asn Phe Glu
                    355                 360                 365

Ala Lys Leu Tyr Lys Lys Tyr Gly Tyr Phe Cys Gly Lys Tyr Val
                    370                 375                 380

Ile His His Ala Asn Gly Cys Ile Val Tyr Pro Asp Pro Leu Lys Leu
385                 390                 395                 400

Ile Ser Lys Leu Gly Asn Lys Ser Leu Glu Ser Tyr Asp His Leu Glu
                    405                 410                 415

Glu Phe Arg Ile Ser Leu Met Asp Val Ala Lys Pro Leu Phe Asn Ala
                    420                 425                 430

Ala Tyr Phe His Leu Leu Asp Asp Ala Ile His Glu Tyr Phe Pro Ser
                    435                 440                 445

Val Gly Gly Ser Thr Phe Ala Ile Ser Ser Leu Cys Lys Tyr Leu Ser
                    450                 455                 460

Asn Lys Gln Leu Phe Gly Ser Leu Phe
465                 470
```

<210> SEQ ID NO 51

<211> LENGTH: 475
<212> TYPE: PRT
<213> ORGANISM: Tobamovirus/YCGMMV

<400> SEQUENCE: 51

```
Thr Asp Met Gln Ser Phe Tyr Asp Ala Cys Leu Pro Gly Asn Ser Phe
1               5                   10                  15

Val Leu Asn Asp Tyr Asp Ser Val Thr Met Arg Leu Ala Asp Asn Glu
            20                  25                  30

Phe Asn Leu Gln Pro Cys Arg Leu Thr Leu Ser Lys Ala Asp Pro Val
        35                  40                  45

Ala Glu Ser Ile Lys Leu Glu Arg Lys Asn Ile Asp Lys Leu Asp Leu
    50                  55                  60

Lys Thr Ala Thr Glu Arg Pro Arg Ile Pro Gly Phe Leu Glu Asn Leu
65                  70                  75                  80

Val Ala Ile Val Lys Arg Asn Phe Asn Thr Pro Asp Leu Ala Gly Val
                85                  90                  95

Leu Asp Ile Asp Thr Ile Ser Lys Ser Val Val Asp Asn Phe Phe Thr
            100                 105                 110

Thr Phe Leu Arg Asp Glu Gln Leu Ser Asp His Leu Val Arg Val Arg
        115                 120                 125

Ser Cys Ser Leu Glu Ser Phe Ser Ala Trp Phe His Asn Gln Ala Thr
    130                 135                 140

Ala Ala Met Gly Gln Leu Ala Asn Phe Asp Phe Ser Asp Leu Pro Pro
145                 150                 155                 160

Val Asp Met Tyr Thr His Met Ile Lys Arg Gln Pro Lys Ser Lys Leu
                165                 170                 175

Asp Thr Ser Ile Gln Ser Glu Tyr Pro Ala Leu Gln Thr Ile Val Tyr
            180                 185                 190

His Ser Lys Leu Val Asn Ala Val Phe Gly Pro Val Phe Arg Tyr Leu
        195                 200                 205

Thr Ser Glu Phe Leu Ser Met Val Asp Asn Ser Lys Phe Phe Phe Tyr
    210                 215                 220

Thr Arg Lys Thr Pro Glu Asp Leu Gln Ser Phe Phe Ser Thr Leu Ser
225                 230                 235                 240

Ala Lys Glu Ser Tyr Glu Ile Leu Glu Leu Asp Val Ser Lys Tyr Asp
                245                 250                 255

Lys Ser Gln Thr Asp Phe His Gln Ala Val Glu Met Leu Ile Trp Glu
            260                 265                 270

Arg Leu Gly Leu Asp Asp Val Leu Ala Arg Ile Trp Glu Met Gly His
        275                 280                 285

Lys Lys Thr Ser Ile Ser Asp Phe Gln Ala Gly Ile Lys Thr Val Ile
    290                 295                 300

Tyr Tyr Gln Arg Lys Ser Gly Asp Val Thr Thr Phe Ile Gly Asn Thr
305                 310                 315                 320

Phe Ile Ile Ala Ala Cys Val Ala Ser Met Ile Pro Leu Ser Arg Ser
                325                 330                 335

Phe Lys Ala Ser Phe Cys Gly Asp Asp Ser Leu Ile Tyr Met Pro Pro
            340                 345                 350

Gly Leu Glu Tyr Pro Asp Ile Gln Ala Thr Ala Asn Leu Val Trp Asn
        355                 360                 365

Phe Glu Ala Lys Leu Phe Lys Lys Arg Tyr Gly Tyr Phe Cys Gly Lys
    370                 375                 380

Tyr Val Ile His His Ser Asn Gly Cys Ile Val Tyr Pro Asp Pro Leu
```

-continued 385 390 395 400

Lys Leu Ile Ser Lys Leu Gly Asn Lys Ser Leu Glu Ser Tyr Asp His
405 410 415

Leu Glu Glu Phe Arg Ile Ser Leu Met Asp Val Ala Lys Pro Leu Phe
420 425 430

Asn Ala Ala Tyr Phe His Leu Leu Asp Asp Ala Ile His Glu Tyr Phe
435 440 445

Pro Ser Val Gly Gly Ser Ser Phe Ala Ile Asn Ser Leu Cys Lys Tyr
450 455 460

Leu Ser Asp Lys Trp Leu Phe Arg Ser Leu Phe
465 470 475

<210> SEQ ID NO 52
<211> LENGTH: 470
<212> TYPE: PRT
<213> ORGANISM: Tobamovirus/SHMV

<400> SEQUENCE: 52

Leu Gln Tyr Phe Tyr Asp Ser Trp Leu Pro Gly Asn Ser Phe Val Gln
1 5 10 15

Asn Asn His Asp Gln Trp Ser Ile Ile Ser Ser Asp Ile Asn Leu His
20 25 30

Ser Glu Ala Val Arg Leu Asp Met Asn Lys Arg His Ile Pro Arg Thr
35 40 45

Lys Gly Glu Phe Leu Arg Pro Leu Leu Asn Thr Ala Val Glu Pro Pro
50 55 60

Arg Ile Pro Gly Leu Leu Glu Asn Leu Leu Ala Leu Ile Lys Arg Asn
65 70 75 80

Phe Asn Ala Pro Asp Leu Ala Gly Gln Leu Asp Tyr Asp Phe Leu Ser
85 90 95

Arg Lys Val Cys Asp Gly Phe Phe Gly Lys Leu Leu Pro Pro Asp Val
100 105 110

Glu Ala Ser Glu Leu Leu Arg Leu Pro Val Asp His Met Tyr Ser Val
115 120 125

Gln Asn Phe Asp Asp Trp Leu Asn Lys Gln Glu Pro Gly Val Val Gly
130 135 140

Gln Leu Ala Asn Trp Asp His Ile Gly Met Pro Ala Ala Asp Gln Tyr
145 150 155 160

Arg His Met Ile Lys Arg Thr Pro Lys Ala Lys Leu Asp Leu Ser Ile
165 170 175

Gln Ser Glu Tyr Pro Ala Leu Gln Thr Ile Val Tyr His Ser Lys His
180 185 190

Val Asn Ala Val Phe Gly Pro Ile Phe Ser Cys Leu Thr Glu Arg Leu
195 200 205

Leu Ser Val Val Asp Pro Leu Arg Phe Lys Phe Phe Thr Arg Thr Thr
210 215 220

Pro Ala Asp Leu Glu Phe Phe Phe Arg Asp Met Val Val Gly Asp Met
225 230 235 240

Glu Ile Leu Glu Leu Asp Ile Ser Lys Tyr Asp Lys Ser Gln Asn Lys
245 250 255

Phe His Phe Glu Val Glu Met Arg Ile Trp Glu Met Leu Gly Ile Asp
260 265 270

Lys Tyr Ile Glu Lys Val Trp Glu Asn Gly His Arg Lys Thr His Leu
275 280 285

-continued

```
Arg Asp Tyr Thr Ala Gly Ile Lys Thr Val Ile Glu Tyr Gln Arg Lys
    290                 295                 300

Ser Gly Asp Val Thr Thr Phe Ile Gly Asn Thr Ile Ile Ile Ala Ala
305                 310                 315                 320

Cys Leu Cys Ser Ile Leu Pro Met Glu Lys Val Phe Lys Ala Gly Phe
                325                 330                 335

Cys Gly Asp Asp Ser Ile Ile Tyr Leu Pro Arg Asn Leu Leu Tyr Pro
            340                 345                 350

Asp Ile Gln Ser Val Ser Asn Asn Met Trp Asn Phe Glu Ala Lys Leu
        355                 360                 365

Phe Lys Lys Leu His Gly Tyr Phe Cys Gly Arg Tyr Ile Leu Arg Asn
    370                 375                 380

Gly Arg Tyr Leu Arg Leu Leu Pro Asp Pro Leu Lys Ile Ile Thr Lys
385                 390                 395                 400

Leu Gly Cys Lys Ala Ile Lys Asp Trp Asp His Leu Glu Glu Phe Arg
                405                 410                 415

Ile Ser Met Phe Asp Met Ala Cys Glu Tyr Lys Asn Cys Phe Gly Phe
            420                 425                 430

Asp Val Leu Glu Ser Ala Val Lys Glu Ser Phe Pro Lys Ala Glu Gly
        435                 440                 445

Cys Asn Val Ala Phe Cys Ala Ile Tyr Lys Phe Leu Ser Asn Lys Tyr
    450                 455                 460

Leu Phe Arg Thr Leu Phe
465                 470
```

<210> SEQ ID NO 53
<211> LENGTH: 458
<212> TYPE: PRT
<213> ORGANISM: Tobamovirus/POLIORDRP

<400> SEQUENCE: 53

```
Gly Glu Ile Gln Trp Met Arg Pro Ser Lys Glu Val Gly Tyr Pro Ile
1               5                   10                  15

Ile Asn Ala Pro Ser Lys Thr Lys Leu Glu Pro Ser Ala Phe His Tyr
            20                  25                  30

Val Phe Glu Gly Val Lys Glu Pro Ala Val Leu Thr Lys Asn Asp Pro
        35                  40                  45

Arg Leu Lys Thr Asn Phe Glu Glu Ala Ile Phe Ser Lys Tyr Val Gly
    50                  55                  60

Asn Lys Ile Thr Glu Val Asp Glu His Met Lys Glu Ala Val Asp His
65                  70                  75                  80

Tyr Ala Gly Gln Leu Met Ser Leu Asp Ile Asn Thr Glu Gln Met Cys
                85                  90                  95

Leu Glu Asp Ala Met Tyr Gly Thr Asp Gly Leu Glu Ala Leu Asp Leu
            100                 105                 110

Ser Thr Ser Ala Gly Tyr Pro Tyr Val Ala Met Gly Lys Lys Lys Arg
        115                 120                 125

Asp Ile Leu Asn Lys Gln Thr Arg Asp Thr Lys Glu Met Gln Lys Leu
    130                 135                 140

Leu Asp Thr Tyr Gly Ile Asn Leu Pro Leu Val Thr Tyr Val Lys Asp
145                 150                 155                 160

Glu Leu Arg Ser Lys Thr Lys Val Glu Gln Gly Lys Ser Arg Leu Ile
                165                 170                 175

Glu Ala Ser Ser Leu Asn Asp Ser Val Ala Met Arg Met Ala Phe Gly
            180                 185                 190
```

-continued

```
Asn Leu Tyr Ala Ala Phe His Lys Asn Pro Gly Val Ile Thr Gly Ser
        195                 200                 205

Ala Val Gly Cys Asp Pro Asp Leu Phe Trp Ser Lys Ile Pro Val Leu
        210                 215                 220

Met Glu Glu Lys Leu Phe Ala Phe Asp Tyr Thr Gly Tyr Asp Ala Ser
225                 230                 235                 240

Leu Ser Pro Ala Trp Phe Glu Ala Leu Glu Met Val Leu Glu Lys Ile
                245                 250                 255

Gly Phe Gly Asp Arg Val Asp Tyr Ile Asp Tyr Leu Asn His Ser His
                260                 265                 270

His Leu Tyr Lys Asn Lys Thr Tyr Cys Val Lys Gly Gly Met Pro Ser
        275                 280                 285

Gly Cys Ser Gly Thr Ser Ile Phe Asn Ser Met Ile Asn Asn Leu Ile
        290                 295                 300

Ile Arg Thr Leu Leu Leu Lys Thr Tyr Lys Gly Ile Asp Leu Asp His
305                 310                 315                 320

Leu Lys Met Ile Ala Tyr Gly Asp Asp Val Ile Ala Ser Tyr Pro His
                325                 330                 335

Glu Val Asp Ala Ser Leu Leu Ala Gln Ser Gly Lys Asp Tyr Gly Leu
                340                 345                 350

Thr Met Thr Pro Ala Asp Lys Ser Ala Ile Phe Glu Thr Val Thr Trp
                355                 360                 365

Glu Asn Val Thr Phe Leu Lys Arg Phe Phe Arg Ala Asp Glu Lys Tyr
370                 375                 380

Pro Phe Leu Ile His Pro Val Met Pro Met Lys Glu Ile His Glu Ser
385                 390                 395                 400

Ile Arg Trp Thr Lys Asp Pro Arg Asn Thr Gln Asp His Val Arg Ser
                405                 410                 415

Leu Cys Leu Leu Ala Trp His Asn Gly Glu Glu Glu Tyr Asn Lys Phe
                420                 425                 430

Leu Ala Lys Ile Arg Ser Val Pro Ile Gly Arg Ala Leu Leu Leu Pro
                435                 440                 445

Glu Tyr Ser Thr Leu Tyr Arg Arg Trp Leu
450                 455
```

SYSTEM FOR EXPRESSION OF GENES IN PLANTS

CROSS-REFERENCE TO RELATED APPLICATION

This application claims priority to U.S. Provisional Patent Application No. 60/444,615, filed Feb. 3, 2003, which is incorporated herein by reference.

BACKGROUND OF THE INVENTION

In recent years, plants have been increasingly used as a host system for the expression of recombinant proteins. Such expression can be accomplished either by integrating the gene of interest into a plant genome, to create a transgenic plant that stably expresses the desired protein, or by introducing the gene of interest into a plant vector that can be introduced into, and transiently maintained in, plant cells. Viral vector systems have proven to be particularly useful.

However, there remains a need for developing improved systems for expressing transgenes in plants. For example, one disadvantage with existing viral vector systems is that the viruses may infect non-target plants, potentially posing significant environmental risks. Also, many available engineered plant viruses do not express transgenes at desired levels, and/or in desired target plants or tissues. The present invention addresses many of these problems, and others.

SUMMARY OF THE INVENTION

The present invention encompasses the recognition that there is a need to develop expression systems for plants that present only a minimal risk of environmental contamination. The invention provides methods and reagents for expression of polynucleotide and polypeptide products in plants with a reduced risk of widespread contamination.

For example, in one aspect, the invention provides sets of viral expression vectors, each of which is incapable of establishing a systemic infection on its own, but which together allow for systemic infection. Cross-complementation (also referred to as trans-complementation) by the vectors allows an initial local infection (e.g., established by inoculation) to move into uninoculated leaves and establish a systemic infection.

In specific embodiments, the invention provides a system including a producer vector that includes a polynucleotide of interest but lacks functional versions of one or more genes necessary for long-distance movement, together with a carrier vector that provides a functional long distance movement protein coding sequence. For example, the invention provides a system for expressing a polynucleotide of interest in a plant cell or whole plant, comprising: (i) a carrier vector that includes a coat protein encoding component from a first plant virus; and (ii) a producer vector that includes a polynucleotide of interest, and further includes at least one component from a second plant virus, but lacks a functional coat protein gene. The invention further provides a system for expressing a polynucleotide of interest in a plant cell or whole plant, comprising: (i) a carrier vector that includes a movement protein encoding component from a first plant virus; and (ii) a producer vector that includes a polynucleotide of interest, and further includes at least one component from a second plant virus, but lacks a functional movement protein gene.

In certain embodiments of the invention the carrier vector is defective for replication. For instance, the producer vector may include a replicase gene (e.g., an RNA polymerase gene) and a movement protein gene (so that the vector is competent for cell-to-cell movement), but may lack a coat protein gene (so that the vector is not competent for long-distance (systemic) movement). The carrier vector may include a coat protein gene (so that the vector is competent for long-distance movement), but may lack a replicase gene (so that the vector is unable to self-replicate). Alternatively, the carrier vector might include a replicase gene (so that the vector is replication competent), and might be used with a producer vector that lacks both replication and long-distance movement capability. Preferred vectors are viral vectors.

The invention further provides a variety of vectors that can be used as compoments of the inventive system(s) or for other purposes. For example, the invention provides a vector comprising: (a) one or more components from a first plant virus; and (b) a partial or complete 3' untranslated region from an RNA of a second plant virus. In certain embodiments of the invention the 3' untranslated region facilitates systemic spread of the virus. The 3' untranslated region may comprise a recognition site for complex formation with coat protein.

In other aspects, the invention also provides a variety of methods for expressing polynucleotides in plants, e.g., using the inventive vectors and systems described herein.

One advantage of the inventive system for expressing polynucleotides in plants is that it reduces or eliminates the risk that vectors, particularly recombinant vectors comprising the polynucleotide(s) to be expressed, will spread to non-target plants, thereby significantly improving the environmental safety of gene expression in plants and allowing more flexibility in the cultivation of recipient plants.

Another advantage associated with the present invention is that it allows the researcher to design a plant expression system with qualities of more than one plant virus. For instance, in certain embodiments of the invention the producer vector desirably has the polynucleotide of interest positioned such that its expression is controlled by the coat protein ("CP") promoter. In many cases, therefore, it will be desirable to base the producer vector on a viral system with a strong CP promoter. However, viruses with strong CP promoters sometimes have limited host specificity, e.g., they may be unable to replicate and/or accomplish cell-to-cell movement or systemic movement within certain host plants. It may be desirable, therefore, to base the carrier vector on a viral system with a broad host specificity, so that the high-expressing characteristic of the viral system from which the producer vector is derived may be exploited in a host that is ordinarily inaccessible to that viral system.

This application refers to various patents, patent applications, and publications. The contents of all of these are incorporated herein by reference. In addition, the following publications are incorporated herein by reference: *Current Protocols in Molecular Biology, Current Protocols in Immunology, Current Protocols in Protein Science*, and *Current Protocols in Cell Biology*, all John Wiley & Sons, N.Y., edition as of July 2002; Sambrook, Russell, and Sambrook, *Molecular Cloning: A Laboratory Manual*, $3^{rd}$ ed., Cold Spring Harbor Laboratory Press, Cold Spring Harbor, 2001.

BRIEF DESCRIPTION OF THE DRAWINGS

FIG. 1 shows representative examples of tobamovirus genomes.

FIG. 2 presents a schematic representation of certain families of viruses that infect plants.

FIG. 3 shows a Western blot of protoplasts infected with in vitro transcripts of Av/A4, an AlMV-based vector employed in certain studies described herein (Spitsin, S., et al., *Proc.*

*Natl. Acad. Sci.* 96(5): 2549-2553, 1999). Samples were analyzed 24 hours post inoculation. C– is a negative control. The arrow indicates an AlMV CP band detected by AlMV CP-specific monoclonal antibodies.

FIG. 4 shows pepper plants and *Nicotiana benthamiana* plants infected with wild type AlMV.

FIG. 5 is a Western blot of *N. benthamiana* plants infected with in vitro transcripts of Av/A4. Samples were analyzed 12 days post inoculation. C– is extract from healthy plants. The arrow points to AlMV CP bands detected by AlMV CP-specific monoclonal antibodies.

FIG. 6 presents a schematic diagram of the genomic organization of 125C (FIG. 6A) and D4 following insertion of a polynucleotide of interest (FIG. 6B). The 126/183 kDa protein is required for replication of the virus. The MP is the movement protein that mediates cell-to-cell movement. Arrows indicate positions of the subgenomic promoter. The shaded region represents TMV coat protein sequences that contain a cis element that may be required for optimal replication. The black box represents a polynucleotide of interest, e.g., a foreign gene.

Figure 9:
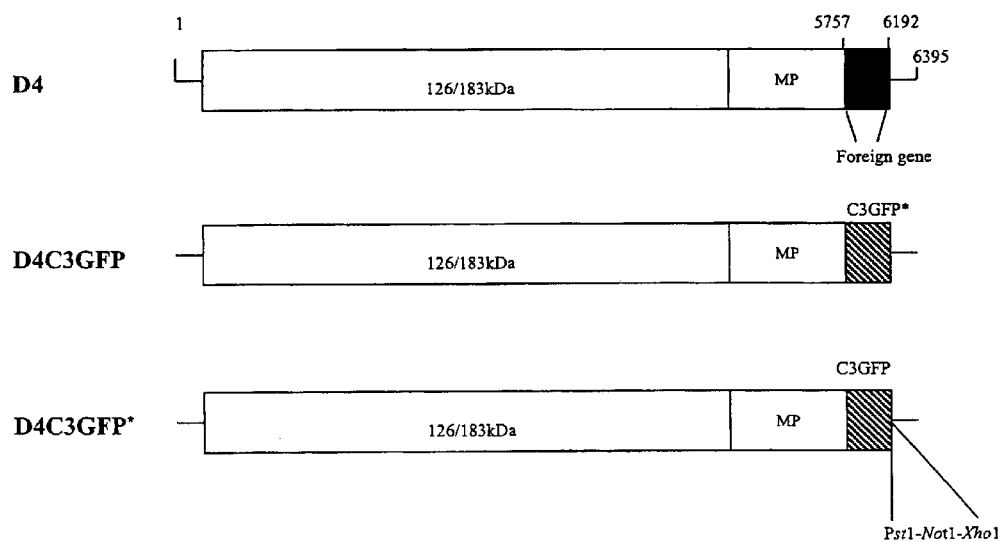

FIG. 9 presents schematics of various D4-related vectors. 126/183 kDa are the replicase proteins, MP is the movement protein required for cell-to-cell movement. Nucleotide numbers represent positions in the wild type TMV genome. C3GFP is the cycle3 mutant of green fluorescent protein (GFP) (Crameri A, Whitehorn E A, Tate E, Stemmer W P, Nat Biotechnol., 14(3): 315-9, 1996). The asterisk indicates mutated C3GFP in which the NcoI site and the XhoI sites in the ORF have been eliminated by mutation using PCR. PstI-XhoI sites were used to introduce sequences from AlMV RNA3 that include the origin of assembly (OAS).

Figure 10:
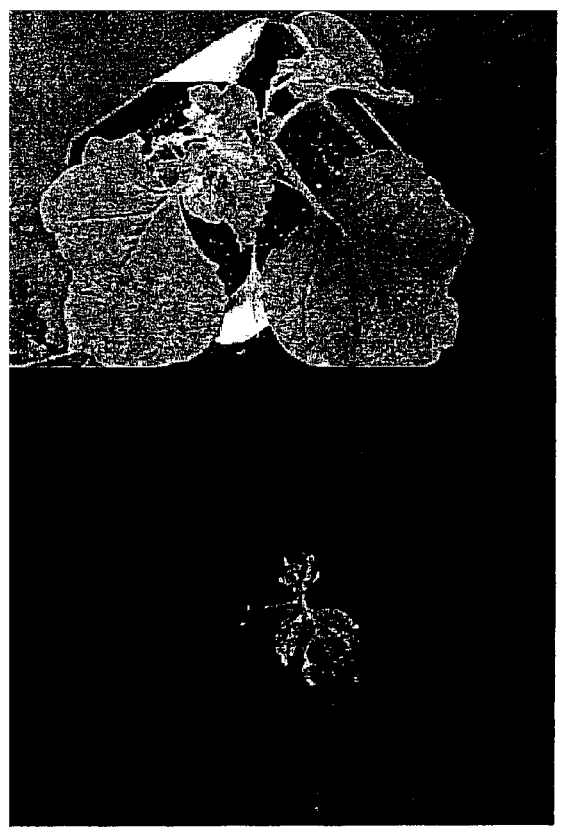

FIG. 10 show pictures of infected plants, demonstrating that AlMV complements D4GFP, which does not have a functional coat protein coding sequence and is limited in systemic spread, and facilitates its movement throughout the plant. FIG. 10 shows a picture of a plant that was co-inoculated with SR27 (a TMV-based vector lacking CP coding sequence and including a GFP transgene under control of the subgenomic CP promoter) and AlMV. The image (taken under UV light) demonstrates spread of virus into the upper un-inoculated leaves. FIG. 10 (taken under UV light) shows a picture of a plant that was inoculated with SR27 only. Lack of fluorescence in the upper leaves indicates that virus infection was limited to locally inoculated leaves. FIG. 10 shows the same plant as in FIG. 10, under normal light.

DEFINITIONS

Gene: For the purposes of the present invention, the term gene has its meaning as understood in the art. In general, a gene is taken to include gene regulatory sequences (e.g., promoters, enhancers, etc.) and/or intron sequences, in addition to coding sequences (open reading frames). It will further be appreciated that the definition of gene can include nucleic acids that do not encode proteins but rather provide templates for transcription of functional RNA molecules such as tRNAs, rRNAs, etc. For the purpose of clarity we note that, as used in the present application, the term "gene" generally refers to a nucleic acid that includes a portion that encodes a protein; the term may optionally encompass regulatory sequences such as promoters, enhancers, terminators, etc. This definition is not intended to exclude application of the term "gene" to non-protein coding expression units but rather to clarify that, in most cases, the term as used in this document refers to a protein coding nucleic acid.

Gene product or expression product: A gene product or expression product is, in general, an RNA transcribed from the gene or a polypeptide encoded by an RNA transcribed from the gene. Expression of a gene or a polynucleotide refers to (i) transcription of RNA from the gene or polynucleotide; (ii) translation of RNA transcribed from the gene or polynucleotide, or both (i) and (ii).

Isolated: As used herein, the term "isolated" refers to a compound or entity that is 1) separated from at least some of the components with which it is normally associated (e.g., purified); 2) synthesized in vitro; and/or 3) produced or prepared by a process that involves the hand of man.

Naturally: The term "naturally" or "naturally-occurring", as used herein, refers to processes, events, or things that occur in their relevant form in nature. By contrast, "not-naturally-occurring" refers to processes, events, or things whose existence or form involves the hand of man.

Operably linked: As used herein, operably linked refers to a relationship between two nucleic acid sequences wherein the expression of one of the nucleic acid sequences is controlled by, regulated by, modulated by, etc., the other nucleic acid sequence. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport or localization of a nucleic acid or polypeptide is directed by an operably linked transport or localization sequence; and the post-translational processing of a polypeptide is directed by an operably linked processing sequence. Preferably a nucleic acid sequence that is operably linked to a second nucleic acid sequence is covalently linked, either directly or indirectly, to such a sequence, although any effective three-dimensional association is acceptable. It is noted that a single nucleic acid sequence can be operably linked to multiple other sequences. For example, a single promoter can direct transcription of multiple RNA species.

Polynucleotide of interest: As used herein, the term "polynucleotide of interest" refers to any target sequence to be expressed in plant cells, as described herein. In many embodiments, the polynucleotide of interest will be a protein-coding polynucleotide but may also be a sequence that provides a template for transcription of a structural RNA or an active RNA such as a ribozyme, interfering RNA, etc. Often, the polynucleotide will be a gene that is not expressed in nature in the relevant type of plant cell, or is not expressed at the level that the polynucleotide is expressed when expression is achieved by intervention of the hand of man, as described herein. In certain embodiments of the invention, the polynucleotide comprises gene sequences that are not naturally found in the relevant plant cell at all; often including gene sequences that are naturally found in other cell types or organisms. Alternatively or additionally, a polynucleotide of interest is one that is not naturally associated with the vector sequences with which it is associated according to the present invention. The word polynucleotide is used interchangeably with "nucleic acid" or "nucleic acid molecule" herein.

Self-replicate: As used herein, "self-replicate" refers to the ability of a vector to copy itself inside a host cell. A vector that can "self-replicate" carries sufficient information in its own genetic elements that it does not rely on other genetic elements for its replication. In general, a vector that can self-replicate is one that includes at least one replicase gene such as an RNA polymerase and possibly additional replicase genes such as a helicase, methyltransferase, etc. In certain instances additional sequences, present in cis (i.e., as part of the vector sequence) are required or can facilitate self-replication.

Vector: "Vector" refers to a nucleic acid molecule capable of transporting another nucleic acid to which it has been linked and can include a plasmid, cosmid or viral vector. The vector may be capable of autonomous replication. Alternatively or additionally, a vector may provide one or more components necessary or sufficient for self-replication, or for replication or integration of another piece of nucleic acid. Vectors are typically nucleic acids, and may comprise DNA and/or RNA. Preferred vectors are maintained extrachromosomally.

DETAILED DESCRIPTION OF CERTAIN
PREFERRED EMBODIMENTS OF THE
INVENTION

Inventive Vectors

Figure 2:
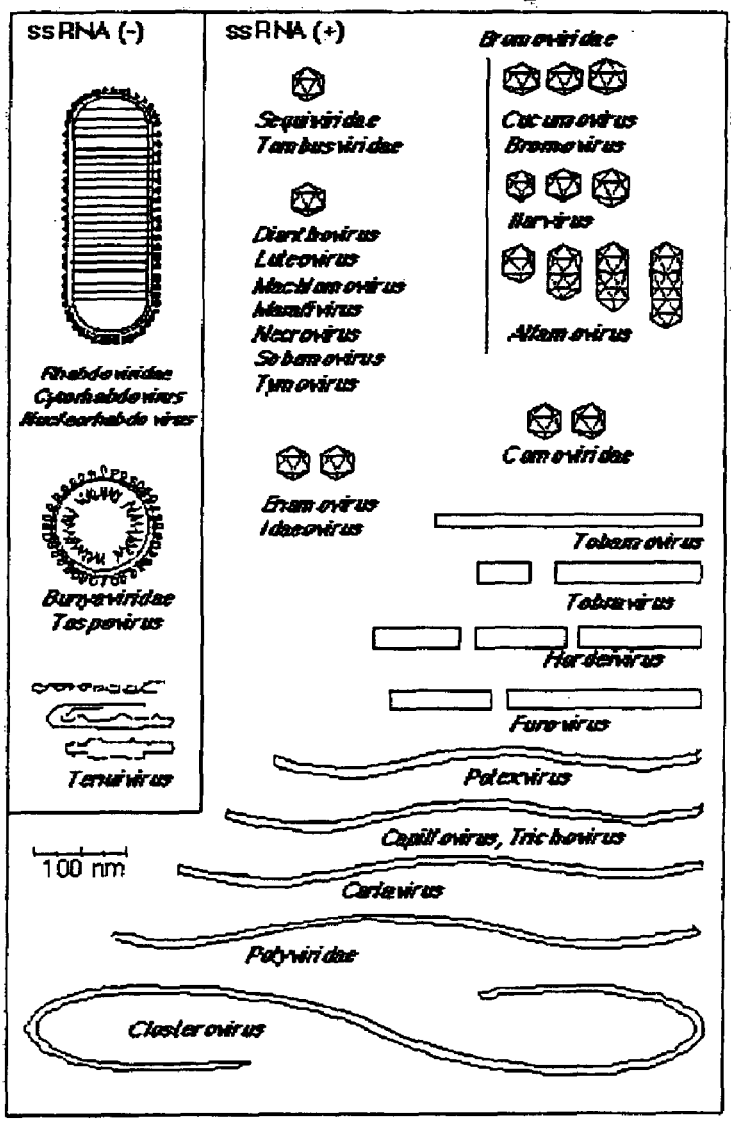
Figure 3:
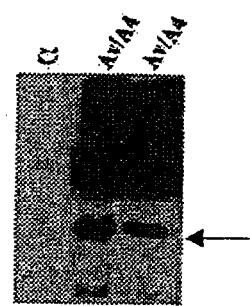

As noted above, the present invention provides systems for expressing a polynucleotide or polynucleotides of interest in plants. In preferred embodiments, these systems include one or more viral vector components. A wide variety of viruses are known that infect various plant species, and can be employed for polynucleotide expression according to the present invention. FIG. 2 presents a schematic representation of certain families of viruses that infect plants. Appendix A provides a representative list of plant virus families, based on the type of nucleic acid (e.g., dsDNA, ssDNA, ssRNA, dsRNA, or unassigned) that makes up the viral genome. Additional information can be found, for example, in *The Classification and Nomenclature of Viruses*, Sixth Report of the International Committee on Taxonomy of Viruses" (Ed. Murphy et al.), Springer Verlag: New York, 1995, the entire contents of which are incorporated herein by reference (see also, Grierson et al., Plant Molecular Biology, Blackie, London, pp. 126-146, 1984; Gluzman et al., *Communications in Molecular Biology: Viral Vectors*, Cold Spring Harbor Laboratory, NY, pp. 172-189, 1988; Mathew, Plant Viruses Online.

In order to enter and infect a plant cell, plant viruses need to cross the cell wall, in addition to protective layers of waxes and pectins. Most or all plant viruses are thought to rely on mechanical breach of the cell wall, rather than on cell-wall-surface receptors, to enter a cell. Such a breach can be caused, for example, by physical damage to the cell, by an organism such as a bacterium, a fungus, a nematode, an insect, or a mite that can deliver the virus. In the laboratory, viruses are typically administered to plant cells simply by rubbing the virus on the plant.

Some plant viruses have segmented genomes, in which two or more physically separate pieces of nucleic acid together make up the plant genome. In some cases, these separate pieces are packaged together in the same viral capsid; in others (i.e., those with multipartite genomes), each genome segment is packaged into its own viral particle. Infection can typically be accomplished by delivery either of plant viral nucleic acid (e.g., RNA) or capsid.

Once the virus has entered (infected) a cell, it typically replicates within the infected cell and then spreads locally (i.e., from cell to cell within leaves that were infected initially). Following local spread, the virus may move into uninfected leaves, e.g., upper leaves of the plant, which is referred to as systemic infection or systemic spread. In general, cell-to-cell spread of many plant viruses requires a functional movement protein while systemic spread requires a functional coat protein (and, generally, also a functional movement protein). In addition to functional movement and coat protein encoding components, viruses may contain additional components that are either required for local or systemic spread or facilitate such spread. These cis-acting components may be either coding or noncoding components. For example, they may correspond to portions of a 3' untranslated region (UTR, also referred to as NTR) of a viral transcript (i.e., they may provide a template for transcription of a 3' untranslated region of a viral transcript). Thus important viral components for infection can be either coding or noncoding regions of a viral genome. By "functional protein encoding component" is meant a polynucleotide comprising a coding portion that encodes a functionally active protein, operably linked to sufficient regulatory elements such as a promoter, so that expression is achieved.

In order to successfully establish either a local (intraleaf) or systemic infection a virus must be able to replicate. Many viruses contain genes encoding one or more proteins that participate in the replication process (referred to herein as replication proteins or replicase proteins). For example, many RNA plant viruses encode an RNA polymerase. Additional proteins may also be required, e.g., helicase or methyltransferase protein(s). The viral genome may contain various sequence components in addition to functional genes encoding replication proteins, which are also required for or facilitate replication.

Any virus that infects plants may be used to prepare a viral vector or vector system in accordance with the present invention. Particularly preferred viruses are ssRNA viruses, most desirably with a (+)-stranded genome. Techniques and reagents for manipulating the genetic material present in such viruses are well known in the art. Typically, for example, a DNA copy of the viral genome is prepared and cloned into a microbial vector, particularly a bacterial vector. Certain ssDNA viruses, including particularly geminiviruses, are also particularly preferred. It will be appreciated that in general the vectors and viral genomes of the invention may exist in RNA or DNA form. In addition, where reference is made to a feature such as a genome or portion thereof of an RNA virus, which is present within a DNA vector, it is to be understood that the feature is present as the DNA copy of the RNA form.

Viruses of a number of different types may be used in accordance with the invention. Preferred viruses include members of the Bromoviridae (e.g., bromoviruses, alfamoviruses, ilarviruses) and Tobamoviridae. Certain preferred virus species include, for example, Alfalfa Mosaic Virus (AlMV), Apple Chlorotic Leaf Spot Virus, Apple Stem Grooving Virus, Barley Stripe Mosiac Virus, Barley Yellow Dwarf Virus, Beet Yellow Virus, Broad Bean Mottle Virus, Broad Bean Wilt Virus, Brome Mosaic Virus (BMV), Carnation Latent Virus, Carnation Mottle Virus, Carnation Ringspot Virus, Carrot Mottle Virus, Cassaya Latent Virus (CLV), Cowpea Chlorotic Mottle Virus, Cowpea Mosaic Virus (CPMV), Cucumber Green Mottle Mosaic Virus, Cucumber Mosaic Virus, Lettuce Infectious Yellow Virus, Maize Chlorotic Mottle Virus, Maize Rayado Fino Virus, Maize Streak Virus (MSV), Parsnip Yellow Fleck Virus, Pea Enation Mosaic Virus, Potato Virus X, Potato Virus Y, Raspberry Bushy Dwarf Virus, Rice Necrosis Virus (RNV), Rice Stripe Virus, Rice Tungro Spherical Virus, Ryegrass Mosaic Virus, Soil-borne Wheat Mosaic Virus, Southern Bean Mosaic Virus, Tobacco Etch Virus (TEV), Tobacco Mosaic Virus (TMV), Tobacco Necrosis Virus, Tobacco Rattle Virus, Tobacco Ring Spot Virus, Tomato Bushy Stunt Virus, Tomato Golden Mosaic Virus (TGMV), and Turnip Yellow Mosaic Virus (TYMV).

Elements of these plant viruses are genetically engineered according to known techniques (see, for example, (see, for example, Sambrook et al., *Molecular Cloning*, 2$^{nd}$ Edition, Cold Spring Harbor Press, NY, 1989; Clover et al., *Molecular Cloning*, IRL Press, Oxford, 1985; Dason et al., *Virology*, 172:285-292, 1989; Takamatsu et al., *EMBO J.* 6:307-311, 1987; French et al., *Science* 231: 1294-1297, 1986; Takamatsu et al., *FEBS Lett*. 269:73-76, 1990; Yusibov and Loesch-Fries, Virology, 208(1): 405-7, 1995. Spitsin et al., Proc Natl Acad Sci USA, 96(5): 2549-53, 1999, etc.) to generate viral vectors for use in accordance with the present invention. According to the present invention, at least two vectors are employed, one or both of which are incapable of systemic infection, but which together provide all functions needed to support systemic infection of at least one of the vectors and allow expression of a polynucleotide of interest throughout the plant. Thus the invention provides the recognition that viral components can complement each other in trans, to provide systemic infection capability.

In particular, according to the invention, a producer vector is prepared. This vector includes a polynucleotide of interest under control of regulatory sequences that direct expression in the relevant plant host. In preferred embodiments, the polynucleotide is placed under control of a viral promoter, for example the CP promoter. For instance, it will often be desirable to replace the natural viral CP gene with the polynucleotide of interest. The producer vector lacks one or more components required for systemic movement. For example, in certain preferred embodiments of the invention the producer vector does not contain sequences sufficient for expression of functional CP (e.g., a CP gene), but may include a gene encoding a cell-to-cell movement protein. The producer vector may contain one or more sequence elements, e.g., an origin of assembly, that may be required in cis to facilitate spread of the virus when present in cis. For example, the producer vector may contain an origin of assembly that is needed for or facilitates activity of a CP, either from the same type of virus as the producer virus or from another virus. Such sequence elements may comprise a recognition site for a CP. In other embodiments of the invention the producer vector may lack sequences sufficient for expression of functional MP and/or replicase proteins. In these embodiments of the invention the producer vector may or may not lack sequences sufficient for expression of functional CP.

According to the invention, a carrier vector is also prepared. This vector complements the producer vector, i.e., it provides components needed for systemic infection that are missing in the producer vector. For example, certain preferred carrier vectors include a functional coat protein encoding component. These carrier vectors are suitable for complementing a producer vector that lacks a functional coat protein encoding component. The carrier vector may lack at least one viral component (e.g., a gene encoding a replicase or movement protein) required for successful systemic infection of a plant, provided that such component is not also absent in the producer vector. The carrier vector may include a polynucleotide of interest (which may be the same as or different from the polynucleotide of interest in the producer vector). In such cases it may be desirable to use a carrier vector that is defective for systemic infection, e.g., because it lacks one or more necessary cis-acting sequences, in order to minimize spread of the recombinant carrier vector to non-target plants.

The carrier vector may (but need not) include a cell-to-cell movement component (e.g., a gene encoding a cell-to-cell movement protein or a noncoding component that is needed for cell-to-cell movement) and/or may lack one or more replicase protein encoding components. In those embodiments of the invention in which the carrier vector does not include a cell-to-cell movement component (e.g., a functional MP encoding portion), such a component should be included in the producer vector.

A complete inventive vector set includes all components necessary for successful systemic viral infection and expression of a polynucleotide of interest. The term "component" is intended to include both protein coding sequences and non-coding sequences such as cis-acting sequences (e.g., promoters, origin of assembly, portions corresponding to untranslated regions in mRNA). Different vectors, or vector elements, may be derived from different plant viruses (see, for example, Examples 1 and 4). In fact, as discussed herein, it will often be desirable to prepare inventive vectors from elements of different viruses in order to take advantage of different viral characteristics (e.g., host range, promoter activity level, virion dimensions, etc.).

In one particularly preferred embodiment of the invention, a producer vector is provided that includes a polynucleotide of interest, a replicase gene, and a movement protein gene and lacks a functional coat protein encoding component, and a carrier vector is provided that expresses a coat protein gene. For example, as described in more detail in the Examples, a producer vector may comprise a TMV-based vector in which the TMV CP coding sequence has been replaced by a polynucleotide of interest, under control of the TMV CP promoter. This producer vector is unable to move systemically. A wild type AlMV vector can serve as the carrier vector. The AlMV vector comprises a functional coat protein encoding component. Co-infection with both producer and carrier vectors allows the CP produced from the AlMV vector CP coding sequence to complement the TMV-based vector, resulting in systemic movement of the TMV-based vector and expression of the polynucleotide in leaves that were not initially infected. Alternately, an AlMV-based vector in which one or more viral components other than those required for expression of AlMV CP has been removed can be used (e.g., an AlMV-based vector lacking functional MP or replication protein coding components), provided that functional CP coding sequences and an operably linked promoter are present. The CP can be from AlMV or from another virus.

In certain embodiments of the invention the CP allows for systemic movement of the carrier vector, while in other embodiments a CP is selected that does not allow for systemic movement of the carrier vector but does allow for systemic movement of the producer vector. In those embodiments of the invention in which the carrier vector lacks one or more of the viral components other than those required for expression of AlMV CP, the producer vector may complement the carrier vector, i.e., the producer vector may supply a component such as a functional MP or replicase protein coding sequence that allows for cell-to-cell movement or replication, respectively, of the carrier vector (and, preferably, also the producer vector). It will be appreciated that where either the producer or the carrier is lacking a replication protein encoding component (e.g., a functional RNA polymerase coding component) and the other vector (carrier or producer, respectively) supplies the missing component, it will often be desirable to insert a promoter (e.g., a genomic promoter) from the vector that supplies the functional replication component into the vector lacking the functional replication protein coding component in order to achieve effective trans-complementation of replication function.

Another example of a preferred inventive viral vector system includes a producer vector in which a polynucleotide of interest is inserted into an AlMV vector, replacing the native AlMV CP encoding component. The polynucleotide of interest is placed under control of the AlMV CP promoter. This producer vector is incapable of systemic infection since it lacks CP but is able to replicate and move cell-to-cell within an infected leaf. The system also includes a cauliflower mosaic virus (CMV)-based carrier vector in which an AlMV CP encoding portion, with or without the AlMV CP 3' UTR is inserted into a CMV vector, replacing the CMV CP encoding component found in the genome of naturally occurring CMV. The AlMV CP encoding component is placed under control of the CMV CP promoter. This vector expresses AlMV CP. Co-infection with the producer and carrier vectors allows CP expressed from the carrier vector to trans-complement the producer vector's lack of functional CP encoding components, allowing systemic movement of the producer vector. The AlMV CP also allows systemic movement of the carrier vector.

In certain embodiments of the invention it is desirable to insert a portion of coding or noncoding sequence from the carrier vector into the producer vector, or vice versa. For example, certain sequences may enhance replication or facilitate cell-to-cell or long distance movement. In particular, certain sequences may serve as recognition sites for formation of a complex between a viral transcript and a CP (e.g., an origin of assembly). In such a case, if systemic movement of a first viral vector is to be achieved using CP provided in trans from a second viral vector, it may be desirable to insert such sequences from the second viral vector that facilitate activity of the CP into the first viral vector. Such sequences may comprise, for example, part or all of a viral transcript 3' UTR. As described in Example 4, in certain embodiments of the invention part or all of the RNA3 3' UTR of AlMV is inserted into a different viral vector, e.g., a TMV-based vector. Including this component in the TMV-based vector facilitates the ability to AlMV CP to trans-complement a TMV-based vector that lacks a functional TMV CP encoding portion. It will be appreciated that this general principle may be applied to any viral vector system comprising trans-complementing vectors, e.g. trans-complementing producer and carrier vector systems.

As will be appreciated by those of ordinary skill in the art, so long as a vector set includes a producer vector that is incapable of systemic viral infection (i.e., lacking one or more functional replication protein, movement protein, or coat protein encoding components) and a carrier vector that provides the function(s) lacking in the producer vector, that set is appropriate for use in accordance with the present invention. In certain embodiments of the invention no individual vector is capable of systemic viral infection but, as a set, one or both of the vectors is competent for such infection and expression of the polynucleotide of interest. Such a system offers a number of advantages. For example, it will be appreciated that if the producer vector infects a plant in the absence of the carrier vector, no systemic infection will result. This diminishes the risk that the polynucleotide of interest will be expressed in unintended (non-target) plants, even of the same species as the target plant. In particular, if the carrier vector is not competent for replication or cell-to-cell movement (because it lacks a component required for replication or cell-to-cell movement) or if it is incompetent for systemic infection (e.g., because it lacks a cis-acting sequence such as an origin of assembly that is required for long distance movement), the likelihood that both producer and carrier vectors will co-infect an unintended plant host are greatly reduced.

Generally, in order to preserve viral function and also simply for ease of genetic manipulation, inventive vectors will be prepared by altering an existing plant virus genome, for example by removing particular genes and/or by disrupting or substituting particular sequences so as to inactivate or replace them. In such circumstances, the inventive vectors will show very high sequence identity with natural viral genomes. Of course, completely novel vectors may also be prepared, for example, by separately isolating individual desired genetic elements and linking them together, optionally with the inclusion of additional elements. Also, it should be noted that where a particular vector is said to lack a given gene, protein, or activity (e.g., the producer vector lacks a coat protein gene), it is sufficient if no such protein or activity is expressed from the vector under conditions of infection, even though the vector may still carry the relevant coding sequence. In general, however, it is typically desirable to remove the relevant coding sequences from the vector.

Analogously, when an inventive vector is said to affirmatively express a particular protein or activity, it is not necessary that the relevant gene be identical to the corresponding gene found in nature. For instance, it has been found that the coat protein can sometimes tolerate small deletions (see, for example WO 00/46350, incorporated herein by reference). So long as the protein is functional, it may be used in accordance with the present invention. Very high sequence identity with the natural protein, however, is generally preferred. For instance, large deletions (e.g., greater than about 25 amino acids) should generally be avoided according to certain embodiments of the invention. Typically, viral proteins expressed in accordance with the present invention will show at least 50%, preferably 60%, 70%, 80%, 85%, 90%, 91%, 92%, 93%, 94%, 95%, 96%, 97%, 98%, or 99% sequence identity with the corresponding natural viral protein. More particularly, the inventive viral protein should typically show 100% identity with critical functional portions (typically of at least several amino acids, often of at least 10, 20, 30, 40, 50 or more amino acids) of the relevant natural viral protein.

It is noted that in the case of many proteins a number of amino acid changes can be made without significantly affecting the functional activity and/or various other properties of the protein such as stability, etc. In particular, many proteins tolerate conservative amino acid changes, i.e., the substitution of an amino acid with a different amino acid having similar properties (conservative substitution) at many positions without significant reduction in activity. Conservative amino acid substitution is well known in the art and represents one approach to obtaining a polypeptide having similar or substantially similar properties to those of a given polypeptide while altering the amino acid sequence. In general, amino acids have been classified and divided into groups according to (1) charge (positive, negative, or uncharged); (2) volume and polarity; (3) Grantham's physico-chemical distance; and combinations of these. See, e.g., Zhang, J., *J. Mol. Evol.*, 50: 56-68, 2000; Grantham R., *Science*, 85: 862-864, 1974; Dagan, T., et al., *Mol. Biol. Evol.*, 19(7), 1022-1025, 2002; *Biochemistry*, 4th Ed., Stryer, L., et al., W. Freeman and Co., 1995; and U.S. Pat. No. 6,015,692. For example, amino acids may be divided into the following 6 categories based on volume and polarity: special (C); neutral and small (A, G, P, S, T); polar and relatively small (N, D, Q, E), polar and relatively large (R, H, K), nonpolar and relatively small (I, L, M, V), and nonpolar and relatively large (F, W, Y). A conservative amino acid substitution may be defined as one that replaces one amino acid with an amino acid in the same group. Thus a variety of functionally equivalent proteins can be derived by making one or more conservative amino acid substitutions in a given viral protein.

Plants

Any plant susceptible to viral infection may be utilized in accordance with the present invention. In general, it will often be desirable to utilize plants that are amenable to growth under defined conditions, for example in a greenhouse and/or in aqueous systems. It may also be desirable to select plants that are not typically consumed by human beings or domesticated animals and/or are not typically part of the human food chain, so that they may be grown outside without concern that the expressed polynucleotide may be undesirably ingested. In other embodiments, however, it will be desirable to employ edible plants.

Often, certain desirable plant characteristics will be determined by the particular polynucleotide to be expressed. To give but a few examples, when the polynucleotide encodes a protein to be produced in high yield (as will often be the case, for example, when therapeutic proteins are to be expressed), it will often be desirable to select plants with relatively high biomass (e.g., tobacco, which has the additional advantages that it is highly susceptible to viral infection, has a short growth period, and is not in the human food chain). Where the polynucleotide encodes a protein whose full activity requires (or is inhibited by) a particular post-translational modification, the ability (or inability) of certain plant species to accomplish the relevant modification (e.g., a particular glycosylation) may direct selection.

In certain preferred embodiments of the invention, crop plants, or crop-related plants are utilized. In some particularly preferred embodiments, edible plants are utilized.

Preferred plants for use in accordance with the present invention include Angiosperms, Bryophytes (e.g., Hepaticae, Musci, etc.), Pteridophytes (e.g., ferns, horsetails, lycopods), Gymnosperms (e.g., conifers, cycase, Ginko, Gnetales), and Algae (e.g., Chlorophyceae, Phaeophyceae, Rhodophyceae, Myxophyceae, Xanthophyceae, and Euglenophyceae). Particularly preferred are members of the family Leguminosae (Fabaceae; e.g., pea, alfalfa, soybean); Gramineae (Poaceae; e.g., corn, wheat, rice); Solanaceae, particularly of the genus *Lycopersicon* (e.g., tomato), *Solanum* (e.g., potato, eggplant), *Capsium* (e.e., pepper), or *Nicotiana* (e.g., tobacco); Umbelliferae, particularly of the genus *Daucus* (e.g., carrot), *Apium* (e.g., celery), or Rutaceae (e.g., oranges); Compositae, particularly of the genus *Lactuca* (e.g., lettuce); Brassicaceae (Cruciferae), particularly of the genus *Brassica* or *Sinapis*. Particularly preferred Brassicaceae family members include *Brassica campestris, B. carinata, B. juncea, B. napus, B. nigra, B. oleraceae, B. tournifortii, Sinapis alba*, and *Raphanus sativus*.

The inventive system may be employed to infect, and/or to express a polynucleotide in plants at any stage of development including, for example, mature plants, seedlings, sprouts, and seeds. The system may be employed to infect any part of a plant (e.g., roots, leaves, stems, etc.) In particularly preferred embodiments of the invention, the system is used to infect sprouts. Generally, a plant is considered to be a sprout when it is a seedling that does not require external nutrients or energy in the form of light or heat beyond what is required to achieve normal germination temperatures. Often, a seedling that is less than two weeks old, preferably less than 10 days old, is considered to be a sprout.

Polynucleotides of Interest

The teachings of the present invention may be employed to deliver to and/or express in plant cells any polynucleotide of interest. For example, protein-coding polynucleotides may express enzymes, antibodies, hormones, cytokines, regulatory factors, structural proteins, or any other protein or polypeptide of interest. Encoded proteins may be naturally-occurring proteins, or may be designed or engineered proteins, including for instance fusion proteins (e.g., fusion proteins incorporating part or all of a plant virus protein such as MP or CP). In certain embodiments of the invention the polynucleotide of interest comprises a portion encoding a tag, e.g., a 6x-His tag, HA tag, Myc tag, FLAG tag, etc. Such tags may simplify the isolation and/or purification of the protein. In certain embodiments of the invention the tag is a cleavable tag, e.g., a tag cleavable by a protease such as thrombin, so that the tag can readily be removed after purification, resulting in a protein with wild type sequence.

In some instances, it may be desirable to utilize the inventive system to express more than one polypeptide chain in the same host plant (e.g., using two different producer vectors, inserting two different polynucleotides into one producer vector, or inserting one polynucleotide into the producer vector and one into the carrier vector), for example in order to produce a multimeric protein or to simultaneously produce two different proteins).

For instance, in certain preferred embodiments of the invention, the present invention employs a polynucleotide that encodes a therapeutically active protein. Exemplary proteins that have been approved for therapeutic uses include, for example, insulin, human growth hormone, interferons, albumin, tPA, erythropoietin, interleukins, factor VIII, DNase, factor IX, PDGF, FSH, TNF receptor (soluble form), calcitonin, and a variety of immunoglobulins. Of course, the invention is not limited to such approved proteins, but encompasses expression of any polynucleotide(s), whether protein-coding or not, and particularly encompasses expression of any polynucleotide encoding any therapeutically active protein, whether prokaryotic or eukaryotic in origin, etc.

Generally, the pharmaceutical proteins of interest include, but are not limited to, hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, cytokines and immune system proteins (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interfersons, integrins, addressins, seletins, homing receptors, T cell receptors, immunoglobulins, soluble major histocompatibility complex antigens, immunologically active antigens such as bacterial, parasitic, or viral antigens or allergens), autoantigens, antibodies), enzymes (tissue plasminogen activator, streptokinase, cholesterol biosynthestic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases and the like), receptors (steroid hormone receptors, peptide receptors), binding proteins (sterpod binding proteins, growth hormone or growth factor binding proteins and the like), transcription and translation factors, oncoproteins or proto-oncoprotiens (e.g., cell cycle proteins), muscle proteins (myosin or tropomyosin and the like), myeloproteins, neuroactive proteins, tumor growth suppressing proteins (angiostatin or endostatin, both of which inhibit angiogenesis), anti-sepsis proteins (bectericidal permeability-increasing protein), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, Protein C, von Willebrand factor, antithrombin III, glucocerebrosidase, erythropoietin granulocyte colony stimulating factor (GCSF) or modified Factor VIII, anticoagulants such as huridin) and the like.

In one particular example, the present invention may be utilized to produce vaccine components. In general, it is desirable to include in vaccines proteins, or portions of proteins, to which a human or animal immune system is exposed when the human or animal is infected with a pathogen, or suffering some other undesirable event (e.g., development of a tumor). Thus, proteins or polypeptides that may be formulated in a vaccine include, for example, viral coat proteins, viral G proteins, microbial cell wall proteins, microbial toxin proteins, tumor-specific antigens, etc.

In other embodiments, the inventive system may be used to express a polynucleotide encoding an enzyme that synthesizes or modifies a biologically active agent. For instance, certain enzymes (e.g., polyketide synthases, polypeptide synthetases, terpene synthases, etc.) synthesize small molecules with interesting biological activities, including therapeutic activities (e.g., antibiotic, anticancer, immunosuppressive activities, etc.). Also, a large number of enzymes that modify protein or small molecule substrates (e.g., kinases, hydrolases, transferases, etc.) is known. See U.S. Pat. No. 6,500,644 for additional proteins that can be desirably expressed in plants using the inventive systems described herein.

In other embodiments, the inventive system may be used to produce diagnostic or research reagents including, for example, antibodies.

In yet other embodiments, the inventive system may be utilized to produce nutritionally relevant proteins or other products. Nutritionally relevant proteins include, for example, proteins that are found naturally in foods consumed by humans or domesticated animals (e.g., cats, dogs). Other examples include proteins having a balanced amino acid composition, e.g., proteins having a composition such as those used for total parenteral nutrition (TPN), etc.

In still other embodiments, the inventive system may be utilized to express polynucleotides that do not necessarily encode proteins, for example to produce active RNA species, e.g., ribozymes or interfering RNAs that silence gene expression (either long double-stranded RNAs or short interfering RNAs (siRNAs) or short hairpin RNAs (shRNAs). In some embodiments, ribozymes or interfering RNAs may be produced that target plant genes, so that an altered plant is created, for example that does not express a particular receptor for a plant pathogen, or a particular allergenic protein.

Introducing Vectors into Plants

In general, inventive viral vectors may be delivered to plants according to known techniques. For example, the vectors themselves may be directly applied to plants (e.g., via abrasive inoculations, mechanized spray inoculations, vacuum infiltration, particle bombardment, or electroporation). Alternatively, virions may be prepared (e.g., from already infected plants), and may be applied to other plants according to known techniques.

As noted above, in particularly preferred embodiments of the present invention, viral vectors are applied to sprouts (e.g., through infiltration or mechanical inoculation [spray]).

Where infection is to be accomplished by direct application of a viral genome to a plant, any available technique may be used to prepare the genome. For example, many viruses that are usefully employed in accordance with the present invention have ssRNA genomes. ssRNA may be prepared by transcription of a DNA copy of the genome, or by replication of an RNA copy, either in vivo or in vitro. Given the readily availability of easy-to-use in vitro transcription systems (e.g., SP6, T7, reticulocyte lysate, etc.), and also the convenience of maintaining a DNA copy of an RNA vector, it is expected that inventive ssRNA vectors will often be prepared by in vitro transcription, particularly with T7 or SP6 polymerase.

Isolation and/or Formulation of Polynucleotide Expression Products

In many embodiments of the present invention, it will be desirable to isolate polynucleotide expression products from the plant tissues that express them. It may also be desirable to formulate such isolated products for their intended use (e.g., as a pharmaceutical or diagnostic agent, or as a reagent, etc.). In other embodiments, it will be desirable to formulate the products together with some or all of the plant tissues that express them.

Where it is desirable to isolate the expression product from some or all of the plant tissue that expresses it, any available purification techniques may be employed. Those of ordinary skill in the art are familiar with a wide range of fractionation and separation procedures (see, for example, Scopes et al., *Protein Purification: Principles and Practice*, 3$^{rd}$ Ed., Janson et al., *Protein Purification: Principles, High Resolution Methods, and Applications*, Wiley-VCH, 1998; Springer-Verlag, NY, 1993; Roe, *Protein Purification Techniques*, Oxford University Press, 2001, each of which is incorporated herein by reference). Often, it will be desirable to render the product more than about 50%, preferably more than about 60%, 70%, 80%, 85%, 90%, 91%, 92%, 93%, 94%, 95%, 96%, 97%, 98%, or 99% pure.

Where it is desirable to formulate the product together with the plant material, it will often be desirable to have utilized a plant that is not toxic to the relevant recipient (e.g., a human or other animal). Relevant plant tissue (e.g., leaves) may simply be harvested and processed according to techniques known in the art, with due consideration to maintaining activity of the expressed product. In certain embodiments of the invention, it is desirable to have expressed the polynucleotide in an edible plant (and, specifically in edible portions of the plant) so that the material can subsequently be eaten. For instance, where the polynucleotide encodes a nutritionally relevant protein, or a therapeutic protein that is active after oral delivery (when properly formulated), it may be desirable to produce the protein in an edible plant portion, and to formulate the expressed polynucleotide for oral delivery together with the some or all of the plant material with which the polynucleotide was expressed.

Where the polynucleotide encodes or produces a therapeutic agent, it may be formulated according to know techniques. For example, an effective amount of a pharmaceutically active product can be formulated together with one or more organic or inorganic, liquid or solid, pharmaceutically suitable carrier materials. A pharmaceutically active product produced according to the present invention may be employed in dosage forms such as tablets, capsules, troches, dispersions, suspensions, solutions, capsules, creams, ointments, aerosols, powder packets, liquid solutions, solvents, diluents, surface active agents, isotonic agents, thickening or emulsifying agents, preservatives, and solid bindings, as long as the biological activity of the protein is not destroyed by such dosage form.

Materials that can serve as pharmaceutically acceptable carriers include, but are not limited to sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening agents, flavoring agents, and perfuming agents, preservatives, and antioxidants can also be present in the composition, according to the judgment of the formulator (see also *Remington's Pharmaceutical Sciences*, Fifteenth Edition, E. W. martin (Mack Publishing Co., Easton Pa., 1975). For example, the polynucleotide expression product may be provided as a pharmaceutical composition by means of conventional mixing granulating dragee-making, dissolving, lyophilizing, or similar processes.

In certain preferred embodiments, it may be desirable to prolong the effect of a pharmaceutical preparation by slowing the absorption of the pharmaceutically active product (e.g., protein) that is subcutaneously or intramuscularly injected. This may be accomplished by the use of a liquid suspension of crystalline or amorphous material with poor water solubility. The rate of absorption of the product then depends upon its rate of dissolution, which in turn, may depend upon size and form. Alternatively, delayed absorption of a parenterally administered product is accomplished by dissolving or suspending the product in an oil vehicle. Injectable depot forms are made by forming microencapsule matrices of the protein in biodegradable polymers such as polylactide-polyglycolide. Depending upon the ratio of product to polymer and the nature of the particular polymer employed, the rate of release can be controlled. Examples of other biodegradable polymers include poly(orthoesters) and poly(anhydrides). Depot injectable formulations may be prepared by entrapping the product in liposomes or microemulsions, which are compatible with body tissues.

Enterally administered preparations of pharmaceutically active products may be introduced in solid, semi-solid, suspension or emulsion form and may be compounded with any pharmaceutically acceptable carriers, such as water, suspending agents, and emulsifying agents. The expression products may also be administered by means of pumps or sustained-release forms, especially when administered as a preventive measure, so as to prevent the development of disease in a subject or to ameliorate or delay an already established disease.

Pharmaceutically active products, optionally together with plant tissue, are particularly well suited for oral administration as pharmaceutical compositions. Harvested plant material may be processed in any of a variety of ways (e.g., air drying, freeze drying, extraction etc.), depending on the properties of the desired therapeutic product and its desired form. In preferred embodiments, such compositions as described above are ingested orally alone or ingested together with food or feed or a beverage. Compositions for oral administration include infected plants; extractions of the infected plants, and proteins purified from infected plants provided as dry powders, foodstuffs, aqueous or non-aqueous solvents, suspensions, or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medial parenteral vehicles including sodium chloride solution, Ringer's dextrose solution, dextrose plus sodium chloride solution, Ringer's solution containing lactose or fixed oils. Examples of dry powders include any infected plant biomass that has been dried, for example, freeze dried, air dried, or spray dried. For example, the plants may be air dried by placing them in a commercial air dryer at about 120 degrees Fahrenheit until the biomass contains less than 5% moisture by weight. The dried plants may be stored for further processing as bulk solids or further processed by grinding to a desired mesh sized powder. Alternatively, freeze-drying may be used for products that are sensitive to air-drying. Products may be freeze dried by placing them into a vacuum drier and dried frozen under a vacuum until the biomass contains less than about 5% moisture by weight. The dried material can be further processed as described herein.

Infected plants of the present invention may be administered as or together with one or more herbal preparations. Useful herbal preparations include liquid and solid herbal preparations. Some examples of herbal preparations include tinctures, extracts (e.g., aqueous extracts, alcohol extracts), decoctions, dried preparations (e.g., air-dried, spray dried, frozen, or freeze-dried), powders (e.g., lyophilized powder), and liquid. Herbal preparations can be provided in any standard delivery vehicle, such as a capsule, tablet, suppository, liquid dosage, etc. Those skilled in the art will appreciate the various formulations and modalities of delivery of herbal preparations that may be applied to the present invention.

Those skilled in the art will also appreciate that a particularly preferred method of obtaining the desired pharmaceutically active products is by extraction. Infected plants may be extracted to remove the desired products from the residual biomass, thereby increasing the concentration and purity of the product. Plants may also be extracted in a buffered solution. For example, the fresh harvested plants may be transferred into an amount of ice-cold water at a ratio of one to one by weight that has been buffered with, e.g., phosphate buffer. Protease inhibitors can also be added as required. The plants can be disrupted by vigorous blending or grinding while suspended in the buffer solution and the extracted biomass removed by filtration or centrifugation. The transgene product carried in solution can be further purified by additional steps or converted to a dry powder by freeze-drying or precipitation. Extraction can also be carried out by pressing. Live plants can also be extracted by pressing in a press or by being crushed as they are passed through closely spaced rollers. The fluids expressed from the crushed plants are collected and processed according to methods well known in the art. Extraction by pressing allows the release of the products in a more concentrated form. However, the overall yield of the product may be lower than if the product were extracted in solution.

Inventive infected plants, extractions, powders, dried preparations and purified protein products, etc., can also be in encapsulated form with or without one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active product may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

In other particularly preferred embodiments, an infected plant expressing a pharmaceutically active product according to the present invention, or biomass of an infected plant, is administered orally as medicinal food. Such edible compositions are consumed by eating raw, if in a solid form, or by drinking, if in liquid form. In a preferred embodiment, the transgenic plant material is directly ingested without a prior processing step or after minimal culinary preparation. For example, the pharmaceutically active protein is expressed in a sprout of which can be eaten directly. For example, the polynucleotide is expressed in an alfalfa sprout, mung bean sprout, or spinach or lettuce leaf sprout, etc. In an alternative embodiment, the plant biomass is processed and the material recovered after the processing step is ingested.

Processing methods preferably used in the present invention are methods commonly used in the food or feed industry. The final products of such methods still include a substantial amount of the expressed pharmaceutically active polynucleotide and are preferably conveniently eaten or drunk. The final product may also be mixed with other food or feed forms, such as salts, carriers, favor enhancers, antibiotics, and the like, and consumed in solid, semi-solid, suspension, emulsion, or liquid form. In another preferred embodiment, such methods include a conservation step, such as, e.g., pasteurization, cooking, or addition of conservation and preservation agents. Any plant is used and processed in the present invention to produce edible or drinkable plant matter. The amount of pharmaceutically active polynucleotide expression product in an edible or drinkable sprout preparation may be tested by methods standard in the art, e.g., gel electrophoresis, ELISA, or Western blot analysis, using an antibody specific for the product. This determination may be used to standardize the amount of protein ingested. For example, the amount of therapeutically active product in a sprout juice determined and regulated, for example, by mixing batches of product having different levels of protein so that the quantity of juice to be drunk to ingest a single dose can be standardized. The contained, regulatable environment of the present invention, however, should minimize the need to carry out such standardization procedures.

A pharmaceutically active protein produced in an infected plant and eaten by a host is absorbed by the digestive system. One advantage of the ingestion of infected plant tissue that has been only minimally processed, is to provide encapsulation or sequestration of the protein in cells of the plant. Thus, the protein may receive at least some protection from digestion in the upper digestive tract before reaching the gut or intestine and a higher proportion of active would be available for uptake.

The pharmaceutical compositions of the present invention can be administered therapeutically or prophylactically. In certain preferred embodiments, the compositions may be used to treat or prevent a disease. For example, any individual who suffers from a disease or who is at risk of developing a disease may be treated. It will be appreciated that an individual can be considered at risk for developing a disease without having been diagnosed with any symptoms of the disease. For example, if the individual has a particular genetic marker identified as being associated with increased risk for developing a particular disease, that individual will be considered at risk for developing the disease. Similarly, if members of an individual's family have been diagnosed with a particular disease, e.g., cancer, the individual may be considered to be at risk for developing that disease.

Liquid dosage forms for oral administration include, but are not limited to, pharmaceutically acceptable emulsions, microemulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Compositions for rectal or vaginal administration are preferably suppositories which can be prepared by mixing the compositions of this invention with suitable non-irritating excipients or carriers such as cocoa butter, polyethylene glycol or a suppository wax which are solid at ambient temperature but liquid at body temperature and therefore melt in the rectum or vaginal cavity and release the active protein.

Dosage forms for topical or transdermal administration of a pharmaceutical composition of this invention include ointments, pastes, creams, lotions, gels, powders, solutions, sprays, inhalants or patches. The active product, or preparation thereof, is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a pharmaceutically active protein to the body. Such dosage forms can be made by suspending or dispensing the pharmaceutically active product in the proper medium. Absorption enhancers can also be used to increase the flux of the pharmaceutically active protein across the skin. The rate can be controlled by either providing a rate controlling membrane or by dispersing the pharmaceutically active protein in a polymer matrix or gel.

The compositions are administered in such amounts and for such time as is necessary to achieve the desired result. As described above, in certain embodiments of the present invention a "therapeutically effective amount" of a pharmaceutical composition is that amount effective for treating, attenuating, or preventing a disease in a host. Thus, the "amount effective to treat, attenuate, or prevent disease", as used herein, refers to a nontoxic but sufficient amount of the pharmaceutical composition to treat, attenuate, or prevent disease in any host. As but one example, the "therapeutically effective amount" can be an amount to treat, attenuate, or prevent diabetes.

The exact amount required will vary from subject to subject, depending on the species, age, and general condition of the subject, the stage of the disease, the particular pharmaceutical mixture, its mode of administration, and the like. The infected plants of the invention and/or protein preparations thereof are preferably formulated in dosage unit form for ease of administration and uniformity of dosage. The expression "dosage unit form," as used herein, refers to a physically discrete unit of pharmaceutically active polynucleotide expression product appropriate for the patient to be treated. It will be understood, however, that the total daily usage of the compositions of the present invention is preferably decided by an attending physician within the scope of sound medical judgment. The specific therapeutically effective dose level for any particular patient or organism may depend upon a variety of factors including the disorder being treated and the severity of the disorder; the activity of the specific compound employed; the specific composition employed; the age, body weight, general health, sex of the patient, diet of the patient, pharmacokinetic condition of the patient, the time of administration, route of administration, and rate of excretion of the specific compound employed; the duration of the treatment; drugs used in combination or coincidental with the specific compound employed; and like factors well known in the medical arts.

It will also be appreciated that the pharmaceutical compositions of the present invention can be employed in combination therapies, that is, the pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-cancer agent), or they may achieve different effects.

EXEMPLIFICATION

Example 1

Construction of Inventive Vectors

We have prepared vector systems that include components of two heterologous plant viruses in order to achieve a system that readily infects a wide range of plant types and yet poses little or no risk of infectious spread. In certain preferred embodiments, this system includes components from Alfalfa Mosaic Virus (AlMV) and Tobacco Mosaic Virus (TMV).

AlMV is an Alfamovirus, closely related to the Ilarvirus group and is a member of the Bromoviridae family. The genome of AlMV consists of three positive-sense RNAs (RNAs 1-3) (See Appendix H, which presents accession codes for a variety of AlMV genome sequences). RNAs 1 and 2 encode replicase proteins P1 and P2, respectively; RNA3 encodes the cell-to-cell movement protein P3. A subgenomic RNA, RNA4, is synthesized from RNA3. This subgenomic RNA4 encodes the viral coat protein (CP). CP participates in viral genome activation to initiate infection, RNA replication, viral assembly, viral RNA stability, long-distance movement of viral RNA, and symptom formation. AlMV depends on a functional P3 protein for cell-to-cell movement, and requires the CP protein throughout infection. Depending on the size of the CP-encapsidated viral RNA, virions of AlMV can vary significantly in size (e.g., 30- to 60-nm in length and 18 nm in diameter) and form (e.g., spherical, ellipsoidal, or bacilliform). The host range of AlMV is remarkably wide and includes the agriculturally valuable crops alfalfa (*Medicago sativa*), tomato (*Lycopersicon esculentum*), lettuce (*Lactuca sativa*), common bean (*Phaseolus vulgaris*), potato (*Solanum tuberosum*), white clover (*Trifolium repens*) and soybean (*Glycine max*). Particular susceptible host species include, for example, *Abelmoschus esculentus, Ageratum conyzoides, Amaranthus caudatus, Amaranthus retroflexus, Antirrhinum majus, Apium graveolens, Apium graveolens* var. *rapaceum, Arachis hypogaea, Astragalus glycyphyllos, Beta vulgaris, Brassica campestris* ssp. *rapa, Calendula officinalis, Capsicum annuum, Capsicum frutescens, Caryopteris incana, Catharanthus roseus, Celosia argentea, Cheiranthus cheiri, Chenopodium album, Chenopodium amaranticolor, Chenopodium murale, Chenopodium quinoa, Cicer arietinum, Cichorium endiva, Coriandrum sativum, Crotalaria spectabilis, Cucumis melo, Cucumis sativus, Cucurbita pepo, Cyamopsis tetragonoloba, Daucus carota* (var. *sativa*), *Dianthus barbatus, Dianthus caryophyllus, Emilia sagittata, Fagopyrum esculentum, Gomphrena globosa, Helianthus annuus, Lablab purpureus, Lathyrus odoratus, Lens culinaris, Linum usitatissimum, Lupinus albus, Macroptilium lathyroides, Malva parviflora, Matthiola incana, Medicago hispida, Melilotus albus, Nicotiana bigelovii, Nicotiana clevelandii, Nicotiana debneyi, Nicotiana glutinosa, Nicotiana megalosiphon, Nicotiana rustica, Nicotiana sylvestris, Nicotiana tabacum, Ocimum basilicum, Petunia x hybrida, Phaseolus lunatus, Philadelphus, Physalis floridana, Physalis peruviana, Phytolacca americana, Pisum sativum, Solanum demissum, Solanum melongena, Solanum nigrum, Solanum nodiflorum, Solanum rostratum, Sonchus oleraceus, Spinacia oleracea, Stellaria media, Tetragonia tetragonioides, Trifolium dubium, Trifolium hybridum, Trifolium incarnatum, Trifolium pratense, Trifolium subterraneum, Tropaeolum majus, Viburnum opulus, Viciafaba, Vigna radiata, Vigna unguiculata, Vigna unguiculata* ssp. *sesquipedalis*, and *Zinnia elegans*.

Figure 1:
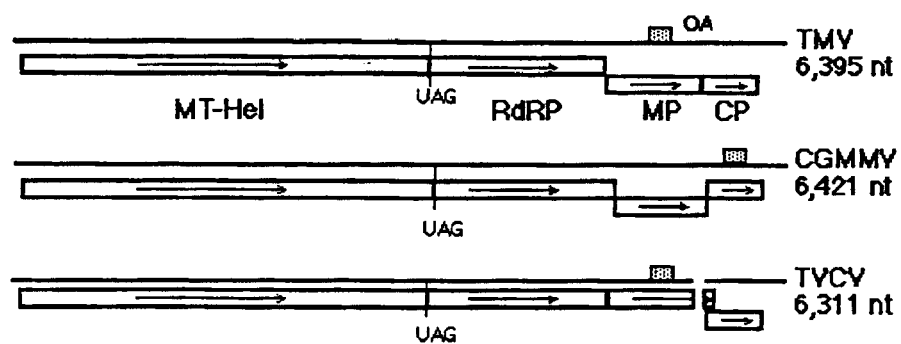

TMV is the type member of the tobamovirus group. Tobamoviruses have single-(+)-stranded RNA genomes, and produce rod-shaped virions consisting of the RNA genome and coat protein (CP) polypeptides. Tobamovirus genomes encode 4-5 polypeptides. Two of the polypeptides are translated from the same 5'-proximal initiation codon and function in viral replication. These polypeptides include an RNA-dependent RNA polymerase. In addition, polypeptides having methyltransferase and RNA helicase activity are typically encoded. The other encoded proteins typically include a movement protein and the coat protein, each of which is translated from a separate subgenomic RNA. Representative examples of tobamovirus genomes are depicted in FIG. 1.

The TMV genome is 6395 nucleotides long and is encapsidated with a 17.5 kD CP, which produces 300 nm-long rods. In addition to CP, TMV has three nonstructural proteins: 183 and 126 kD proteins are translated from genomic RNA and are required for viral replication. The 30 kD movement protein provides for the transfer of viral RNA from cell-to-cell. A representative list of accession codes for TMV genome sequence information is included as FIG. 2; Appendices B-F show sequence alignments for the tobamovirus helicase, RNA-dependent RNA polymerase (a replicase), movement protein, coat protein, and methyltransferase genes, respectively, from various tobamoviruses. Plant species susceptible to infection with TMV include *Beta vulgaris, Capsicum frutescens, Chenopodium amaranticolor, Chenopodium hybridum, Chenopodium quinoa, Cucumis melo, Cucumis sativus, Cucurbita pepo, Datura stramonium, Lactuca sativa, Lucopersicon esculentum, Lycopersicon pimpinellifolium, Nicotiana benthamiana, Nicotiana bigelovii, Nicotiana clevelandii, Nicotiana debneyi, Nicotiana glutinosa, Nicotiana rustica, Nicotiana sylvestris, Nicotiana tabacum, Papaver nudicaule, Phaseolus vulgaris, Physalis floridana, Physalis peruviana*, and *Solanum tuberosum*.

According to certain embodiments of the present invention, a replication-competent version of either the AlMV or the TMV is generated that lacks long distance mobility but includes a polynucleotide to be expressed in plant tissues, preferably under control of the CP promoter (e.g., in place of the CP gene, so that CP is not functional) as the producer vector. If plants are inoculated with this vector alone, its infection is limited to local tissues (i.e., to cells within the initially infected leaf).

This replication-competent producer vector is administered together with a separate carrier vector bearing a functional CP. Preferably, transcripts of these two vectors are mixed with one another and are mechanically applied to plant leaves. In other embodiments of the invention described in the detailed description, the carrier vector is incompetent for replication so that no systemic infection results. The producer vector replicates and provides replicase for trans-replication of the replication-defective carrier vector. Replication of (infection with) the producer vector results in the production of the polynucleotide expression product. Replication of the carrier vector provides CP, which supports the movement of both vectors into the upper un-inoculated leaves. Preferably, integration of the vectors into the host genome is avoided, so that transgenic plants are not produced, and the risk that genetic alterations are introduced into the environment is minimized.

We have constructed a vector based on the Tobacco Mosaic Virus that is adapted for insertion of a polynucleotide of interest to generate a producer vector according to the present invention. Specifically, we have generated vectors that are deficient in CP production (see FIGS. 8 and 11; vector D4 is represented with a generic polynucleotide inserted; vector SR-27 and related vectors are derived from D4 as described further in Example 4). We have demonstrated that infection with such vectors is limited to locally inoculated leaves. These vectors depends upon a second vector for systemic movement.

We have used a protoplast system to test vector replication, replication-dependent stability, and efficacy of protein production. We have also inoculated *Nicotiana benthamiana* plants to test the cell-to cell movement and stability of the vector, and have demonstrated systemic infection when this vector is administered together with a wild type AlMV vector including an AlMV CP gene.

Figure 5:
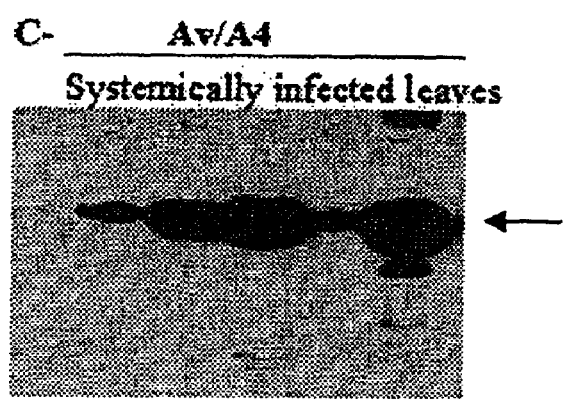

An AlMV-based vector referred to as Av/A4, which contains a functional AlMV coat protein gene, has been constructed. As shown in FIG. 5, we have established a tobacco protoplast system and tested the components of this vector. Depicted is a Western blot showing accumulation of virus coat protein, indicating infection of protoplasts and verifying that we are able to reliably detect expression of CP in our protoplast system.

Figure 6:
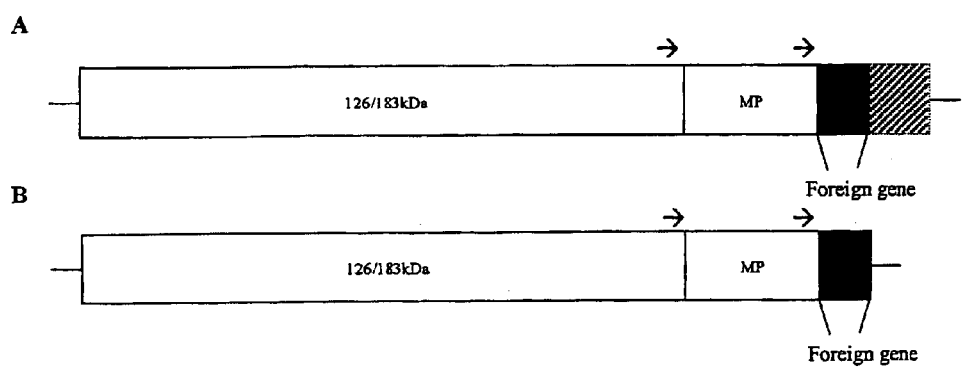
Figure 7:
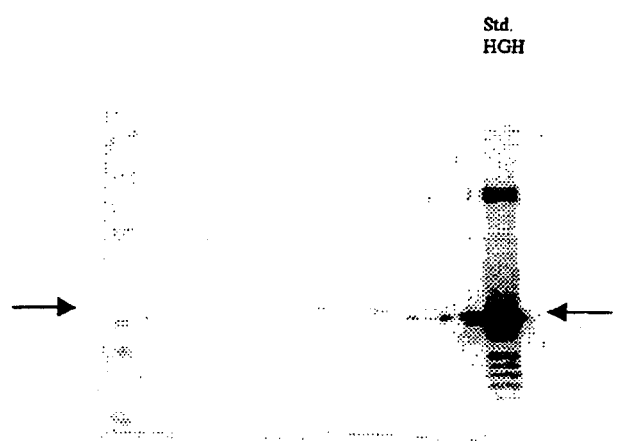
FIG. 7 shows a Western blot of protoplasts infected with in vitro synthesized transcripts of 125C/hGH (125C as shown in FIG. 6A, in which the foreign gene encodes hGH). Samples were analyzed 24 hours post inoculation. 1 ug of purified hGH was loaded as a standard.

As shown in FIGS. 6 and 7, we have successfully infected two host plant species, *Nicotiana benthamiana* and pepper plants. FIG. 6 shows the infected plants; FIG. 7 shows a Western blot of upper leaves (not initially infected) analyzed 12 days after inoculation. AlMV CP protein is readily detectable, indicating that we are able to reliably detect expression of CP in infected plant hosts.

Example 2

Expression of a Polynucleotide Encoding Human Growth Hormone

Figure 8:
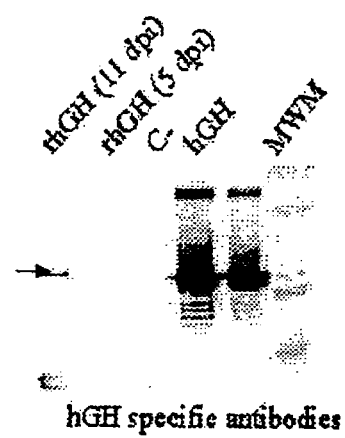
FIG. 8 is a Western blot showing detection of hGH in *N. benthamiana* plants 11 days post infection (dpi).

FIG. 8 shows two TMV-based vectors, 125C and D4, that were engineered to accept insertion of a polynucleotide of interest, following insertion of the polynucleotide (indicated as "foreign gene"). 125C includes TMV coat protein sequences (i.e. sequences extending downstream from nucleotide 5757 of the TMV genome) that contain a cis element that may be required for optimal replication. We inserted the gene for human growth hormone (hGH) into each of these vectors between the Pac1 and Xho1 sites. An AUG was introduced in the 5' primer used to amplify the gene from a plasmid, and the amino acids KDEL were introduced at the 3' end of the coding sequence in order to enhance translation due to retention in the ER. HGH was cloned with and without its native leader sequence; hGH2 lacks the leader and hGH4 includes the leader.

Primer SR22 (5'-CCG TTAATTAATG TTC CCA ACT ATT CCA) was used to clone hGH without its leader, and introducing a Pac1 site at the 5' end; primer SR23 (5'-CCG TTAATTAATG GCA ACT GGA TCA AGG) was used to clone hGH with its leader. Primer SR24 (5'-CGG CTC GAG TTA AAA ACC ACA TGA) was used to clone the hGH gene without KDEL and introducing a Xho1 site at the 3' end; primer SR25 (5'-CGG CTC GAG TTC ATC TTT AAA ACC TGA TCC) was used to clone the gene with KDEL.

In vitro transcripts of the 125C vector constructs including hGH were prepared by linearizing approximately 20 ug of DNA in 100 uL volume. Extent of linearization was assessed by gel electrophoresis of a 2 uL sample. Linearized DNA was cleaned using a PCT purification kit, from which it was eluted in 50 uL. A transcription mix was prepared in a 25 uL volume with 2.5 uL of 10×T7 buffer, 2.5 uL of 100 mM DTT, 0.5 uL of RNAsin (Promega), 1.25 uL NTP mix (20 mM A, C, U; 2 mM G; Pharmacia-Amersham); 1.25 uL Cap (5 mM diguanosine triphosphate; Pharmacia-Amersham), and 4 uL 25 mM $MgCl_2$. The mixture was warmed to 37° C. for 1 minute. 1.5-2 ug DNA were added in 12 uL of water, and the combination was warmed at 37° C. for 2 minutes. 1 uL of T7 polymerase (50 U/uL; New England Biolabs) was added, and the reaction were incubated for 15 minutes. 2 ul of 12.5 mM GTP were added by touching the tip of a pipette to the liquid (do not pipette up and down). The reaction was incubated at 37° C. for 1 h 15 minutes. A 2.5 uL aliquot was visualized on a gel; the remainder was frozen.

The resulting constructs were tested in both a protoplast system and in intact plants. Tobacco protoplasts were inoculated with each the various transcripts via electroporation (i.e., plants were inoculated with transcripts from individual constructs, not with a combination of different transcripts). Plant leaves were inoculated by diluting the transcription reaction through addition of 25 uL water and 50 uL FES. Plants were dusted with carborundum powder that acts as an abrasive. 25 uL aliquots of the transcription reaction/FES solution were then gently rubbed on the surface of each of two leaves. The plants were then maintained in the growth room at 21° C. under 12 hour light and 12 hour dark conditions.

*Nicotiana tabacum* suspension protoplasts were harvested at two time points: 24 and 48 hours post inoculation, so that each aliquot contained 500,000 protoplasts. Approximately 2 million protoplasts were used per inoculation of 25 uL transcript. The protoplasts were pelleted by centrifugation and the pellet was resuspended in 50 uL buffer (a mixture of Bradley's protein extraction buffer and Laemmli loading buffer). The samples (10 uL) were analyzed by PAGE followed by Western blot hybridization analysis using antiserum to hGH from chicken and anti-chicken IgG conjugated to alkaline phosphatase. Standard hGH was run as a standard. NBT-BCIP was used to develop the blots. FIG. 7 shows the results of the experiment.

The results indicate that a higher yield of hGH was obtained from tobacco suspension protoplasts at 24 h than at 48 h post inoculation. The position of the band corresponding to hGH from infected protoplasts indicates a slightly higher molecular weight than standard hGH. This could be due to the KDEL sequence attached to the 3' end of the hGH protein.

Nicotiana benthamiana plants were also inoculated with in vitro transcripts, and the plants were monitored for production of hGH. No signal specific to the protein could be detected at 5 dpi, although at 11 dpi we could detect a signal for hGH in the upper leaves of inoculated plants (FIG. 8).

Example 3

Transient Expression of a Human Insulin Transgene

We have made constructs to express insulin and proinsulin in plants using our plant virus-based transient expression vectors D4 and 125C. The following primers were used to clone proinsulin into 125C and D4, relying on Pac1 and Xho1 sites for cloning, and adding KDEL at the 3', end of each peptide:

1) Pac1 site at 5' end of insulin ORF (B peptide): SR30 5'-ccg tta att aatg ttt gtt aat caa cat-3' (SEQ ID NO:5)
2) Xho1 site at 3' end of A peptide with KDEL SR31 5'-cgg ctc gag tca gag ttc atc gtt aca gta gtt ctc aag-3' (SEQ ID NO:6)

Example 4

Co-Infection and Cross-Complementation of Viral Vectors

This example demonstrates that a coat protein defective TMV-based expression vector can be complemented by an AlMV vector that supplies CP in trans.

D4C3GFP is a TMV-based expression vector that is deficient in CP production (Shivprasad et al., 1999: TTT-GFP) as a result of deletion of the TMV CP coding region and the its replacement with the C3GFP gene, which is placed under the control of the TMVCP subgenomic promoter (see FIG. 9b). The C3GFP gene was recloned into D4 by overlapping PCR to eliminate the Nco1 and Xho1 sites in the C3GFP nucleotide sequence to facilitate further cloning steps. A polylinker PstI-NotI-XhoI was introduced at the 3'end of C3GFP gene. The PCR product digested with PacI-XhoI was cloned into D4 resulting in the version of D4C3GFP shown in FIG. 9c.

The primers we used to modify the C3GFP gene and eliminate Nco1 and Xho1 sites are:

```
1) C3GFP.Pac1.For(N)
GGGAG.ATCTTLAATTA.ATGGC.TAGCA.AAGGA.GAAGA.A    36 nt
(SEQ ID NO:7)

2) C3GFP.Xho1.Rev(N)
CCCCT.CGAGC.GGCCG.CTGCA.GTTAT.TTGTA.GAGCT.     45 nt
CATCC.ATGCC
(SEQ ID NO:8)

3) C3GFP.Nco1.For
GTTCC.CTGGC.CAACA.CTTGT.CAC                    23 nt
(SEQ ID NO:9)

4) C3GFP.Nco1.Rev
TAGTG.ACAAG.TGTTG.GCCAG.GG                     22 nt
(SEQ ID NO:10)

5) C3GFP.Xho1.For
GGACA.CAAAC.TGGAG.TACAA.CTATA                  25 nt
(SEQ ID NO:11)

6) C3GFP.Xho1.Rev
AGTTA.TAGTT.GTACT.CCAGT.TTGTG                  25 nt
(SEQ ID NO:12)
```

-continued

```
7) (BgIII)-PacI
>AUG...HindIII...NcoI...NdeI...BsrGI...MluI...

XhoI...BamHI...MfeI(MunI)...SalI...SacI...TAA<

PstI...NotI...XhoI
```

Three constructs that contained full-length or portions of the 3'-untranslated region (3' UTR) of AlMV RNA3 were then generated. In each of these constructs, sequences encoding C3GFP under control of the subgenomic TMV CP promoter were present upstream of AlMV RNA3 3'-UTR sequences (either full-length or a portion of the UTR), to allow us to precisely identify the sequences of the AlMV RNA3 3' UTR required for assembly and movement of TMV genomic RNA (either in trans or in cis). The RNA3 sequences were inserted between the Not1 and XhoI sites of the new D4C3GFP vector as Not1-Sal1 fragments, resulting in the constructs SR25 (nts 1859-1941 of RNA3), SR26 (nts. 1859-1969 of RNA3) and SR27 (nts. 1859-2037 of RNA3, i.e., the entire 3' UTR) (FIG. 9d). In addition to sequences from the AlMV RNA3 3' UTR, SR25, SR26, and SR27 also include sequences from the TMV 3' UTR (i.e., the UTR from the TMV genomic transcript) downstream of the inserted AlMV sequences. These sequences are TMV nucleotides 6192-6395, as in the D4 construct. The TMV-based viruses (SR25, SR26, and SR27) are defective in long-distance movement because the TMV coat protein is essential for effective phloem-mediated long distance transport and systemic infection of TMV.

The primers used to generate D4-based constructs with AlMV RNA3 3'-UTR sequences were:

1) SR-52 5' primer with Xho1-Pst1 sites at nt 1859 (plus sense) 5'-CCGCTCGAGCTGCAGTGTACCCCAT-TAATTTGG-3' (SEQ ID NO:13)
2) SR-53 3' primer at nt 1941 of AlMV RNA3 with Not1-Sal1 sites: minus sense 5'-CGGGTCGACGCGGCCGCGAAT-AGGACTTCATACCT-3' (SEQ ID NO:14)
3) SR-54 3' primer with Not1-Sal 1 sites at nt 1969 of AlMV RNA3: minus sense 5'-CGGGTCGACGCGGCCG-CAATATGAAGTCGATCCTA-3' (SEQ ID NO:15)
4) SR-55 3' primer with Not1-Sal 1 sites at nt 2037 (minus sense) 5'-CGGGTCGACGCGGCCGCGCATCCCT-TAGGGGCATT-3' (SEQ ID NO: 16).

The resulting plasmids were then transcribed using T7 polymerase and the in vitro transcripts used to inoculate Nicotiana benthamiana plants. In vitro transcripts of SR25, SR26, SR27, and a wild type AlMV construct were prepared by linearizing approximately 20 ug of DNA in 100 uL volume. Extent of linearization was assessed by gel electrophoresis of a 2 uL sample. Linearized DNA was cleaned using a PCT purification kit, from which it was eluted in 50 uL. A transcription mix was prepared in a 25 uL volume with 2.5 uL of 10×T7 buffer, 2.5 uL of 100 mM DTT, 0.5 uL of RNAsin (Promega), 1.25 uL NTP mix (20 mM A, C, U; 2 mM G; Pharmacia-Amersham); 1.25 uL Cap (5 mM diguanosine triphosphate; Pharmacia-Amersham), and 4 uL 25 mM $MgCl_2$. The mixture was warmed to 37° C. for 1 minute. 1.5-2 ug DNA were added in 12 uL of water, and the combination was warmed at 37° C. for 2 minutes. 1 uL of T7 polymerase (50 U/uL; New England Biolabs) was added, and the reaction was incubated for 15 minutes (SR25, SR26, SR27 constructs) or 2 hours (AlMV construct). 2 ul of 12.5 mM GTP were added by touching the tip of a pipette to the liquid (do not pipette up and down). The reaction was incubated at 37° C. for 1 h 15 minutes (SR25, SR26, SR27 constructs) or 30 minutes (AlMV construct). A 2.5 uL aliquot was visualized on a gel; the remainder was frozen.

Plant leaves were inoculated with SR25, SR26, or SR27 by diluting the transcription reaction through addition of 25 uL water and 50 uL FES. Plants were dusted with carborundum powder that acts as an abrasive. 25 uL aliquots of the transcription reaction/FES solution were then gently rubbed on the surface of each of two leaves. The plants were then maintained in the growth room at 21° C. under 12 hour light and 12 hour dark conditions.

Two weeks post inoculation, when SR25, SR26, SR27 had spread in the inoculated leaves, which was visualized by exposing the plants to long-wave ultraviolet light (366 nm), the same leaves were inoculated with wild type AlMV transcripts as described for the TMV-based vectors.

Two weeks post infection with AlMV, diffuse GFP fluorescence could be observed in upper leaves of plants infected with SR27 and AlMV but not with SR25 or SR26 and AlMV. FIG. 10a shows a picture of a plant that was co-inoculated with SR27 and AlMV. The image (taken under UV light) demonstrates spread of virus into the upper un-inoculated leaves. Fluorescence is caused by the accumulation of GFP. FIG. 10c shows the same plant as in FIG. 10a, under normal light. FIG. 10b (taken under UV light) shows a picture of a plant that was inoculated with SR27 only. Lack of fluorescence in the upper leaves indicates that virus infection was limited to locally inoculated leaves. These results indicate that the CP-deficient TMV-based virus (SR27) containing the GFP transgene moved through the phloem into the upper leaves with the help of AlMV. Generally (e.g., in the absence of trans-complementation from another virus) D4C3GFP only moves into the major veins of the upper leaves 40-45 d.p.i., and SR27 requires similar or even longer periods of time to move into the upper leaves in this system. This result indicates that AlMV can be used as a source for the coat protein that will complement and allow movement of a viral vector that is deficient in one or more coat protein components systemically and provide expression of foreign proteins, including complex proteins such as antibodies. The complementing CP components can be from related (other alfamoviruses, ilarviruses, bromoviruses) or unrelated viruses (TMV, CMV, etc.)

Constructs related to SR27 but containing the hGH gene (described above in Example 2) instead of the gene encoding GFP have also been generated and are in the process of being tested.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

We claim:

1. A producer vector comprising (a) one or more components of a tobacco mosaic virus; and (b) a polynucleotide of interest, wherein the vector is defective for cell-to-cell movement or systemic movement, and wherein the vector comprises at least one polynucleotide encoding a replicase protein of a plant virus and comprises sufficient non-coding portions to allow self-replication.

2. A producer vector comprising (a) one or more components of an alfalfa mosaic virus; and (b) a polynucleotide of interest, wherein the vector is defective for cell-to-cell movement or systemic movement, and wherein the vector comprises at least one polynucleotide encoding a replicase protein of a plant virus and comprises sufficient non-coding portions to allow self-replication.

3. The producer vector of claim 1 or 2, wherein the vector is defective for both cell-to-cell movement and systemic movement.

4. A method of expressing a polynucleotide of interest comprising:

(a) introducing the vector of claim 3 into a plant or plant cell;
(b) maintaining the plant cell or plant cell under conditions and for a time sufficient that the polynucleotide is expressed.

5. The method of claim 4, wherein the polynucleotide encodes a pharmaceutical protein of interest.

6. The method of claim 4, wherein the method comprises steps of:
(a) introducing a second vector into the plant or plant cell, wherein the second vector, or both, comprises a gene that encodes a replicase protein;
(b) maintaining the plant or plant cell under conditions and for a time sufficient that the polynucleotide is expressed in at least some plant cells.

7. The method of claim 6, wherein the second vector comprises a polynucleotide of interest, the method comprising steps of:
maintaining the plant or plant cell under conditions and for a time sufficient that the polynucleotide of the second vector is expressed in at least some plant cells.

8. The method of claim 7, wherein the second vector comprises a gene that encodes a replicase protein.

9. The method of claim 6, wherein the first and second polypeptides are polypeptide chains of a multimeric protein.

10. The method of claim 9, wherein the first and second polypeptides encode therapeutically active proteins.

11. The producer vector of claim 1 or 2, wherein the polynucleotide of interest encodes a pharmaceutical protein of interest.

12. A method of expressing a polynucleotide of interest comprising:
 (a) introducing the vector of claim 1 or 2 into a plant cell;
 (b) maintaining the plant cell under conditions and for a time sufficient that the polynucleotide is expressed.

* * * * *

UNITED STATES PATENT AND TRADEMARK OFFICE
CERTIFICATE OF CORRECTION

| | |
|---|---|
| PATENT NO. | : 7,491,509 B2 |
| APPLICATION NO. | : 10/770600 |
| DATED | : February 17, 2009 |
| INVENTOR(S) | : Oleg Fedorkin, Shailaja Rabindran and Vidadi Yusibov |

Page 1 of 1

It is certified that error appears in the above-identified patent and that said Letters Patent is hereby corrected as shown below:

Title Page, Item (56) References Cited, Col. 2, Line 29, delete "Eurppean" and insert --European--.

Signed and Sealed this

Fifteenth Day of September, 2009

David J. Kappos
*Director of the United States Patent and Trademark Office*

UNITED STATES PATENT AND TRADEMARK OFFICE
CERTIFICATE OF CORRECTION

PATENT NO. : 7,491,509 B2 Page 1 of 1
APPLICATION NO. : 10/770600
DATED : February 17, 2009
INVENTOR(S) : Fedorkin et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 358 days.

Delete the phrase "by 358 days" and insert -- by 346 days --

Signed and Sealed this

Thirtieth Day of March, 2010

David J. Kappos
*Director of the United States Patent and Trademark Office*